United States Patent [19]
Patel et al.

[11] Patent Number: 6,090,821
[45] Date of Patent: Jul. 18, 2000

[54] SUBSTITUTED QUINOLIN-2 (1H)-ONES USEFUL AS HIV REVERSE TRANSCRIPTASE INHIBITORS

[75] Inventors: Mona Patel, Wilmington, Del.; James D. Rodgers, Landenberg, Pa.

[73] Assignee: E. I. DuPont de Nemours and Company, Wilmington, Del.

[21] Appl. No.: 09/342,083

[22] Filed: Jun. 29, 1999

Related U.S. Application Data

[60] Provisional application No. 60/091,253, Jun. 30, 1998.

[51] Int. Cl.$^7$ .................... A61K 31/4704; A61P 31/18; C07D 215/227
[52] U.S. Cl. ................................. 514/312; 546/158
[58] Field of Search .................... 546/158; 514/312

[56] References Cited

U.S. PATENT DOCUMENTS

| | | | |
|---|---|---|---|
| 3,493,570 | 2/1970 | Plostnieks | 260/247.5 |
| 4,954,498 | 9/1990 | Mertens et al. | 514/254 |
| 4,985,448 | 1/1991 | Zilch et al. | 514/339 |
| 5,116,843 | 5/1992 | Mertens et al. | 514/253 |
| 5,358,949 | 10/1994 | Tabusa et al. | 514/254 |
| 5,371,226 | 12/1994 | Mederski et al. | 546/156 |
| 5,414,088 | 5/1995 | Von Der Saal et al. | 546/158 |
| 5,519,021 | 5/1996 | Young et al. | 514/230.5 |

FOREIGN PATENT DOCUMENTS

| | | |
|---|---|---|
| 0290153 | 11/1988 | European Pat. Off. |
| 0419132 | 3/1991 | European Pat. Off. |
| 0561252 | 9/1993 | European Pat. Off. |
| 0569083 | 11/1993 | European Pat. Off. |
| 0582455 | 2/1994 | European Pat. Off. |
| 0638571 | 2/1995 | European Pat. Off. |
| 3701277 | 7/1988 | Germany . |
| 3803775 | 8/1989 | Germany . |
| 3932953 | 4/1991 | Germany . |
| 9405638 | 3/1994 | WIPO . |
| 9529920 | 11/1995 | WIPO . |
| 9807716 | 2/1998 | WIPO . |

OTHER PUBLICATIONS

Dolle et al., Studies towards 4–C–Alkylation of Pyridin–2(1H)–one Derivatives, Tetrahedron, vol. 53, No. 37 (1997) pp. 12505–12524.

Chemical Abstracts, vol. 128, No. 1, (Jan. 5, 1998) Abstract No. 3807r.

Chemical Abstracts, vol. 125, No. 15, (Oct. 7, 1996) Abstract No. 195124y.

Chemical Abstracts, vol. 118, No. 18, (May 3, 1993) Abstract No. 179818c.

Chemical Abstracts, vol. 113, No. 18, (Oct. 29, 1990) Abstract No. 154342b.

Chemical Abstracts, vol. 111, No. 6, (Aug. 7, 1989), Abstract No. 48005t.

Chemical Abstracts, vol. 109, No. 6, (Aug. 8, 1988), Abstract No. 46052r.

Chemical Abstracts, vol. 106, No. 25, (Jun. 22, 1987), Abstract No. 213778d.

Chemical Abstracts, vol. 94, No. 17, (Apr. 27, 1981), Abstract No. 139634u.

Schmutz et al., "Synthese der isomeren 3,4–Dimethyl–4–phenyl–3,4–dihydro–carbostyrile", Helvetica Chimica Acta., vol. 53, No. 1 (1970), pp. 89–94.

Hill et al., "The absolute configuration of physostigmine", Tetrahedron, vol. 25 (1969) pp. 1249–1260.

*Primary Examiner*—Evelyn Mei Huang

[57] ABSTRACT

This invention relates generally to quinolin-2(1H)-ones and derivatives thereof of Formula (I):

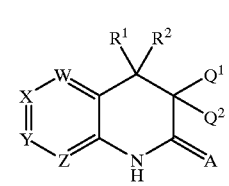

(I)

or stereoisomeric forms, stereoisomeric mixtures, or pharmaceutically acceptable salt forms thereof, which are useful as inhibitors of HIV reverse transcriptase, pharmaceutical compositions and diagnostic kits comprising the same, methods of using the same for treating viral infection or as assay standards or reagents, and intermediates and processes for making the same.

15 Claims, No Drawings

SUBSTITUTED QUINOLIN-2 (1H)-ONES USEFUL AS HIV REVERSE TRANSCRIPTASE INHIBITORS

This application claims the benefit of provisional application 60/091253 filed on Jun. 30, 1998.

FIELD OF THE INVENTION

This invention relates generally to quinolin-2(1H)-ones which are useful as inhibitors of HIV reverse transcriptase, pharmaceutical compositions and diagnostic kits comprising the same, methods of using the same for treating viral infection or as assay standards or reagents, and intermediates and processes for making the same.

BACKGROUND OF THE INVENTION

Two distinct retroviruses, human immunodeficiency virus (HIV) type-1 (HIV-1) or type-2 (HIV-2), have been etiologically linked to the immunosuppressive disease, acquired immunodeficiency syndrome (AIDS). HIV seropositive individuals are initially asymptomatic but typically develop AIDS related complex (ARC) followed by AIDS. Affected individuals exhibit severe immunosuppression which predisposes them to debilitating and ultimately fatal opportunistic infections.

The disease AIDS is the end result of an HIV-1 or HIV-2 virus following its own complex life cycle. The virion life cycle begins with the virion attaching itself to the host human T-4 lymphocyte immune cell through the bonding of a glycoprotein on the surface of the virion's protective coat with the CD4 glycoprotein on the lymphocyte cell. Once attached, the virion sheds its glycoprotein coat, penetrates into the membrane of the host cell, and uncoats its RNA. The virion enzyme, reverse transcriptase, directs the process of transcribing the RNA into single-stranded DNA. The viral RNA is degraded and a second DNA strand is created. The now double-stranded DNA is integrated into the human cell's genes and those genes are used for virus reproduction.

At this point, RNA polymerase transcribes the integrated DNA into viral RNA. The viral RNA is translated into the precursor gag-pol fusion polyprotein. The polyprotein is then cleaved by the HIV protease enzyme to yield the mature viral proteins. Thus, HIV protease is responsible for regulating a cascade of cleavage events that lead to the virus particle's maturing into a virus that is capable of full infectivity.

The typical human immune system response, killing the invading virion, is taxed because the virus infects and kills the immune system's T cells. In addition, viral reverse transcriptase, the enzyme used in making a new virion particle, is not very specific, and causes transcription mistakes that result in continually changed glycoproteins on the surface of the viral protective coat. This lack of specificity decreases the immune system's effectiveness because antibodies specifically produced against one glycoprotein may be useless against another, hence reducing the number of antibodies available to fight the virus. The virus continues to reproduce while the immune response system continues to weaken. Eventually, the HIV largely holds free reign over the body's immune system, allowing opportunistic infections to set in and without the administration of antiviral agents, immunomodulators, or both, death may result.

There are at least three critical points in the virus's life cycle which have been identified as possible targets for antiviral drugs: (1) the initial attachment of the virion to the T-4 lymphocyte or macrophage site, (2) the transcription of viral RNA to viral DNA (reverse transcriptase, RT), and (3) the processing of gag-pol protein by HIV protease.

Inhibition of the virus at the second critical point, the viral RNA to viral DNA transcription process, has provided a number of the current therapies used in treading AIDS. This transcription must occur for the virion to reproduce because the virion's genes are encoded in RNA and the host cell reads only DNA. By introducing drugs that block the reverse transcriptase from completing the formation of viral DNA, HIV-1 replication can be stopped.

A number of compounds that interfere with viral replication have been developed to treat AIDS. For example, nucleoside analogs, such as 3'-azido-3'-deoxythymidine (AZT), 2',3'-dideoxycytidine (ddC), 2',3'-dideoxythymidinene (d4T), 2',3'-dideoxyinosine (ddI), and 2',3'-dideoxy-3'-thia-cytidine (3TC) have been shown to be relatively effective in halting HIV replication at the reverse transcriptase (RT) stage.

An active area of research is in the discovery of non-nucleoside HIV reverse transcriptase inhibitors. As an example, it has been found that certain benzoxazinones and quinazolinones are active in the inhibition of HIV reverse transcriptase, the prevention or treatment of infection by HIV and the treatment of AIDS.

U.S. Pat. No. 5,519,021 describes reverse transcriptase inhibitors which are benzoxazinones of the formula:

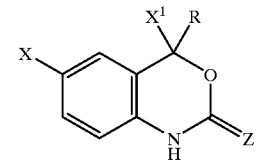

wherein X is a halogen, Z may be O.

WO 95/29920 describes suksdorfin analogs according to the Formula (III)

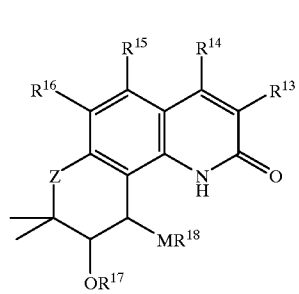

(III)

which are useful as antiviral and immunostimulating agents. Compounds of this sort are not considered to be part of the present invention.

U.S. Pat. No. 5,358,949 describes carbostyril derivatives of forumla (AA)

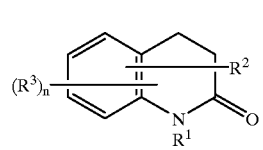

(AA)

which are useful as anti-arrhythmia agents. The application describes 3-substituted quinalinones and dihydroquinalinones, generally, wherein n is 0, 1, or 2; $R^2$ or $R^3$ can be a variety of groups, however, $R^2$ and $R^3$ can not be substituted on the same position at the same time. However, U.S. Pat. No. 5,358,949 does not disclose, by exemplification, compounds wherein $R^2$ or $R^3$ are —$CF_3$, —$CF_2CF_3$, —$CF_2CF_2CF_3$, nor compounds wherein n=2 and the 4 position of the quinaline core is disubstituted, nor where $R^2$ or $R^3$ are alkynyls. Compounds of U.S. Pat. No. 5,358,949 are not considered to be part of the present invention.

Even with the current success of reverse transcriptase inhibitors, it has been found that HIV patients can become resistant to a single inhibitor. Thus, it is desirable to develop additional inhibitors to further combat HIV infection.

SUMMARY OF THE INVENTION

Accordingly, one object of the present invention is to provide novel reverse transcriptase inhibitors.

It is another object of the present invention to provide a novel method for treating HIV infection which comprises administering to a host in need of such treatment a therapeutically effective amount of at least one of the compounds of the present invention or a pharmaceutically acceptable salt form thereof.

It is another object of the present invention to provide a novel method for treating HIV infection which comprises administering to a host in need thereof a therapeutically effective combination of (a) one of the compounds of the present invention and (b) one or more compounds selected form the group consisting of HIV reverse transcriptase inhibitors and HIV protease inhibitors.

It is another object of the present invention to provide pharmaceutical compositions with reverse transcriptase inhibiting activity comprising a pharmaceutically acceptable carrier and a therapeutically effective amount of at least one of the compounds of the present invention or a pharmaceutically acceptable salt form thereof.

It is another object of the present invention to provide a method of inhibiting HIV present in a body fluid sample which comprises treating the body fluid sample with an effective amount of a compound of the present invention.

It is another object of the present invention to provide a kit or container containing at least one of the compounds of the present invention in an amount effective for use as a standard or reagent in a test or assay for determining the ability of a potential pharmaceutical to inhibit HIV reverse transcriptase, HIV growth, or both.

These and other objects, which will become apparent during the following detailed description, have been achieved by the inventors' discovery that compounds of Formula (I):

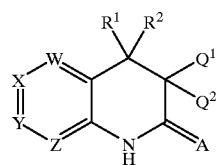

wherein $R^1$, $R^2$, $Q^1$, $Q^2$, A, W, X, Y, and Z are defined below, stereoisomeric forms, mixtures of stereoisomeric forms, or pharmaceutically acceptable salt forms thereof, are effective reverse transcriptase inhibitors.

DETAILED DESCRIPTION OF PREFERRED EMBODIMENTS

[1] Thus, in a first embodiment, the present invention provides a novel compound of Formula (I):

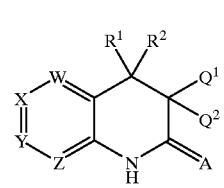

or a stereoisomer or pharmaceutically acceptable salt form thereof, wherein:

A is O or S;

W is N or $CR^3$;

X is N or $CR^{3a}$;

Y is N or $CR^{3b}$;

Z is N or $CR^{3c}$;

provided that the number of W, X, Y, and Z which are N, is zero, one or two;

$R^1$ is cyclopropyl or $C_{1-3}$ alkyl substituted with 0–7 halogen;

$R^2$ is selected from
  $C_{1-6}$ alkyl substituted with 0–2 $R^4$,
  $C_{2-5}$ alkenyl substituted with 0–2 $R^4$,
  $C_{2-5}$ alkynyl substituted with 0–1 $R^4$,
  $C_{3-6}$ cycloalkyl substituted with 0–2 $R^5$,
  phenyl substituted with 0–2 $R^5$, and
  3–6 membered heterocyclic system containing 1–3 heteroatoms selected from O, N, and S, substituted with 0–2 $R^5$;

$R^3$ is selected from $C_{1-4}$ alkyl, —OH, $C_{1-4}$ alkoxy, —$OCF_3$, F, Cl, Br, I, —$NR^{14}R^{15}$, —$NO_2$, —CN, —$C(O)R^{16}$, —$NHC(O)R^{17}$, —$NHC(O)NR^{14}R^{15}$, —$NHSO_2R^{18}$, and —$SO_2NR^{14}R^{15}$;

$R^{3a}$ is selected from $C_{1-4}$ alkyl, —OH, $C_{1-4}$ alkoxy, —$OCF_3$, F, Cl, Br, I, —$NR^{14}R^{15}$, —$NO_2$, —CN, —$C(O)R^{16}$, —$NHC(O)R^{17}$, —$NHC(O)NR^{14}R^{15}$, —$NHSO_2R^{18}$, and —$SO_2NR^{14}R^{15}$;

alternatively, $R^3$ and $R^{3a}$, when substituents on adjacent carbon atoms, are taken together with the carbon atoms to which they are attached to form —O—$CH_2$—O—, —O—$CH_2$—$CH_2$—O—, or —CH=CH—CH=CH—;

$R^{3b}$ is selected from $C_{1-4}$ alkyl, —OH, $C_{1-4}$ alkoxy, —$OCF_3$, F, Cl, Br, I, —$NO_2$, —CN, —$C(O)R^{16}$, —$NHC(O)R^{17}$, —$NHC(O)NR^{14}R^{15}$, —$NHSO_2R^{18}$, and —$SO_2NR^{14}R^{15}$;

alternatively, $R^{3a}$ and $R^{3b}$, when substituents on adjacent carbon atoms, are taken together with the carbon atoms to which they are attached to form —O—$CH_2$—O—, —O—$CH_2$—$CH_2$—O—, or —CH=CH—CH=CH—;

$R^{3c}$ is selected from $C_{1-4}$ alkyl, —OH, $C_{1-4}$ alkoxy, —$OCF_3$, F, Cl, Br, I, —$NR^{14}R^{15}$, —$NO_2$, —CN, —$C(O)R^{16}$, —$NHC(O)R^{17}$, —$NHC(O)NR^{14}R^{15}$, —$NHSO_2R^{18}$, and —$SO_2NR^{14}R^{15}$;

alternatively, $R^{3b}$ and $R^{3c}$, when substituents on adjacent carbon atoms, are taken together with the carbon atoms to which they are attached to form —O—$CH_2$—O—, —O—$CH_2$—$CH_2$—O—, or —CH=CH—CH=CH—;

$R^4$ is selected from
  $C_{1-6}$ alkyl substituted with 0–2 $R^5$,
  $C_{3-10}$ carbocycle substituted with 0–$R^5$, phenyl substituted with 0–5 $R^5$, and a 5–10 membered heterocyclic system containing 1–3 heteroatoms selected from O, N, and S, substituted with 0–2 $R^5$;

$R^5$, at each occurrence, is independently selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;

$Q^1$ and $Q^2$ are independently selected from
H, —CHO, —CO$_2$R$^7$, —CH$_2$OR$^7$, —COR$^7$, —NO$_2$, —NH$_2$, —NHR$^7$, —N(R$^7$)$_2$, —NHCO$_2$R$^7$, —NHCOR$^7$, —OR$^7$, —OCOR$^7$,
$C_{1-3}$ alkyl substituted by 3–7 halogens;
$C_{1-6}$ alkyl substituted with 0–2 $R^8$,
$C_{2-6}$ alkenyl substituted with 0–2 $R^8$, and
$C_{2-6}$ alkynyl substituted with 0–2 $R^8$, alternatively, $Q^1$ and $Q^2$ can be taken together to form =O;

alternatively, $Q^1$ and $Q^2$ can be taken together to form:
a 3–6 membered spirocyclic ring, said spirocyclic ring containing 0, 1, or 2 oxygen atoms;

$R^7$ is selected from
H,
$C_{1-6}$ alkyl substituted with 0–2 $R^8$,
$C_{2-6}$ alkenyl substituted with 0–2 $R^9$,
$C_{2-6}$ alkynyl substituted with 0–1 $R^9$,
$C_{3-6}$ cycloalkyl substituted with 0–2 $R^9$,
phenyl substituted with 0–5 $R^9$, and
$C_{1-3}$ alkyl substituted by 3–7 halogens;

$R^8$ is selected from
$C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;
$C_{3-6}$ cycloalkyl substituted with 0–2 $R^9$,
phenyl substituted with 0–5 $R^9$,
5–10 membered heterocyclic system containing 1–3 heteroatoms selected from O, N, and S, substituted with 0–2 $R^9$; and, $R^9$ is selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, —SO$_2$NR$^{14}$R$^{15}$, and $C_{1-3}$ alkyl substituted by 3–7 halogens;

$R^{14}$ and $R^{15}$ are independently selected from H and $C_{1-4}$ alkyl;

alternatively, $R^{14}$ and $R^{15}$, together with the nitrogen to which they are attached, combine to form a 5–6 membered ring containing 0–1 Oxygen atoms;

$R^{16}$ is selected from H, OH, $C_{1-4}$ alkyl, $C_{1-4}$ alkoxy, and NR$^{14}$R$^{15}$;

$R^{17}$ is selected from $C_{1-3}$ alkyl and $C_{1-3}$ alkoxy; and $R^{18}$ is selected from $C_{1-4}$ alkyl and phenyl.

[2] In a preferred embodiment, the present invention provides a novel compound of Formula (II),

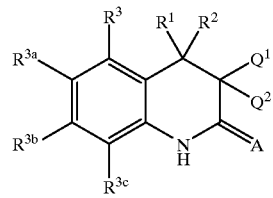

wherein:

A is O or S;

$R^1$ is cyclopropyl or $C_{1-3}$ alkyl substituted with 0–7 halogen;

$R^2$ is selected from
$C_{1-6}$ alkyl substituted with 0–2 $R^4$,
$C_{2-5}$ alkenyl substituted with 0–2 $R^4$,
$C_{2-5}$ alkynyl substituted with 0–1 $R^4$,
$C_{3-6}$ cycloalkyl substituted with 0–2 $R^5$,
phenyl substituted with 0–2 $R^5$, and
3–6 membered heterocyclic system containing 1–3 heteroatoms selected from O, N, and S, substituted with 0–2 $R^5$;

$R^3$ is selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;

$R^{3a}$ is selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;

$R^{3b}$ is selected from $C_{1-4}$ alkyl, —OH, $C_{1-4}$ alkoxy, —OCF$_3$, F, Cl, Br, I, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;

$R^{3c}$ is selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O) NR$^{14}$R$^{15}$, —NHSO$_2$R$^{18}$, and —SO$_2$NR$^{14}$R$^{15}$;

$R^4$ is selected from
$C_{1-6}$ alkyl substituted with 0–2 $R^5$,
$C_{3-10}$ carbocycle substituted with 0–2 $R^5$,
phenyl substituted with 0–5 $R^5$, and a
5–10 membered heterocyclic system containing 1–3 heteroatoms selected from O, N, and S, substituted with 0–2 $R^5$;

$R^5$, at each occurrence, is independently selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;

$Q^1$ and $Q^2$ are independently selected from
H, —CHO, —CO$_2$R$^7$, —CH$_2$OR$^7$, —COR$^7$, —NO$_2$, —NH$_2$, —NHR$^7$, —N(R$^7$)$_2$, —NHCO$_2$R$^7$, —NHCOR$^7$, —OR$^7$, —OCOR$^7$,
$C_{1-3}$ alkyl substituted by 3–7 halogens;
$C_{1-6}$ alkyl substituted with 0–2 $R^8$,
$C_{2-6}$ alkenyl substituted with 0–2 $R^8$, and
$C_{2-6}$ alkynyl substituted with 0–2 $R^8$, alternatively, $Q^1$ and $Q^2$ can be taken together to form =O;

alternatively, $Q^1$ and $Q^2$ can be taken together to form:
a 3–6 membered spirocyclic ring, said spirocyclic ring containing 0, 1, or 2 oxygen atoms;

$R^7$ is selected from
  H,
  $C_{1-6}$ alkyl substituted with 0–2 $R^8$,
  $C_{2-6}$ alkenyl substituted with 0–2 $R^9$,
  $C_{2-6}$ alkynyl substituted with 0–1 $R^9$,
  $C_{3-6}$ cycloalkyl substituted with 0–2 $R^9$,
  phenyl substituted with 0–5 $R^9$, and
  $C_{1-3}$ alkyl substituted by 3–7 halogens;
$R^8$ is selected from
  $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;
  $C_{3-6}$ cycloalkyl substituted with 0–2 $R^9$,
  phenyl substituted with 0–5 $R^9$,
  5–10 membered heterocyclic system containing 1–3 heteroatoms selected from O, N, and S, substituted with 0–2 $R^9$; and,
$R^9$ is selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, —SO$_2$NR$^{14}$R$^{15}$ and $C_{1-3}$ alkyl substituted by 3–7 halogens;
$R^{14}$ and $R^{15}$ are independently selected from H, methyl, ethyl, propyl, and butyl;
$R^{16}$ is selected from H, OH, methyl, ethyl, propyl, butyl, methoxy, ethoxy, propoxy, butoxy, and NR$^{14}$R$^{15}$;
$R^{17}$ is selected from methyl, ethyl, propyl, methoxy, ethoxy, and propoxy; and
$R^{18}$ is selected from methyl, ethyl, propyl, butyl, and phenyl.

[3] In a more preferred embodiment, the present invention provides a novel compound of Formula (II), wherein:
A is O;
$R^1$ is —CF$_3$, —CF$_2$CF$_3$, or —CF$_2$CF$_2$CF$_3$;
$R^2$ is selected from
  $C_{1-6}$ alkyl substituted with 0–2 $R^4$,
  $C_{2-5}$ alkenyl substituted with 0–2 $R^4$,
  $C_{2-5}$ alkynyl substituted with 0–1 $R^4$,
  $C_{3-6}$ cycloalkyl substituted with 0–2 $R^5$,
  phenyl substituted with 0–2 $R^5$, and
  3–6 membered heterocyclic system containing 1–3 heteroatoms selected from O, N, and S, substituted with 0–2 $R^5$;
$R^3$ is selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;
$R^{3a}$ is selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O) NR$^{14}$R$^{15}$, —NHSO$_2$R$^{18}$, and —SO$_2$NR$^{14}$R$^{15}$;
$R^{3b}$ is selected from $C_{1-4}$ alkyl, —OH, $C_{1-4}$ alkoxy, —OCF$_3$, F, Cl, Br, I, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;
$R^{3c}$ is selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;
$R^4$ is selected from
  $C_{1-6}$ alkyl substituted with 0–2 $R^5$,
  $C_{3-10}$ carbocycle substituted with 0–2 $R^5$,
  phenyl substituted with 0–5 $R^5$, and a
  5–10 membered heterocyclic system containing 1–3 heteroatoms selected from O, N, and S, substituted with 0–2 $R^5$;

$R^5$, at each occurrence, is independently selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;
$Q^1$ and $Q^2$ are independently selected from
  H, —CHO, —CO$_2$R$^7$, —CH$_2$OR$^7$, —COR$^7$, —NO$_2$, —NH$_2$, —NHR$^7$, —N(R$^7$)$_2$, —NHCO$_2$R$^7$, —NHCOR$^7$, —OR$^7$, —OCOR$^7$,
  $C_{1-3}$ alkyl substituted by 3–7 halogens;
  $C_{1-6}$ alkyl substituted with 0–2 $R^8$,
  $C_{2-6}$ alkenyl substituted with 0–2 $R^8$, and
  $C_{2-6}$ alkynyl substituted with 0–2 $R^8$,
alternatively, $Q^1$ and $Q^2$ can be taken together to form =O;
alternatively, $Q^1$ and $Q^2$ can be taken together to form:
  a 3–6 membered spirocyclic ring, said spirocyclic ring containing 0, 1, or 2 oxygen atoms;
$R^7$ is selected from
  H,
  $C_{1-6}$ alkyl substituted with 0–2 $R^8$,
  $C_{2-6}$ alkenyl substituted with 0–2 $R^9$,
  $C_{2-6}$ alkynyl substituted with 0–1 $R^9$,
  $C_{3-6}$ cycloalkyl substituted with 0–2 $R^9$,
  phenyl substituted with 0–5 $R^9$, and
  $C_{1-3}$ alkyl substituted by 3–7 halogens;
$R^8$ is selected from
  $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O) NR$^{14}$R$^{15}$, —NHSO$_2$R$^{18}$, and —SO$_2$NR$^{14}$R$^{15}$,
  $C_{3-6}$ cycloalkyl substituted with 0–2 $R^9$,
  phenyl substituted with 0–5 $R^9$,
  5–10 membered heterocyclic system containing 1–3 heteroatoms selected from O, N, and S, substituted with 0–2 $R^9$; and,
$R^9$ is selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, —SO$_2$NR$^{14}$R$^{15}$, and $C_{1-3}$ alkyl substituted by 3–7 halogens;
$R^{14}$ and $R^{15}$ are independently selected from H, methyl, and ethyl;
$R^{16}$ is selected from H, OH, methyl, ethyl, methoxy, ethoxy, and NR$^{14}$R$^{15}$;
$R^{17}$ is selected from methyl, ethyl, methoxy, and ethoxy; and
$R^{18}$ is selected from methyl, ethyl, and phenyl.

[4] In an even more preferred embodiment, the present invention provides a novel compound of Formula (II), wherein:
A is O;
$R^1$ is —CF$_3$ or —CF$_2$CF$_3$;
$R^2$ is selected from
  $C_{1-3}$ alkyl substituted with 0–1 $R^4$,
  $C_{2-3}$ alkenyl substituted with 0–1 $R^4$, and
  $C_{2-3}$ alkynyl substituted with 0–1 $R^4$,
$R^3$ is selected from H, methyl, ethyl, —OH, methoxy, ethoxy, —OCF$_3$, F, Cl, Br, I, —NR$^{14}$R$^{15}$, —NO$_2$, —CN, —C(O)R$^{16}$, —NHC(O)R$^{17}$, and —NHC(O) NR$^{14}$R$^{15}$;
$R^{3a}$ is selected from H, methyl, ethyl, —OH, methoxy, ethoxy, —OCF$_3$, F, Cl, Br, I, —NR$^{14}$R$^{15}$, —NO$_2$, —CN, —C(O)R$^{16}$, —NHC(O)R$^{17}$, and —NHC(O) NR$^{14}$R$^{15}$;

$R^{3b}$ is H or F;

$R^{3c}$ is selected from H, methyl, —OH, methoxy, and —OCF$_3$;

$R^4$ is selected from
cyclopropyl substituted with 0–1 $R^5$,
phenyl substituted with 0–3 $R^5$, and a
5–6 membered heterocyclic system containing 1–3 heteroatoms selected from O, N, and S, substituted with 0–1 $R^5$, wherein the heterocyclic system is selected from 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, 1-pyrazolyl, 3-pyrazolyl, and 4-pyrazolyl;

$R^5$, at each occurrence, is independently selected from methyl, ethyl, propyl, —OH, methoxy, ethoxy, propoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;

$Q^1$ is selected from:
H, —CHO, —CO$_2$R$^7$, —CH$_2$OR$^7$, —COR$^7$, —NO$_2$, —NH$_2$, —NHR$^7$, —N(R$^7$)$_2$, —NHCO$_2$R$^7$, —NHCOR$^7$, —OR$^7$, —OCOR$^7$, —CF$_3$, —CF$_2$CF$_3$, —CF$_2$CF$_2$CF$_3$,
$C_{1-4}$ alkyl substituted with 0–1 $R^8$,
$C_{2-3}$ alkenyl substituted with 0–1 $R^8$, and
$C_{2-3}$ alkynyl substituted with 0–1 $R^8$;

$Q^2$ is H;

alternatively, $Q^1$ and $Q^2$ can be taken together to form =O;

$R^7$ is selected from
H, —CF$_3$, —CF$_2$CF$_3$, —CF$_2$CF$_2$CF$_3$,
$C_{1-3}$ alkyl substituted with 0–1 $R^8$,
$C_{2-3}$ alkenyl substituted with 0–1 $R^9$,
$C_{2-3}$ alkynyl substituted with 0–1 $R^9$,
$C_{3-6}$ cycloalkyl substituted with 0–2 $R^9$, and
phenyl substituted with 0–2 $R^9$;

$R^8$ is selected from
methyl, ethyl, propyl, butyl, —OH, methoxy, ethoxy, propoxy, butoxy, —OCF$_3$, F, Cl, Br, I, —NR$^{14}$R$^{15}$, —NO$_2$, —CN, —C(O)R$^{16}$, —NHC(O)R$^{17}$, and —NHC(O)NR$^{14}$R$^{15}$,
$C_{3-6}$ cycloalkyl substituted with 0–2 $R^9$,
phenyl substituted with 0–5 $R^9$,
5–6 membered heterocyclic system containing 1–3 heteroatoms selected from O, N, and S, substituted with 0–2 $R^9$; wherein the heterocyclic system is selected from 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, 1-pyrazolyl, 3-pyrazolyl, and 4-pyrazolyl;

$R^9$ is selected from methyl, ethyl, propyl, butyl, —CF$_3$, —CF$_2$CF$_3$, —CF$_2$CF$_2$CF$_3$, —OH, methoxy, ethoxy, propoxy, butoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;

$R^{14}$ and $R^{15}$ are independently selected from H, methyl, and ethyl;

$R^{16}$ is selected from H, OH, methyl, ethyl, methoxy, ethoxy, and NR$^{14}$R$^{15}$; and $R^{17}$ is selected from methyl, ethyl, methoxy, and ethoxy.

In a further preferred embodiment, a compound of the present invention is of Formula (Ia)

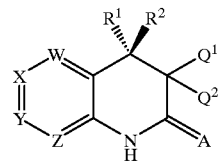

(Ia)

or a pharmaceutically acceptable salt thereof.

In a further preferred embodiment, a compound of the present invention is of Formula (Ib)

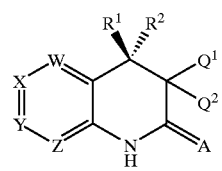

(Ib)

or a pharmaceutically acceptable salt thereof.

[5] In a most preferred embodiment, the compound of Formula (I) selected from:

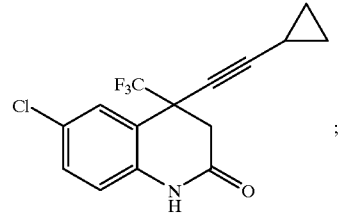
;

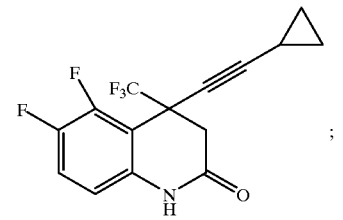
;

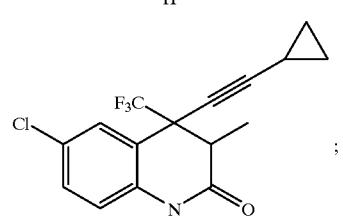
;

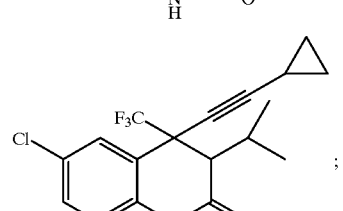
;

-continued

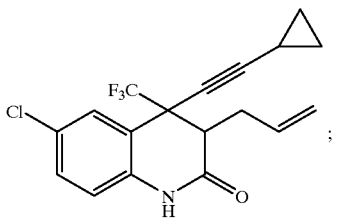

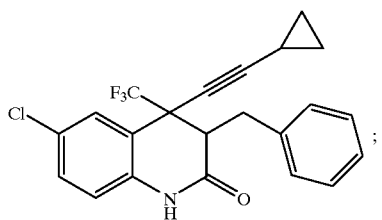

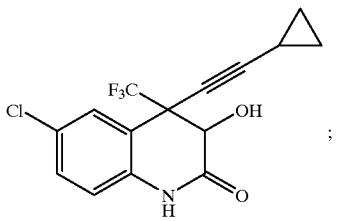

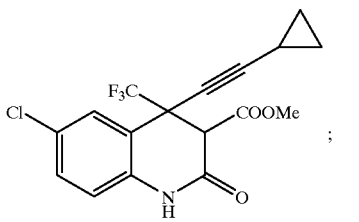

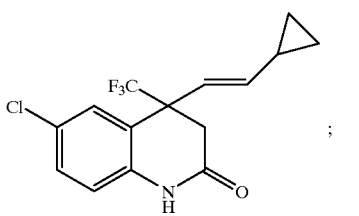

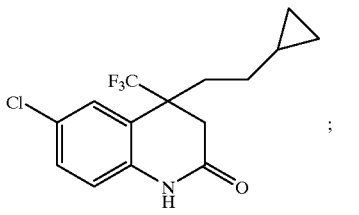

-continued

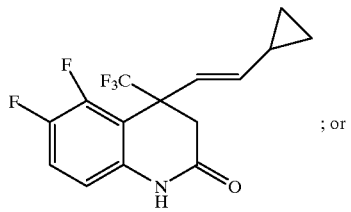

; or

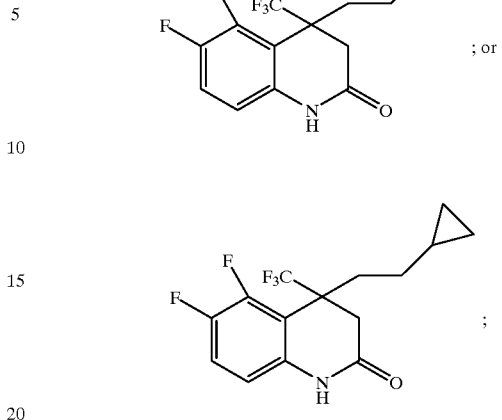

;

or a pharmaceutically acceptable salt thereof.

[6] In a second embodiment, the present invention provides a novel compound of Formula (I), wherein:

A is O or S;
W is N or $CR^3$;
X is N or $CR^{3a}$;
Y is N or $CR^{3b}$;
Z is N or $CR^{3c}$;
provided that one or two of W, X, Y, and Z are N,
$R^1$ is $C_{1-3}$ alkyl substituted with 0–7 halogen;
$R^2$ is selected from
  $C_{1-6}$ alkyl substituted with 0–2 $R^4$,
  $C_{2-5}$ alkenyl substituted with 0–2 $R^4$,
  $C_{2-5}$ alkynyl substituted with 0–1 $R^4$,
  $C_{3-6}$ cycloalkyl substituted with 0–2 $R^5$,
  phenyl substituted with 0–2 $R^5$, and
  3–6 membered heterocyclic system containing 1–3 heteroatoms selected from O, N, and S, substituted with 0–2 $R^5$;
$R^3$ is selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;
$R^{3a}$ is selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;
$R^{3b}$ is selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;
$R^{3c}$ is selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;
$R^4$ is selected from
  $C_{1-6}$ alkyl substituted with 0–2 $R^5$,
  $C_{3-10}$ carbocycle substituted with 0–2 $R^5$,
  phenyl substituted with 0–5 $R^5$, and a
  5–10 membered heterocyclic system containing 1–3 heteroatoms selected from O, N, and S, substituted with 0–2 $R^5$;
$R^5$, at each occurrence, is independently selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;
$Q^1$ and $Q^2$ are independently selected from H, —CHO, —CO$_2$R$^7$, —CH$_2$OR$^7$, —COR$^7$, —NO$_2$, —NH$_2$, —NHR$^7$, —N(R$^7$)$_2$, —NHCO$_2$R$^7$, —NHCOR$^7$, —OR$^7$, —OCOR$^7$, $C_{1-3}$ alkyl substituted by 3–7 halogens;
$C_{1-6}$ alkyl substituted with 0–2 $R^8$,
$C_{2-6}$ alkenyl substituted with 0–2 $R^8$, and
$C_{2-6}$ alkynyl substituted with 0–2 $R^8$, alternatively, $Q^1$ and $Q^2$ can be taken together to form =O;

alternatively, $Q^1$ and $Q^2$ can be taken together to form:
  a 3–6 membered spirocyclic ring, said spirocyclic ring containing 0, 1, or 2 oxygen atoms;

$R^7$ is selected from
  H,
  $C_{1-6}$ alkyl substituted with 0–2 $R^8$,
  $C_{2-6}$ alkenyl substituted with 0–2 $R^9$,
  $C_{2-6}$ alkynyl substituted with 0–1 $R^9$,
  $C_{3-6}$ cycloalkyl substituted with 0–2 $R^9$,
  phenyl substituted with 0–5 $R^9$, and
  $C_{1-3}$ alkyl substituted by 3–7 halogens;

$R^8$ is selected from
  $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$
  $C_{3-6}$ cycloalkyl substituted with 0–2 $R^9$,
  phenyl substituted with 0–5 $R^9$,
  5–10 membered heterocyclic system containing 1–3 heteroatoms selected from O, N, and S, substituted with 0–2 $R^9$; and, $R^9$ is selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, —SO$_2$NR$^{14}$R$^{15}$, and $C_{1-3}$ alkyl substituted by 3–7 halogens;

$R^{14}$ and $R^{15}$ are independently selected from H, methyl, ethyl, propyl, and butyl;

$R^{16}$ is selected from H, OH, methyl, ethyl, propyl, butyl, methoxy, ethoxy, propoxy, butoxy, and NR$^{14}$R$^{15}$;

$R^{17}$ is selected from methyl, ethyl, propyl, methoxy, ethoxy, and propoxy; and $R^{18}$ is selected from methyl, ethyl, propyl, butyl, and phenyl.

[7] In a preferred second embodiment, the present invention provides a novel compound of Formula (I), wherein:
  A is O;
  W is N or CR$^3$;
  X is N or CR$^{3a}$;
  Y is N or CR$^{3b}$;
  Z is N or CR$^{3c}$;
  provided that one or two of W, X, Y, and Z are N, $R^1$ is —CF$_3$, —CF$_2$CF$_3$, or —CF$_2$CF$_2$CF$_3$;

$R^2$ is selected from
  $C_{1-6}$ alkyl substituted with 0–2 $R^4$,
  $C_{2-5}$ alkenyl substituted with 0–2 $R^4$,
  $C_{2-5}$ alkynyl substituted with 0–1 $R^4$,
  $C_{3-6}$ cycloalkyl substituted with 0–2 $R^5$,
  phenyl substituted with 0–2 $R^5$, and
  3–6 membered heterocyclic system containing 1–3 heteroatoms selected from O, N, and S, substituted with 0–2 $R^5$;

$R^3$ is selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;

$R^{3a}$ is selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;

$R^{3b}$ is selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;

$R^{3c}$ is selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;

$R^4$ is selected from
  $C_{1-6}$ alkyl substituted with 0–2 $R^5$,
  $C_{3-10}$ carbocycle substituted with 0–2 $R^5$,
  phenyl substituted with 0–5 $R^5$, and a
  5–10 membered heterocyclic system containing 1–3 heteroatoms selected from O, N, and S, substituted with 0–2 $R^5$;

$R^5$, at each occurrence, is independently selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;

$Q^1$ and $Q^2$ are independently selected from
  H, —CHO, —CO$_2$R$^7$, —CH$_2$OR$^7$, —COR$^7$, —NO$_2$, —NH$_2$, —NHR$^7$, —N(R$^7$)$_2$, —NHCO$_2$R$^7$, —NHCOR$^7$, —OR$^7$, —OCOR$^7$,
  $C_{1-3}$ alkyl substituted by 3–7 halogens;
  $C_{1-6}$ alkyl substituted with 0–2 $R^8$,
  $C_{2-6}$ alkenyl substituted with 0–2 $R^8$, and
  $C_{2-6}$ alkynyl substituted with 0–2 $R^8$, alternatively, $Q^1$ and $Q^2$ can be taken together to form =O;

alternatively, $Q^1$ and $Q^2$ can be taken together to form:
  a 3–6 membered spirocyclic ring, said spirocyclic ring containing 0, 1, or 2 oxygen atoms;

$R^7$ is selected from
  H,
  $C_{1-6}$ alkyl substituted with 0–2 $R^8$,
  $C_{2-6}$ alkenyl substituted with 0–2 $R^9$,
  $C_{2-6}$ alkynyl substituted with 0–1 $R^9$,
  $C_{3-6}$ cycloalkyl substituted with 0–2 $R^9$,
  phenyl substituted with 0–5 $R^9$, and
  $C_{1-3}$ alkyl substituted by 3–7 halogens;

$R^8$ is selected from
  $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$ $C_{3-6}$ cycloalkyl substituted with 0–2 $R^9$,
  phenyl substituted with 0–5 $R^9$,
  5–10 membered heterocyclic system containing 1–3 heteroatoms selected from O, N, and S, substituted with 0–2 $R^9$; and, $R^9$ is selected from $C_{1-4}$ alkyl, —OH, $C_{1-4}$ alkoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, —SO$_2$NR$^{14}$R$^{15}$, and $C_{1-3}$ alkyl substituted by 3–7 halogens;

$R^{14}$ and $R^{15}$ are independently selected from H, methyl, ethyl, propyl, and butyl;

$R^{16}$ is selected from H, OH, methyl, ethyl, propyl, butyl, methoxy, ethoxy, propoxy, butoxy, and NR$^{14}$R$^{15}$;

$R^{17}$ is selected from methyl, ethyl, propyl, methoxy, ethoxy, and propoxy; and $R^{18}$ is selected from methyl, ethyl, propyl, butyl, and phenyl.

[8] In a more preferred second embodiment, the present invention provides a novel compound of Formula (I), wherein:

$R^1$ is —$CF_3$ or —$CF_2CF_3$;

$R^2$ is selected from
  $C_{1-3}$ alkyl substituted with 0–1 $R^4$,
  $C_{2-3}$ alkenyl substituted with 0–1 $R^4$,
  $C_{2-3}$ alkynyl substituted with 0–1 $R^4$, $R^3$ is selected from methyl, ethyl, —OH, methoxy, ethoxy, —$OCF_3$, F, Cl, Br, I, —$NR^{14}R^{15}$, —$NO_2$, —CN, —$C(O)R^{16}$, —$NHC(O)R^{17}$, and —$NHC(O)NR^{14}R^{15}$;

$R^{3a}$ is selected from methyl, ethyl, —OH, methoxy, ethoxy, —$OCF_3$, F, Cl, Br, I, —$NR^{14}R^{15}$, —$NO_2$, —CN, —$C(O)R^{16}$, —$NHC(O)R^{17}$, and —$NHC(O)NR^{14}R^{15}$;

$R^{3b}$ is selected from methyl, ethyl, —OH, methoxy, ethoxy, —$OCF_3$, F, Cl, Br, I, —$NR^{14}R^{15}$, —$NO_2$, —CN, —$C(O)R^{16}$, —$NHC(O)R^{17}$, and —$NHC(O)NR^{14}R^{15}$;

$R^{3c}$ is selected from methyl, —OH, methoxy, —$OCF_3$, F, Cl, Br, I, —$NR^{14}R^{15}$, —$NO_2$, —CN;

$R^4$ is selected from
  cyclopropyl substituted with 0–1 $R^5$,
  phenyl substituted with 0–3 $R^5$, and a
  5–6 membered heterocyclic system containing 1–3 heteroatoms selected from O, N, and S, substituted with 0–1 $R^5$, wherein the heterocyclic system is selected from 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, and 2-imidazolyl;

$R^5$, at each occurrence, is independently selected from methyl, ethyl, propyl, —OH, methoxy, ethoxy, propoxy, —$OCF_3$, F, Cl, Br, I, —$NR^{14}R^{15}$, —$NO_2$, —CN, —$C(O)R^{16}$, —$NHC(O)R^{17}$, —$NHC(O)NR^{14}R^{15}$, —$NHSO_2R^{18}$, and —$SO_2NR^{14}R^{15}$;

$Q^1$ and $Q^2$ are independently selected from
  H, —CHO, —$CO_2R^7$, —$CH_2OR^7$, —$COR^7$, —$NO_2$, —$NH_2$, —$NHR^7$, —$N(R^7)_2$, —$NHCO_2R^7$, —$NHCOR^7$, —$OR^7$, —$OCOR^7$, —$CF_3$, —$CF_2CF_3$, —$CF_2CF_2CF_3$,
  $C_{1-4}$ alkyl substituted with 0–1 $R^8$,
  $C_{2-3}$ alkenyl substituted with 0–1 $R^8$, and
  $C_{2-3}$ alkynyl substituted with 0–1 $R^8$,
alternatively, $Q^1$ and $Q^2$ can be taken together to form =O;

$R^7$ is selected from
  H, —$CF_3$, —$CF_2CF_3$, —$CF_2CF_2CF_3$,
  $C_{1-3}$ alkyl substituted with 0–1 $R^8$,
  $C_{2-3}$ alkenyl substituted with 0–1 $R^9$,
  $C_{2-3}$ alkynyl substituted with 0–1 $R^9$,
  $C_{3-6}$ cycloalkyl substituted with 0–2 $R^9$, and
  phenyl substituted with 0–2 $R^9$;

$R^8$ is selected from
  methyl, ethyl, propyl, butyl, —OH, methoxy, ethoxy, propoxy, butoxy, —$OCF_3$, F, Cl, Br, I, —$NR^{14}R^{15}$, —$NO_2$, —CN, —$C(O)R^{16}$, —$NHC(O)R^{17}$, and —$NHC(O)NR^{14}R^{15}$,
  $C_{3-6}$ cycloalkyl substituted with 0–2 $R^9$,
  phenyl substituted with 0–5 $R^9$,
  5–6 membered heterocyclic system containing 1–3 heteroatoms selected from O, N, and S, substituted with 0–2 $R^9$; wherein the heterocyclic system is selected from 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, and 2-imidazolyl;

$R^9$ is selected from methyl, ethyl, propyl, butyl, —$CF_3$, —$CF_2CF_3$, —$CF_2CF_2CF_3$, —OH, methoxy, ethoxy, propoxy, butoxy, —$OCF_3$, F, Cl, Br, I, —$NR^{14}R^{15}$, —$NO_2$, —CN, —$C(O)R^{16}$, —$NHC(O)R^{17}$, —$NHC(O)NR^{14}R^{15}$, —$NHSO_2R^{18}$, and —$SO_2NR^{14}R^{15}$;

$R^{14}$ and $R^{15}$ are independently selected from H, methyl, and ethyl;

$R^{16}$ is selected from H, OH, methyl, ethyl, methoxy, ethoxy, and $NR^{14}R^{15}$; and $R^{17}$ is selected from methyl, ethyl, methoxy, and ethoxy.

In a third embodiment, the present invention provides a novel pharmaceutical composition comprising a pharmaceutically acceptable carrier and a therapeutically effective amount of a compound of Formula (I) or (II) or pharmaceutically acceptable salt form thereof.

In a fourth embodiment, the present invention provides a novel method for treating HIV infection which comprises administering to a host in need of such treatment a therapeutically effective amount of a compound of Formula (I) or (II) or pharmaceutically acceptable salt form thereof.

In a fifth embodiment, the present invention provides a novel method of treating HIV infection which comprises administering, in combination, to a host in need thereof a therapeutically effective amount of:

(a) a compound of Formula (I) or II; and, (b) at least one compound selected from the group consisting of HIV reverse transcriptase inhibitors and HIV protease inhibitors.

In another preferred embodiment, the reverse transcriptase inhibitor is selected from efavirenz, AZT, ddC, ddI, d4T, 3TC, delavirdine, nevirapine, Ro 18,893, trovirdine, MKC-442, HBY 097, ACT, UC-781, UC-782, RD4-2025, and MEN 10979, and the protease inhibitor is selected from saquinavir, ritonavir, indinavir, amprenavir, nelfinavir, palinavir, BMS-232623, GS3333, KNI-413, KNI-272, LG-71350, CGP-61755, PD 173606, PD 177298, PD 178390, PD 178392, U-140690, and ABT-378.

In an even more preferred embodiment, the reverse transcriptase inhibitor is selected from AZT, efavirenz, and 3TC and the protease inhibitor is selected from saquinavir, ritonavir, nelfinavir, and indinavir.

In a still further preferred ebodiment, the reverse transcriptase inhibitor is AZT.

In another still further preferred embodiment, the reverse transcriptase inhibitor is efavirenz.

In another still further preferred embodiment, the protease inhibitor is indinavir.

In a sixth embodiment, the present invention provides a pharmaceutical kit useful for the treatment of HIV infection, which comprises a therapeutically effective amount of:

(a) a compound of Formula (I) or II; and, (b) at least one compound selected from the group consisting of HIV reverse transcriptase inhibitors and HIV protease inhibitors, in one or more sterile containers.

In a seventh embodiment, the present invention provides a novel method of inhibiting HIV present in a body fluid sample which comprises treating the body fluid sample with an effective amount of a compound of Formula (I) or II.

In a eighth embodiment, the present invention to provides a novel a kit or container comprising a compound of Formula (I) or (II) in an amount effective for use as a standard or reagent in a test or assay for determining the ability of a potential pharmaceutical to inhibit HIV reverse transcriptase, HIV growth, or both.

DEFINITIONS

As used herein, the following terms and expressions have the indicated meanings. It will be appreciated that the compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

The processes of the present invention are contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

The present invention is intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

As used herein, "alkyl" is intended to include both branched and straight-chain saturated aliphatic hydrocarbon groups having the specified number of carbon atoms; for example, "$C_{1-6}$ alkyl" denotes alkyl having 1 to 6 carbon atoms, ie. methyl, ethyl, propyl, butyl, pentyl, hexyl, and branched isomers therein. Examples of alkyls include, but are not limited to, methyl, ethyl, n-propyl, i-propyl, i-butyl, n-butyl, s-butyl, t-butyl, i-pentyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$, where v=1 to 3 and w=1 to (2v+1)). Examples of haloalkyl include, but are not limited to, trifluoromethyl, trichloromethyl, pentafluoroethyl, pentachloroethyl, heptafluoropropyl, and heptachloropropyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, cyclopentyl, or cyclohexyl. "Alkenyl" is intended to include hydrocarbon chains of either a straight or branched configuration and one or more unsaturated carbon-carbon bonds which may occur in any stable point along the chain, such as ethenyl, 1-methyl-ethenyl, 2-propenyl, 3-butenyl, 2-butenyl, 3-methyl-2-butenyl, and the like. "Alkynyl" is intended to include hydrocarbon chains of either a straight or branched configuration and one or more triple carbon-carbon bonds which may occur in any stable point along the chain, such as ethynyl, propynyl, 2-propynyl, butynyl, 2-butynyl, 3-butynyl, and the like.

"Halo" or "halogen" as used herein refers to fluoro, chloro, bromo and iodo. "Counterion" is used to represent a small, negatively charged species such as chloride, bromide, hydroxide, acetate, sulfate and the like.

As used herein, "aryl" or "aromatic residue" is intended to mean an aromatic moiety containing the specified number of carbon atoms, such as phenyl or naphthyl. As used herein, "carbocycle" or "carbocyclic residue" is intended to mean any stable 3- to 7-membered monocyclic or bicyclic or 7- to 14-membered bicyclic or tricyclic carbon ring, which may be saturated or partially unsaturated. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic system" is intended to mean a stable 5- to 6-membered monocyclic heterocyclic ring which is saturated partially unsaturated or unsaturated (aromatic), and which consists of carbon atoms and from 1 to 3 heteroatoms independently selected from the group consisting of N, O and S. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds one, then these heteroatoms are not adjacent to one another. It is preferred that the total number of S and O toms in the heterocycle is not more than one.

As used herein, the term "aromatic heterocyclic system" is intended to mean a stable 5- to 6-membered monocyclic heterocyclic aromatic ring which consists of carbon atoms and from 1 to 3 heterotams independently selected from the group consisting of N, O and S. It is preferred that the total number of S and O atoms in the aromatic heterocycle is not more than one.

Examples of heterocycles include, but are not limited to, 2-pyrrolidonyl, 2H-pyrrolyl, 4-piperidonyl, 6H-1,2,5-thiadiazinyl, 2H,6H-1,5,2-dithiazinyl, furanyl, furazanyl, imidazolidinyl, imidazolinyl, imidazolyl, isoxazolyl, morpholinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, tetrahydrofuranyl, 6H-1,2,5-thiadiazinyl, 1,2,3-thiadiazolyl, 1,2,4-thiadiazolyl, 1,2,5-thiadiazolyl, 1,3,4-thiadiazolyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, and 1,3,4-triazolyl. Preferred heterocycles include, but are not limited to, pyridinyl, furanyl, thienyl, pyrrolyl, pyrazolyl, imidazolyl, and oxazolidinyl. Also included are fused ring and spiro compounds containing, for example, the above heterocycles containing oxygen.

As used herein, "HIV reverse transcriptase inhibitor" is intended to refer to both nucleoside and non-nucleoside inhibitors of HIV reverse transcriptase (RT). Examples of nucleoside RT inhibitors include, but are not limited to, AZT, ddC, ddI, d4T, and 3TC. Examples of non-nucleoside RT inhibitors include, but are no limited to, efavirenz (DuPont Merck), delavirdine (Pharmacia and Upjohn U90152S), nevirapine (Boehringer Ingelheim), Ro 18,893 (Roche), trovirdine (Lilly), MKC-442 (Triangle), HBY 097 (Hoechst), ACT (Korean Research Institute), UC-781 (Rega Institute), UC-782 (Rega Institute), RD4–2025 (Tosoh Co. Ltd.), PNU142721 (Pharmacia and Upjohn), and MEN 10979 (Menarini Farmaceutici).

As used herein, "HIV protease inhibitor" is intended to refer to compounds which inhibit HIV protease. Examples include, but are not limited, saquinavir (Roche, Ro31-8959), ritonavir (Abbott, ABT-538), indinavir (Merck, MK-639), amprenavir (Vertex/Glaxo Wellcome), nelfinavir (Agouron, AG-1343), palinavir (Boehringer Ingelheim), BMS-232623 (Bristol-Myers Squibb), GS3333 (Gilead Sciences), KNI-413 (Japan Energy), KNI-272 (Japan Energy), LG-71350 (LG Chemical), CGP-61755 (Ciba-Geigy), DMP450 (DuPont Merck), PD 173606 (Parke Davis), PD 177298 (Parke Davis), PD 178390 (Parke Davis), PD 178392 (Parke Davis), U-140690 (Pharmacia and Upjohn), and ABT-378. Additional examples include the cyclic protease inhibitors disclosed in WO93/07128, WO 94/19329, WO 94/22840, and PCT Application Number US96/03426.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Prodrugs" are intended to include any covalently bonded carriers which release the active parent drug according to Formula (I) or other formulas or compounds of the present invention in vivo when such prodrug is administered to a mammalian subject. Prodrugs of a compound of the present invention, for example Formula (I), are prepared by modifying functional groups present in the compound in such a way that the modifications are cleaved, either in routine manipulation or in vivo, to the parent compound. Prodrugs include compounds of the present invention wherein the hydroxy or amino group is bonded to any group that, when the prodrug is administered to a mammalian subject, cleaves to form a free hydroxyl or free amino, respectively. Examples of prodrugs include, but are not limited to, acetate, formate and benzoate derivatives of alcohol and amine functional groups in the compounds of the present invention, and the like.

"Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

"Therapeutically effective amount" is intended to include an amount of a compound of the present invention or an amount of the combination of compounds claimed effective to inhibit HIV infection or treat the symptoms of HIV infection in a host. The combination of compounds is preferably a synergistic combination. Synergy, as described for example by Chou and Talalay, Adv. Enzyme Regul. 22:27–55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference. In the Schemes which follow: $R^1$ is shown as a $CF_3$ group, but could be any one of the presently described $R^1$ groups; G represents $R^3$, $R^{3a}$, $R^{3b}$, or $R^{3c}$ or any combination of these groups.

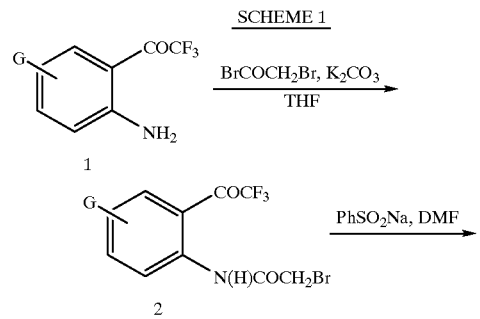

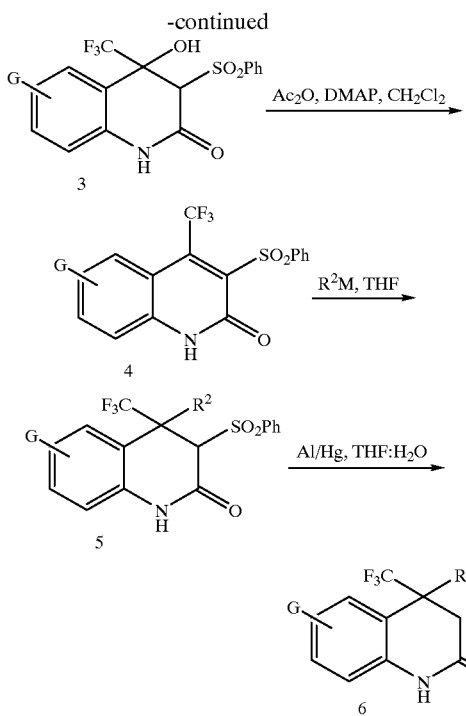

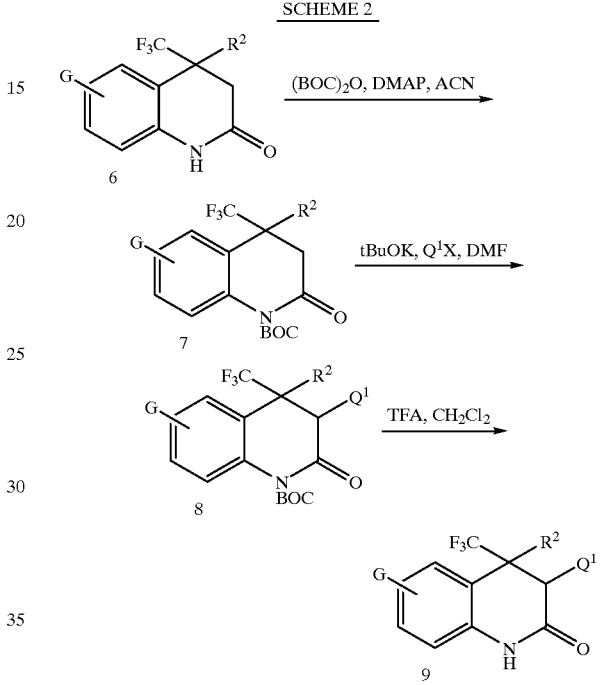

Scheme 1 illustrates a method for the preparation of 4,4-disubstituted quinolin-2-ones, 6, starting with an appropriately substituted 2-amino-trifluoromethylketone, 1. Acylation with bromoacetyl bromide followed by the treatment of the halide by benzene sulfinate provides for a ring closed compound in one step via displacement followed by ring closure. Acylation of the tertiary alcohol, 3, followed by elimination by base provides for a sulfone of formula 4. This compound can be reacted readily with organometallics to introduce the $R^2$ group. Lastly the sulfone moiety, 5, can be reductively removed, for example, by using aluminum amalgam.

example, tetrahydronaphthyridinones, tetrahydropyrido[3,4-b]-pyridinones, tetrahydropyrido[3,2-b]-pyridinones, and tetrahydropyrido[4,3-b]-pyridinones. An appropriately substituted amino-ketone 1n can be acylated and the resulting amide cyclized in the presence of benzenesulfinate to give alcohol 3n. Dehydration with base provides the α,β-unsaturated ketone 4n which can be modified via a lithium or grignard reagent to give 5n. Sulfone reduction can be achieved with Al/Hg or other known methods of reduction to provide 6n.

Scheme 2 illustrates methodology for the introduction of alkyl groups, $Q^1$, onto the C-3 carbon of the quinolin.-2-

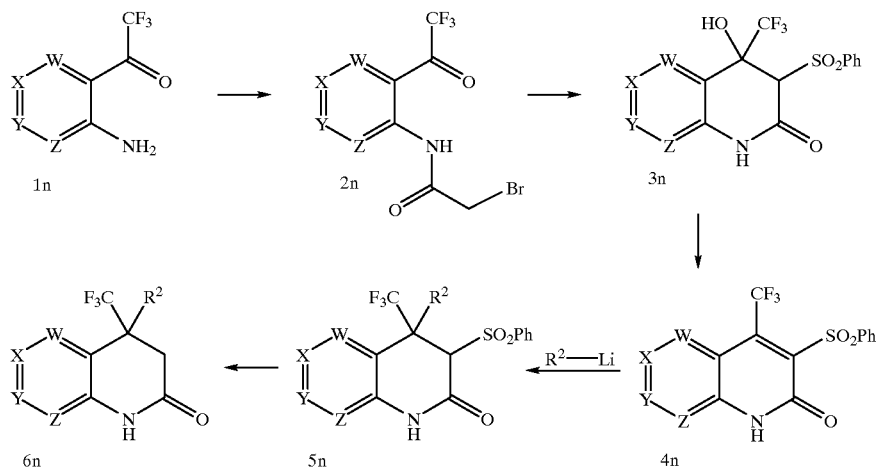

Scheme 1a illustrates a method, analogous to Scheme 1, of making derivatives to tetrahydroquinolinone compounds of formula 6 wherein W, X, Y, and/or Z are nitrogen; for ones. Treatment of the protected compound of formula 7 with base followed by a variety of alkylating agents, $Q^1X$, provides the protected compounds, 8, which can subsequently be deprotected using acidic reaction conditions to provide compounds 9.

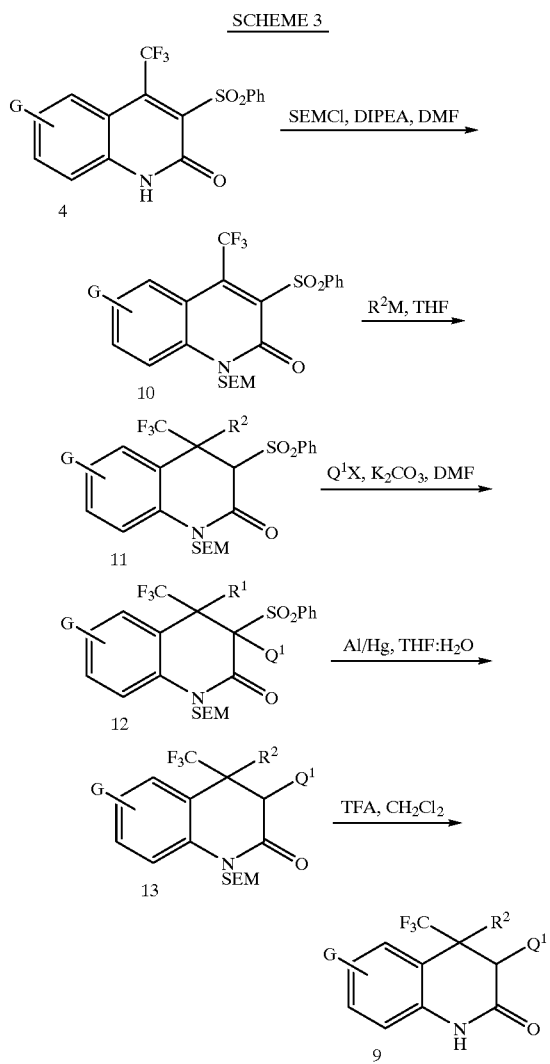

SCHEME 3

Alternatively, alkyl groups can also be introduced using an earlier intermediate in the synthetic sequence. Compound of formula 10 can be treated with base followed by an alkylating agent. The product upon treatment with aluminum amalgam for the removal of the sulfone functionality followed by deprotection provides compounds of formula 9.

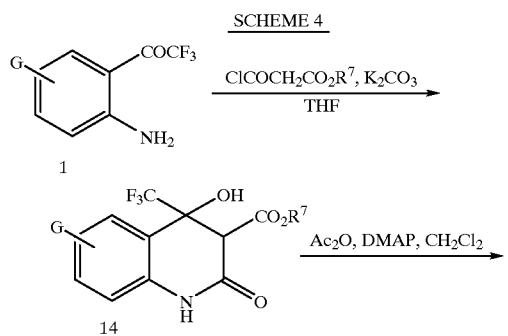

SCHEME 4

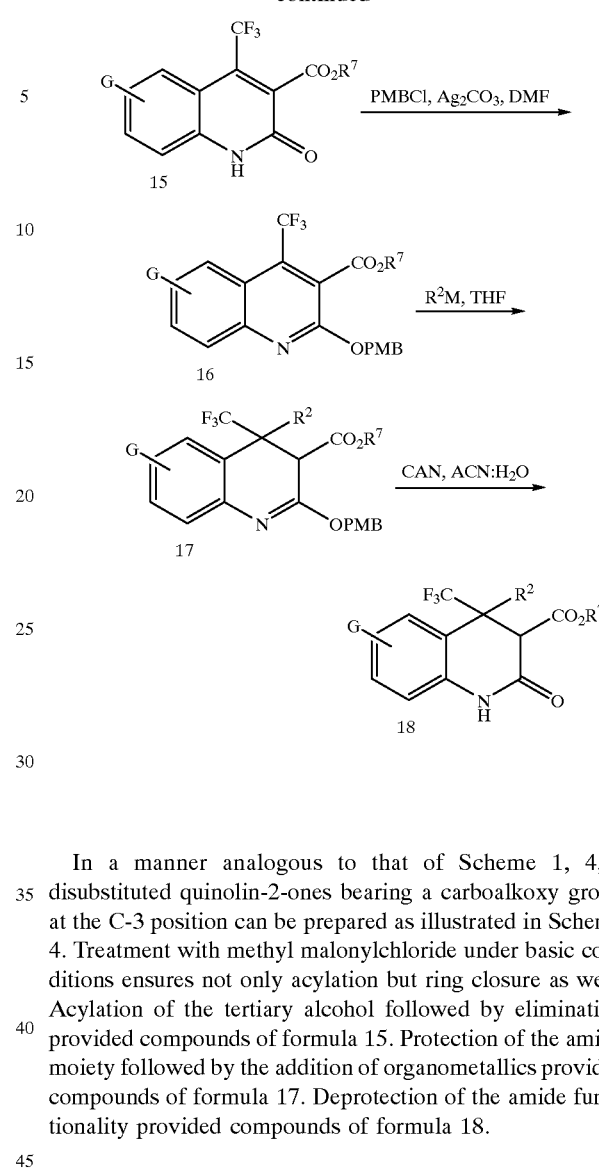

In a manner analogous to that of Scheme 1, 4,4-disubstituted quinolin-2-ones bearing a carboalkoxy group at the C-3 position can be prepared as illustrated in Scheme 4. Treatment with methyl malonylchloride under basic conditions ensures not only acylation but ring closure as well. Acylation of the tertiary alcohol followed by elimination provided compounds of formula 15. Protection of the amide moiety followed by the addition of organometallics provides compounds of formula 17. Deprotection of the amide functionality provided compounds of formula 18.

SCHEME 5

-continued

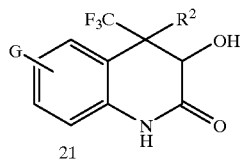

Scheme 5 illustrates methodology for the introduction of oxygen bearing moiety at the C-3 position of the 4,4-disubstituted quinolin-2-ones. Treatment of an appropriately protected quinolinone with base followed by an agent such as MoOPH allows for the introduction of the hydroxyl functionality.

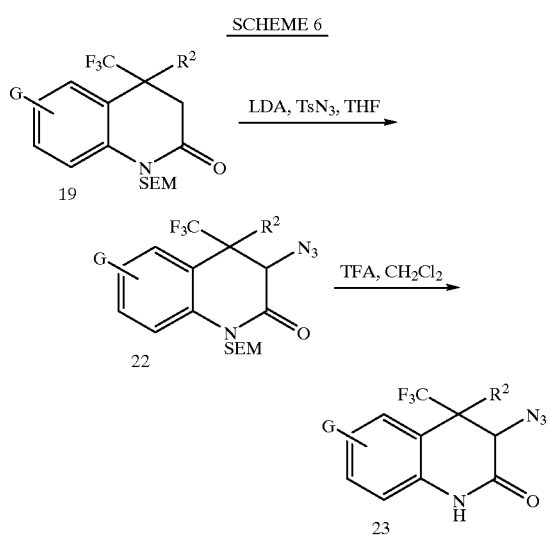

Scheme 6 illustrates methodology for the introduction of nitrogen bearing moiety at the C-3 position of the 4,4-disubstituted quinolin-2-ones. Treatment of an appropriately protected quinolinone with base followed by an agent such as tosyl azide allows for the transfer of the azide group onto the C-3 postion which can be subsequently reduced to an amine by routes such as the those represented by the Staudinger reaction.

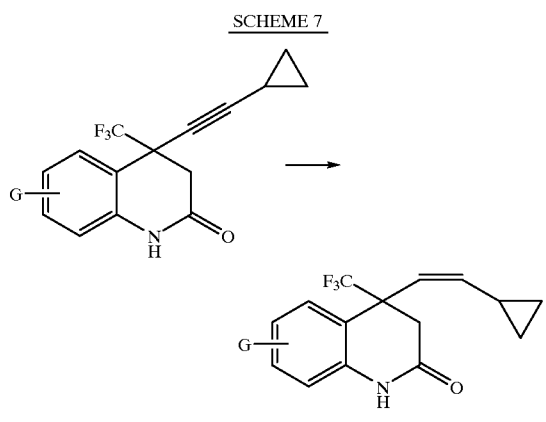

Scheme 7 illustrates a method of reducing acetylenes to cis-olefins using $NH_2OSO_3H$ and DIPEA. The conversion of the acetylenes to cis-olefins could also be effected by treatment with Raney Nickel and hydrazine. Trans-olefins are available by methods known to one of skill in theart for isomerization of the cis-olefins. Other methods known to reduce alkynes to alkenes could also be used.

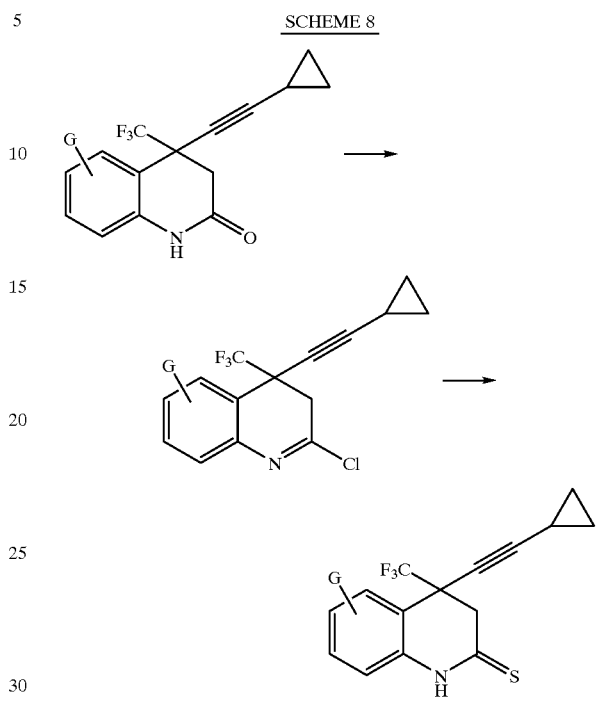

Thioamides of the present invention can be formed as shown in Scheme 8 from their corresponding amides. The amide is initially converted into a halo-imine via a chlorinating agent such as $POCl_3$ which is then further transformed into a thioamide with $NH_2C(S)NH_2$.

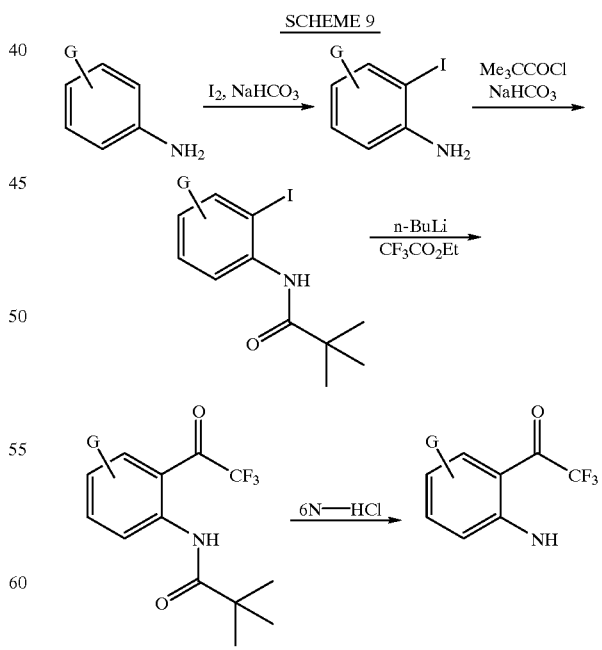

Scheme 9 describes a means of obtaining an aminoketone used as described above. After iodination of an appropriate aniline, the trifluoromethyl group can be introduced using a strong base and ethyl trifluoroacetate. Alternatively, Scheme 9 describes a means for obtaining an amino-ketone wherein $R^1$ could be any one of the presently described $R^1$ alkyls groups in addition to trifluoromethyl, for example, pentafluoroethyl, pentachloroethyl, heptafluoropropyl, etc, by using the appropriate ethyl haloaklylacetate in the above reaction.

SCHEME 9A

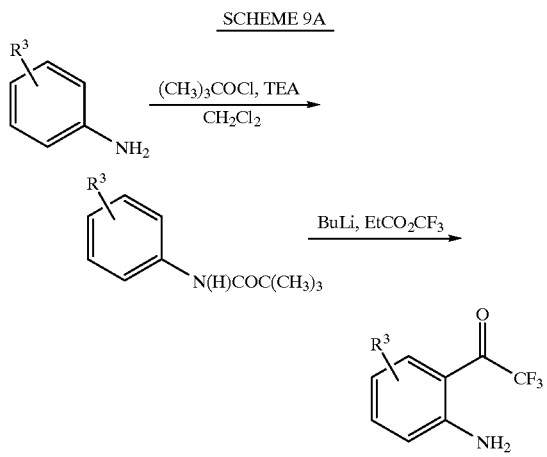

Scheme 9A describes an alternate route to ketone substituted anilines from a substituted aniline, wherein the aniline is protected, ester addition is accomplished using a strong base and the amine protecting group is subsequently removed.

SCHEME 10

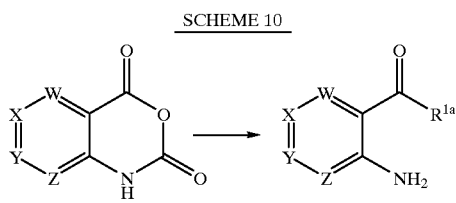

In addition to the methods of obtaining keto-anilines described previously, nucleophilic opening of isatoic anhydrides can also be used as shown in Scheme 10. This reaction is accomplished by using an anionic nucleophile of the group $R^{1a}$. See Mack et al, *J. Heterocyclic Chem.* 1987, 24, 1733–1739; Coppola et al, *J. Org. Chem.* 1976, 41(6), 825–831; Takimoto et al, *Fukuoka Univ. Sci. Reports* 1985, 15(1), 37–38; Kadin et al, *Synthesis* 1977, 500–501; Staiger et al, *J. Org. Chem.* 1959, 24, 1214–1219.

One enantiomer of a compound of Formula (I) may display superior activity compared with the other. Thus, the following stereochemistries are considered to be a part of the present invention.

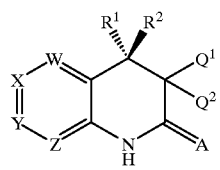

(Ia)

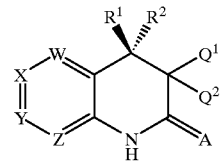

(Ib)

When required, separation of the racemic material can be achieved by HPLC using a chiral column as exemplified in Examples 27–34 (Scheme 4) or by a resolution using a resolving agent such as camphonic chloride as in Thomas J. Tucker, et al, *J. Med. Chem.* 1994, 37, 2437–2444. A chiral compound of Formula (I) may also be directly synthesized using a chiral catalyst or a chiral ligand, e.g. Mark A. Huffman, et al, *J. Org. Chem.* 1995, 60, 1590–1594.

Other features of the invention will become apparent in the course of the following descriptions of exemplary embodiments which are given for illustration of the invention and are not intended to be limiting thereof.

EXAMPLES

Abbreviations used in the Examples are defined as follows: "° C." for degrees Celsius, "d" for doublet, "dd" for doublet of doublets, "eq" for equivalent or equivalents, "g" for gram or grams, "mg" for milligram or milligrams, "mL" for milliliter or milliliters, "H" for hydrogen or hydrogens, "hr" for hour or hours, "m" for multiplet, "M" for molar, "min" for minute or minutes, "MHz" for megahertz, "MS" for mass spectroscopy, "nmr" or "NMR" for nuclear magnetic resonance spectroscopy, "t" for triplet, "TLC" for thin layer chromatography, "Al/Hg" for aluminum amalgam, "$Ac_2O$" for acetic anhydride, "ACN" for acetonitrile, "$(BOC)_2O$" for di-tert-butyl dicarbonate, "CAN" for ceric ammonium nitrate, "CDI" for carbonyl diimidazole, "cycPr" for cyclopropyl, "DIPEA" for diisopropylethylamine, "DMAP" for dimethylaminopyridine, "DME" for dimethoxyethane, "EDAC" for 1-(3-dimethylaminopropyl)-3-ethylcarbodiimide hydrochloride, "LAH" for lithium aluminium hydride, "LDA" for lithium diisopropylamide, "MoOPH" for oxo-diperoxy-molybdenum(pyridine) (hexamethylphosphoric triamide), "PMBCl" for 4-methoxybenzyl chloride, "SEMCl" for 2-(trimethylsilyl)-ethoxymethyl chloride, "TBAF" for tetrabutylammonium fluoride, "TBS-Cl" for t-butyldimethylsilyl chloride, and "TEA" for triethylamine.

Example 1

6-Chloro-4-(2-cyclopropylethynyl)-3,4-dihydro-4-(trifluoromethyl)-2(1H)-quinalinone

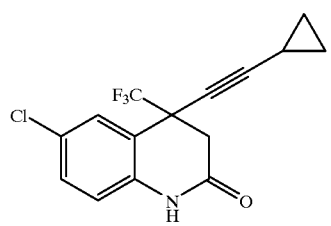

Step A: Preparation of compound of formula 2 wherein G=Cl

To a solution of amino ketone of formula 1 (3.02 g, 13.54 mmol) in THF (55 mL) at room temperature was added potassium carbonate (4.67 g, 33.85 mmol) followed by bromoacetyl bromide (1.5 mL, 16.93 mmol) and the resulting reaction mixture was allowed to stir at room temperature for 3 hours. The reaction mixture was poured onto water and extracted with ethyl acetate (3×100 mL). The combined ethyl acetate extracts were dried over anhydrous $Na_2SO_4$ and concentrated in vacuo to provide compound of formula 2 as a yellow oil. This product was used in the next step of the synthetic sequence without further purification.

Step B: Preparation of compound of formula 3 wherein G=Cl

To a solution of the bromide of formula 2 (crude product, 13.54 mmol) in DMF (55 mL) at room temperature was added sodium benzenesulfinate (4.44 g, 27.08 mmol) and the resulting reaction mixture was allowed to stir at room temperature for 18 hours. The reaction mixture was poured onto water and extracted with ethyl acetate (3×100 mL). The combined ethyl acetate extracts were dried over anhydrous $Na_2SO_4$ and concentrated in vacuo. The residue is triturated with hexanes (1 L) and dried in vacuo to provide 4.88 g of compound of formula 3, (5.49 g theoretical, 89%). $^1$H NMR (300 MHz, DMSO-$d_6$) δ 11.0(br s, 1H), 7.96(s, 1H), 7.76(d, 2H, J=8 Hz), 7.66(m, 1H), 7.51(m, 2H), 7.44(s, 1H), 7.33(m, 1H), 6.82(d, 1H, J=8 Hz), 4.47(s, 1H). $^{19}$F NMR (282 MHz, DMSO-$d_6$) δ −80.99(s, 3F). High resolution mass spec: calculated for $C_{16}H_{11}NO_4F_3ClS(M+H)^+$: 405.0042, found 405.0049.

Step C: Preparation of compound of formula 4 wherein G=Cl

To a slurry of the tertiary alcohol of formula 3 (6.815 g, 16.83 mmol) in methylene chloride (100 mL) at room temperature was added 4-(dimethylamino)pyridine (4.11 g, 33.65 mmol) followed by acetic anhydride (3.5 mL, 37.03 mmol) and the resulting reaction mixture is allowed to stir at room temperature for 18 hours. The reaction mixture was poured onto water and extracted with ethyl acetate (3×100 mL). The ethyl acetate extracts were washed with saturated $NaHCO_3$ and dried over anhydrous $Na_2SO_4$ and concentrated in vacuo. The residue is triturated with hexanes (1 L) and dried in vacuo to provide 6.06 g of compound of formula 4, (6.51 g theoretical, 93%). Anal. ($C_{16}H_9NO_3F_3ClS$) Calcd. C, 49.56; H, 2.349; N, 3.61; Cl, 9.14; F, 14.70; S, 8.279; Found. C, 49.26; H, 2.68; N, 3.30; Cl, 9.23; F, 14.49; S, 8.13.

Step D: Preparation of compound of formula V wherein G=Cl, $R^1$=cyclopropylacetylene To a solution of cyclopropylacetylene (153 μL, 1.16 mmol) in THF (4 mL) at 0° C. was added nBuLi (0.65 mL, 1.04 mmol) and the resulting reaction mixture was allowed to stir at 0° C. for 30 minutes. Thereafter the reaction mixture was cannulated to stirred solution of sulfone of formula 4 (100 mg, 0.26 mmol) in THF (2 mL) at −78° C. The dry ice bath is removed and the reaction mixture is stirred for an additional hour. The reaction mixture is poured onto saturated $NH_4Cl$ and extracted with ethyl acetate (3×25 mL) and the combined ethyl acetate extracts were dried over anhydrous $Na_2SO_4$ and concentrated in vacuo. Chromatography ($SiO_2$, 30% EtOAc-hexanes eluant) provided 33 mg of compound of formula 5, (117 mg theoretical, 28%). $^1$H NMR (300 MHz, CDCl$_3$) δ 9.2(br s, 1H), 7.9(m, 1H), 7.65(m, 1H), 7.55(m, 2H), 7.45(m, 2H), 7.25(m, 1H), 6.8(m, 1H), 4.45(s, 1H), 1.4(m, 1H), 0.9(m, 4H). High resolution mass spec: calculated for $C_{21}H_{16}NO_3F_3SCl$ $(M+H)^+$: 454.0492; found: 454.0475.

Step E:

To a solution of sulfone of formula 5 (29 mg, 0.044 mmol) in THF:water (9:1, 2 mL) at room temperature was added Al/Hg amalagam (prepared from aluminum foil (230 mg) and $HgCl_2$ (1.5 g) in water (30 mL) and the resulting reaction mixture was allowed to stir at reflux for one hour. The reaction mixture was filtered through Celite and the filterate concentrated in vacuo. Chromatography ($SiO_2$, 30% EtOAc-hexanes eluant) provided 11 mg of the title compound, (13.8 mg theoretical, 80%). $^1$H NMR (300 MHz, CDCl$_3$) δ 8.95(br s, 1H), 7.65(m, 1H), 7.3(m, 1H), 6.8(m, 1H), 3.0(dd, J=17 Hz, 17Hz, 2H), 1.35(m, 1H), 0.9(m, 4H). $^{19}$F NMR (282 MHz, CDCl$_3$) δ −76.66(s, 3F). Anal. ($C_{15}H_{11}NOF_3Cl$) Calcd. C, 57.43; H, 3.53; N, 4.475; F, 18.17; Cl, 11.30; Found. C, 57.40; H, 3.44; N, 4.34; F, 17.92; Cl, 11.36.

Example 2

6-Chloro-4-(2-cyclopropylethynyl)-3,4-dihydro-3-methoxycarbonyl-4-(trifluoromethyl)-2(1H)-quinalinone

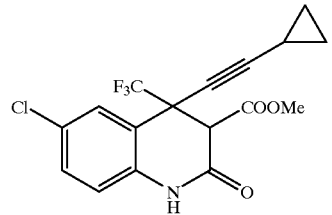

Step A: Preparation of compound of formula 14 wherein G=Cl and $R^2$=methyl

To a solution of amino-ketone 1 (5.2 g, 23.32 mmol) in DMF (100 mL) at room temperature was added $K_2CO_3$ (8.045 g, 58.3 mmol) followed by methyl malonylchloride (3.14 mL, 29.15 mmol) and the resulting reaction mixture was allowed to stir at room temperature for 4 hours. The reaction mixture was poured onto water and extracted with EtOAc (3×100 mL) and the combined EtOAc extracts were dried over anhydrous $Na_2SO_4$ and concentrated in vacuo. The residue was triturated with hexanes to provide 14.63 g compound of formula 14, (15.06 g theoretical, 96%). $^1$H NMR (300 MHz, DMSO-$d_6$) d 10.92(br s, 1H), 7.8(br s, 1H), 7.5(m, 1H), 7.4(m, 1H), 6.95(m, 1H), 3.58(s, 3H), 3.8(s, 1H). $^{19}$F NMR (282 MHz, DMSO-$d_6$) δ −81.69(s, 3F). Anal. ($C_{12}H_9NO_4F_3Cl$) Calcd. C, 44.53; H, 2.80; N, 4.337; F, 17.61; Cl, 10.95; Found. C, 44.51; H, 2.99; N, 4.19; F, 17.354; Cl, 11.15.

Step B: Preparation of compound of formula 15 wherein G=Cl and $R^2$=methyl

To a solution of of compound of formula 14 (14.58 g, 45.14 mmol), in $CH_2Cl_2$ (200 mL) at room temperature was added DMAP (11.015 g, 90.28 mmol) followed by $Ac_2O$ (9.4 mL, 99.31 mmol) and the resulting reaction mixture was allowed to stir at room temperature for 14 hours. The reaction mixture was poured onto 10% citric acid and extracted with $CH_2Cl_2$ (3×100 mL) and the combined $CH_2Cl_2$ extracts were washed with saturated $NaHCO_3$, dried over anhydrous $Na_2SO_4$ and concentrated in vacuo to provide 13.32 g of compound of formula 15, 13.77 g, theoretical, 97%). $^1$H NMR (300 MHz, DMSO-$d_6$) δ 12.94 (br s, 1H), 7.8(m, 1H), 7.65(m, 1H), 7.45(m, 1H), 3.83(s, 3H). $^{19}$F NMR (282 MHz, DMSO-$d_6$) δ −59.15(s, 3F). Anal. ($C_{12}H_7NO_3F_3Cl$) Calcd. C, 47.16; H, 2.318; N, 4.58; F, 18.65; Cl, 11.60; Found. C, 47.22; H, 2.36; N, 4.57; F, 18.29; Cl, 11.85.

Step C: Preparation of compound of formula 16 wherein G=Cl and $R^2$=methyl

To a solution of compound of formula 15 (10 mg, 0.32 mmol) in DMF (2 mL) at room temperature was added Ag$_2$CO$_3$ (265 mg, 0.96 mmol) followed by PMBCl (57 μL, 0.42 mmol) and the resulting reaction mixture was allowed to stir at room temperature for 14 hours. The reaction mixture was filtered through Celite and the filterate washed with water. The combined organic layers were dried over anhydrous Na$_2$SO$_4$ and concentrated in vacuo. Chromatography (SiO$_2$, 10% EtOAc-hexanes eluant) provided 105 mg of compound of formula 16, (136 mg theoretical, 77%). $^1$H NMR (300 MHz, CDCl$_3$) δ 8.0(m, 1H), 7.85(M, 1H), 7.65(m, 1H), 7.4(d, J=9 Hz, 2H), 6.9(d, J=9 Hz, 2H), 5.5(s, 2H), 9.95(s, 3H), 3.8(s, 3H). $^{19}$F NMR (282 MHz, CDCl$_3$) δ −58.37(s, 3F).

Step D: Preparation of compound of formula 17 wherein G=Cl, R$^1$=cyclopropylacetylene and R$^2$=methyl To a solution of cyclopropylacetylene (565 μL, 4.28 mmol) in THF (12 mL) at 0° C. was added nBuLi (2.38 mL, 3.8 mmol) and the resulting reaction mixture was allowed to stir at 0° C. for 30 minutes. Thereafter the reaction mixture was cannulated to stirred solution of sulfone of formula 16 (405 mg, 0.95 mmol) in THF (6 mL) at −78° C. The dry ice bath is removed and the reaction mixture is stirred for an additional hour. The reaction mixture is poured onto saturated NH$_4$Cl and extracted with ether (3×25 mL) and the combined ether extracts were dried over anhydrous Na$_2$SO$_4$ and concentrated in vacuo. Chromatography (SiO$_2$, 15% CH$_2$Cl$_2$-hexanes eluant) provided 220 mg of compound of formula 17, (465 mg theoretical, 47%). $^1$H NMR (300 MHz, CDCl$_3$) δ 7.8(m, 1H), 7.35(m, 2H), 7.2(d, J=9 Hz, 2H), 6.85(d, J=9 Hz, 2H), 5.3(dd, J=10, 12 Hz, 2H), 3.8(s, 3H), 3.6(s, 3H), 1.35(m, 1H), 0.9(m, 2H), 0.75(m, 2H). $^{19}$F NMR (282 MHz, CDCl$_3$) δ −77.03(s, 3F). Mass spec. (-ES): 490(M−H)$^+$ (80%), 370 (100%).

Step E:

To a solution of PMB protected quinolinone of formula 17 (30 mg, 0.061 mmol) in ACN:water (9:1, 1 mL) at room temperature was added CAN (167 mg, 0.3 mmol) and the resulting reaction mixture was allowed to stir at room temperature for 30 minutes. The reaction mixture was poured onto water and extracted with EtOAc (3×25 mL) and the combined EtOAc extracts were dried over anhydrous Na$_2$SO$_4$ and concentrated in vacuo. Chromatography (SiO$_2$, 20% EtOAc-hexanes eluant) provided 20 mg of the title compound, (22 mg theoretical, 91%). $^1$H NMR (300 MHz, CDCl$_3$) δ 9.12(br s, 1H), 7.6(m, 1H), 7.35(m, 1H), 6.6(m, 1H), 4.0(s, 2H), 3.75(s, 3H), 1.35(m, 1H), 0.85(m, 2H), 0.75(m, 2H). $^{19}$F NMR (282 MHz, CDCl$_3$) δ −76.22(s, 3F). High resolution mass spec: calculated for C$_{16}$H$_{13}$NOF$_3$Cl (M−H)$^+$: 370.0458, found 370.0473.

Example 3

6-Chloro-4-(2-cyclopropylethynyl)-3,4-dihydro-3-methyl-4-(trifluoromethyl)-2(1H)-quinalinone

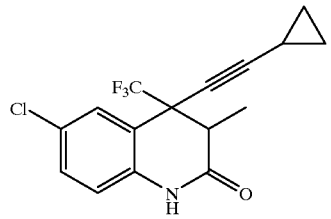

Step A: Preparation of compound of formula 10 wherein G=Cl

To a solution of quinolinone of formula 4 (4.12 g, 10.6 mmol) in DMF (40 mL) at room temperature was added DIPEA (3.15 mL, 18 mmol) followed by SEMCl (2.26 mL, 12.8 mmol) and the resulting reaction mixture is allowed to stir at room temperature for 14 hours. The reaction mixture was poured onto 1N HCl and extracted with ether (2×100 mL) and the combined ether extracts were dried over anhydrous Na$_2$SO$_4$ and concentrated in vacuo. Chromatography (SiO$_2$, 15% EtOAc-hexanes eluant) provided 5.47 g of compound of formula 10, (5.49 g theoretical, 83%). $^1$H NMR (300 MHz, CDCl$_3$) δ 8.25(m, 2H), 8.05(m, 1H), 7.75–7.55(m, 5H), 5.65(s, 2H), 3.53(t, J=8 Hz, 2H), 0.91(t, J=8 Hz, 2H), 0.01(s, 9H). $^{19}$F NMR (282 MHz, CDCl$_3$) δ −51.70(s, 3F). Mass spec. (NH$_3$—CI): 518(M+H)$^+$ (100%).

Step B: Preparation of compound of formula 11 wherein G=Cl, R$^1$=cyclopropylacetylene To a solution of cyclopropylacetylene (232 μL, 1.76 mmol) in THF (6 mL) at 0° C. was added nBuLi (0.98 mL, 1.56 mmol) and the resulting reaction mixture was allowed to stir at 0° C. for 30 minutes. Thereafter the reaction mixture was cannulated to stirred solution of sulfone of formula 10 (200 mg, 0.39 mmol) in THF (3 mL) at −78° C. The dry ice bath is removed and the reaction mixture is stirred for an additional hour. The reaction mixture is poured onto saturated NH$_4$Cl and extracted with ether (3×25 mL) and the combined ether extracts were dried over anhydrous Na$_2$SO$_4$ and concentrated in vacuo. Chromatography (SiO$_2$, 30% EtOAc-hexanes eluant) provided 153 mg of compound of formula 11, (228 mg theoretical, 67%). $^1$H NMR (300 MHz, CDCl$_3$) δ 7.85(m, 2H), 7.65(m, 2H), 7.5(m, 2H), 7.35(m, 2H), 5.59(d, J=11 Hz, 1H), 4.94(d, J=11 Hz, 1H), 4.6(s, 1H), 3.75(m, 1H), 3.6(m, 1H), 1.3(m, 1H), 0.95(m, 2H), 0.85(m, 4H), 0.00(s, 9H). Mass spec. (ES-): 582(M−H)$^+$ (100%).

Step C: Preparation of compound of formula 12 wherein G=Cl, R$^1$=cyclopropylacetylene and R$^2$=methyl To a solution of sulfone-quinolinone of formula 11 (153 mg, 0.26 mmol) in DMF (1.5 mL) at room temperature was added K$_2$CO$_3$ (180 mg, 1.3 mmol) followed by methyl iodide (40 μl, 0.65 mmol) and the resulting reaction mixture was allowed to stir at room temperature for 14 hours. The reaction mixture is poured onto water and extracted with ether (3×50 mL) and the combined ether extracts were dried over anhydrous MgSO$_4$ and concentrated in vacuo. Chromatography (SiO$_2$, 10% EtOAc-hexanes eluant) provided 111 mg of compound of formula 12 as mixture of diastreomers, (155 mg theoretical, 72%). $^1$H NMR (300 MHz, CDCl$_3$) δ 8.4(m, 2H), 8.0(m, 1H), 7.9–7.4(m, 13H), 5.8(d, J=11 Hz, 1H), 5.6(d, J=11 Hz, 1H), 5.1(d, J=11 Hz, 1H), 5.0(d, J=11 Hz, 1H), 4.0–3.6(m, 6H), 2.2(m, 3H), 1.8(s, 3H), 1.6(m, 1H), 1.05–0.85(m, 13H), 0.2(s, 9H), 0.00(s, 9H). $^{19}$F NMR (282 MHz, CDCl$_3$) δ −60.95(s, 3F, 35%), −66.65 (s, 3F, 100%). Mass spec. (NH$_3$—CI): 615(M+NH$_4$$^+$, 100%).

Step D: Preparation of compound of formula 13 wherein G=Cl, R$^1$=cyclopropylacetylene and R$^2$=methyl To a solution of sulfone of formula 12 (111 mg, 0.19 mmol) in THF:water (9:1, 2.5 mL) at room temperature was added Al/Hg amalagam (prepared from aluminum foil (160 mg) and HgCl$_2$ (1 g) in water (25 mL) and the resulting reaction mixture was allowed to stir at reflux for two hours. The reaction mixture was filtered through Celite and the filterate concentrated in vacuo. Chromatography (SiO$_2$, 10% EtOAc-hexanes eluant) provided 36 mg of compound of formula 13, (87 mg theoretical, 41%). $^1$H NMR (300 MHz, CDCl$_3$) δ 7.7(m, 1H), 7.4(m, 2H), 5.65(d, J=11 Hz, 1H), 5.0(d, J=11 Hz, 1H), 3.6 (m, 2H), 3.0(m, 1H), 1.6(m, 3H), 1.4(m, 1H), 0.95(m, 2H), 0.9(m, 2H), 0.8(m, 2H), 0.00(s, 9H). $^{19}$F NMR (282 MHz, CDCl$_3$) δ −69.53(s, 3F). Mass spec. (NH₃—CI): 458 (M+H)⁺ (42%), 430 (100%), 328(M-SEM+H⁺, 47%).

Step E:

To a solution of SEM protected quinolinone of formula 13 (36 mg, 0.079 mmol) in CH₂Cl₂ (1 mL) was added TFA (1 mL) and the resulting reaction mixture was allowed to stir at room temperature for 20 minutes. The reaction mixture was poured onto saturated NaHCO₃ and extracted with CH₂Cl₂ (3×25 mL) and the combined CH₂Cl₂ extracts were dried over anhydrous Na₂SO₄ and concentrated in vacuo. The residue was taken up in MeOH (1 mL) and 15% NaOH (1 mL) was added to the reaction, and the resulting reaction mixture was allowed to stir at room temperature for 10 minutes. The reaction mixture was poured onto water and extracted with CH₂Cl₂ (3×25 mL) and the combined CH₂Cl₂ extracts were dried over anhydrous Na₂SO₄ and concentrated in vacuo. Chromatography (SiO₂, 20% EtOAc-hexanes eluant) provided 14 mg of the title compound, (26 mg theoretical, 53%). $^1$H NMR (300 MHz, CDCl₃) δ 8.65 (br s, 1H), 7.7(m, 1H), 7.3(m, 1H), 6.8(m, 1H), 3.0(m, 1H), 1.55(m, 3H), 1.4(m, 1H), 0.9(m, 2H), 0.8(m, 2H). $^{19}$F NMR (282 MHz, DMSO-d₆) δ −69.59(s, 3F). High resolution mass spec: calculated for C₁₆H₁₃NOF₃Cl(M+H)⁺: 328.0716, found 328.0706.

Example 4

3-Allyl-6-chloro-4-(2-cyclopropylethynyl)-3,4-dihydro-4-(trifluoromethyl)-2(1H)-quinalinone

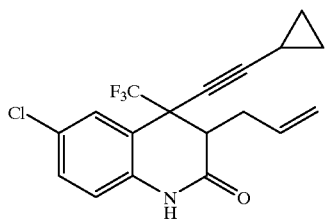

Step A: Preparation of compound of formula 7 wherein G=Cl and R¹=cyclopropylacetylene To a solution of quinolinone of formula 6 (600 mg, 1.92 mmol) in ACN (6 mL) at room temperature was added DMAP (350 mg, 2.88 mmol) followed by (BOC)₂O (1050 mg, 4.81 mmol) and the resulting reaction mixture was allowed to stir at room temperature for 2 hours. The reaction mixture was poured onto 10% citric acid and extracted with EtOAc (2×50 mL) and the combined EtOAc extracts were dried over anhydrous Na₂SO₄ and concentrated in vacuo. Chromatography (SiO₂, 5 to 10% EtOAc-hexanes eluant) provided 730 mg of compound of formula 7, (792 mg theoretical, 92%). $^1$H NMR (300 MHz, CDCl₃) δ 7.7(m, 1H), 7.35(m, 1H), 6.9(m, 1H), 3.1(dd, J=17 Hz, 17 Hz, 2H), 1.6(s, 9H), 1.35(m, 1H), 0.85(m, 2H), 0.75(m, 2H). $^{19}$F NMR (282 MHz, CDCl₃) δ −75.91 s, 3F). High resolution mass spec: calculated for C₂₀H₁₈N₂O₃F₃ (M+H)⁺: 412.0927; found: 412.0950.

Step B: Preparation of compound of formula 8 wherein G=Cl and R¹=cyclopropylacetylene and R²=allyl To a solution of the BOC protected quinolinone of formula 7 (90 mg, 0.22 mmol) in DMF 92 mL) at room temperature was added ᵗBuOK in THF (0.33 mL, 0.33 mmol) followed by allyl iodide (40 μL, 0.44 mmol) and the resulting reaction mixture was allowed to stir at room temperature for 24 hours. The reaction mixture was poured onto water and extracted with EtOAc (2×50 mL) and the combined EtOAc extracts were dried over anhydrous Na₂SO₄ and concentrated in vacuo. Chromatography (SiO₂, 10% EtOAc-hexanes eluant) provided 56 mg of compound of formula 8, (100 mg theoretical, 56%). $^1$H NMR (300 MHz, CDCl₃) δ 7.75(m, 1H), 7.3(m, 1H), 6.85(m, 1H), 5.7(m, 1H), 5.0(m, 1H), 3.2–2.7(m, 1H), 2.1(m, 1H), 1.55(s, 9H). 1.4(m, 1H), 0.85(m, 2H), 0.8(m, 2H). $^{19}$F NMR (282 MHz, CDCl₃) δ −75.18(s, 3F).

Step C:

To a solution of quinolinone of formula 8 (56 mg, 0.12 mmol) in CH₂Cl₂ (2 mL) at room temperature was added TFA (2 mL) at room temperature and the resulting reaction mixture was allowed to stir at room temperature for 15 minutes. The reaction mixture was poured onto saturated NaHCO₃ and extracted with EtOAc (2×50 mL) and the combined EtOAc extracts were dried over anhydrous Na₂SO₄ and concentrated in vacuo. Chromatography (SiO₂, 25% EtOAc-hexanes eluant) provided 31 mg of title compound, (42 mg theoretical, 74%). $^1$H NMR (300 MHz, CDCl₃) δ 8.85(br s, 1H), 7.6(m, 1H), 7.3(m, 1H), 6.8(m, 1H), 5.75(m, 1H), 5(m, 2H), 2.95(m, 1H), 2.8(m, 1H), 2.15(m, 1H), 1.4(m, 1H), 0.9(m, 4H). $^{19}$F NMR (282 MHz, CDCl₃) δ −75.68(s, 3F). High resolution mass spec: calculated for C₁₈H₁₆NOF₃Cl (M+H)⁺: 354.0873; found: 354.0861.

Example 5

6-Chloro-4-(2-cyclopropylethynyl)-3,4-dihydro-3-phenylmethyl-4-(trifluoromethyl)-2(H)-quinalinone

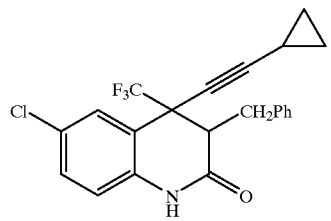

The title compound was prepared in a manner similar to the product of Example 4, except that in Step B benzyl bromide was used instead of allyl iodide: $^1$H NMR (300 MHz, CDCl₃) δ 9.69(br s, 1H), 7.6(m, 1H), 7.2(m, 1H), 7.15(m, 5H), 6.4(m, 1H), 3.4(m, 1H), 3.15(m, 1H), 2.65(m, 1H), 1.45(m, 1H), 0.9(m, 4H). $^{19}$F NMR (282 MHz, CDCl₃) δ −75.46(s, 3F). High resolution mass spec: calculated for C₂₂H₁₆NOF₃Cl (M–H)⁺:402.0872; found:402.0846.

Example 6

6-Chloro-4-(2-cyclopropylethynyl)-3,4-dihydro-3-isopropyl-4-(trifluoromethyl)-2(1H)-quinalinone

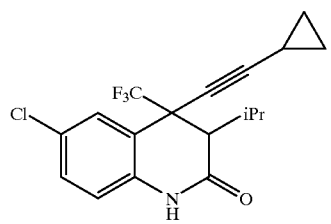

The title compound was prepared in a manner similar to the product of Example 4, except that in Step B isopropyl iodide was used instead of allyl iodide: $^1$H NMR (300 MHz, CDCl₃) δ 8.4(br s, 1H), 7.65(m, 1H), 7.25(m, 1H), 6.65(m, 1H), 2.8(m, 1H), 2.6(m, 1H), 1.4(m, 1H), 1.2(d, J=7 Hz, 3H), 0.9(m, 2H), 0.8(m, 2H), 0.6(d, J=7 Hz, 3H). $^{19}$F NMR (282 MHz, CDCl$_3$) δ −76.13(s, 3F). High resolution mass spec: calculated for C$_{18}$H$_{17}$NOF$_3$Cl (M+H)$^+$: 356.1029; found: 356.1016.

Example 7

5,6-Difluoro-4-(2-cyclopropylethynyl)-3,4-dihydro-4-(trifluoromethyl)-2(1H)-quinalinone

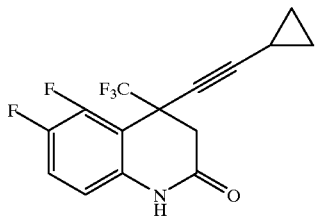

The title compound was prepared in a manner similar to the product of Example 1, except that in Step A 3,4-difluoro-2-trifluoroacetylaniline was used instead of 4-chloro-2-trifluoroacetylaniline: $^1$H NMR (300 MHz, DMSO-d$_6$) δ 10.6(br s, 1H), 7.45(m, 1H), 6.75(m, 1H), 3.35(d, J=17 Hz, 1H), 2.8(d, J=17 Hz, 1H), 1.4(m, 1H), 0.8(m, 2H), 0.6(m, 2H). $^{19}$F NMR (282 MHz, DMSO-d$_6$) δ −76.48(s, 3F), −134.81(s, 1F), −145.76(s, 1F). High resolution mass spec: calculated for C$_{15}$H$_{11}$NOF$_5$ (M−H)$^+$: 316.0739; found: 316.0760.

Example 8

6-Chloro-4-(2-cyclopropylethynyl)-3,4-dihydro-3-hydroxy-4-(trifluoromethyl)-2(1H)-quinalinone

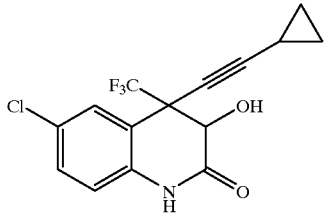

Step A: Preparation of compound of formula 19 wherein G=Cl and R$^1$=cyclopropylacetylene To a solution of sulfone of formula 11 (123 mg, 0.21 mmol) in THF:water (9:1, 2.5 mL) at room temperature was added Al/Hg amalagam (prepared from aluminum foil (160 mg) and HgCl$_2$ (1 g) in water (20 mL) and the resulting reaction mixture was allowed to stir at reflux for one hour. The reaction mixture was filtered through Celite and the filterate concentrated in vacuo. Chromatography (SiO$_2$, 10% EtOAc-hexanes eluant) provided 72 mg of compound of formula 19, (93 mg theoretical, 77%). $^1$H NMR (300 MHz, CDCl$_3$) δ 7.7(m, 1H), 7.4(m, 2H), 5.6(d, J=11 Hz, 1H), 5.1(d, J=11 Hz, 1H), 3.6(m, 2H), 3.15(m, 1H), 1.4(m, 1H), 0.95(m, 2H), 0.9(m, 2H), 0.85(m, 2H), 0.01(s, 9H). $^{19}$F NMR (282 MHz, CDCl$_3$) δ −76.15(s, 3F). Mass spec. (NH$_3$—Cl): 444(M+H)$^+$, 30%), 416 (100%).

Step B: Preparation of compound of formula 20 wherein G=Cl and R$^1$=cyclopropylacetylene To a solution of formula 19 (118 mg, 0.27 mmol) in THF (2 mL) at 0° C. was added LDA (0.2 mL, 0.4 mmol) followed by MOOPH (155 mg, 0.37 mmol) and the resulting reaction mixture was allowed to stir at room temperature (ice bath removed after the addition of reagents) for 14 hours. The reaction mixture was poured onto water and extracted with EtOAc (3×25 mL) and the combined EtOAc extracts were dried over anhydrous Na$_2$SO$_4$ and concentrated in vacuo. Chromatography (SiO$_2$, 5–20% EtOAc-hexanes eluant) provided 66 mg of compound of formula 20 as a mixture of isomers, (124 mg theoretical, 54%). $^1$H NMR (300 MHz, CDCl$_3$) δ 7.65(m, 1H), 7.4(m, 1H), 5.5(d, J=11 Hz, 1H), 5.25(m, J=11 Hz, 1H), 4.45(m, 1H), 3.65(m, 2H), 1.25(m, 1H), 0.95(m, 1H), 0.8(m, 2H), 0.65(m, 2H), 0.01(s, 9H). $^{19}$F NMR (282 MHz, CDCl$_3$) δ −69.64(s, 3F). High resolution mass spec: calculated for C$_{21}$H$_{26}$NO$_3$F$_3$ClSi(M+H)$^+$: 460.1323, found 460.1305.

Step C:

To a solution of SEM protected quinolinone of formula 20 (23 mg, 0.05 mmol) in CH$_2$Cl$_2$ (2 mL) was added TFA (2 mL) and the resulting reaction mixture was allowed to stir at room temperature for 20 minutes. The reaction mixture was poured onto saturated NaHCO$_3$ and extracted with CH$_2$Cl$_2$ (3×25 mL) and the combined CH$_2$Cl$_2$ extracts were dried over anhydrous Na$_2$SO$_4$ and concentrated in vacuo. The residue was taken up in MeOH (2 mL) and 15% NaOH (2 mL) was added to the reaction, and the resulting reaction mixture was allowed to stir at room temperature for 10 minutes. The reaction mixture was poured onto water and extracted with CH$_2$Cl$_2$ (3×25 mL) and the combined CH$_2$Cl$_2$ extracts were dried over anhydrous Na$_2$SO$_4$ and concentrated in vacuo. Chromatography (SiO$_2$, 40% EtOAc-hexanes eluant) provided 5 mg of the title compound as a mixture of isomers, (16 mg theoretical, 31%). $^1$H NMR (300 MHz, CDCl$_3$) 68.2(br s, 1H), 7.6(m, 1H), 7.35(m, 1H), 6.6(m, 1H), 4.45 (m, 1H), 3.45 (m, 1H), 1.3 (m, 1H), 0.85 (m, 2H), 0.75 (m, 2H). $^{19}$F NMR (282 MHz, CDCl$_3$) δ −70.75(s, 3F). High resolution mass spec: calculated for C$_{15}$H$_{12}$NO$_2$F$_3$Cl (M+H)$^+$: 330.0508, found 330.0495.

TABLE 1*

| Ex. # | G | R$^1$ | R$^2$ | Q$^1$ | (M + H)$^+$ |
|---|---|---|---|---|---|
| 1 | 6-Cl | —CF$_3$ | —C≡C-cycPr | —H | 314.0559 |
| 2 | 6-Cl | —CF$_3$ | —C≡C-cycPr | —COOCH$_3$ | 370.0473 |
| 3 | 6-Cl | —CF$_3$ | —C≡C-cycPr | —CH$_3$ | 328.0706 |
| 4 | 6-Cl | —CF$_3$ | —C≡C-cycPr | —CH$_2$CH=CH$_2$ | 354.0861 |
| 5 | 6-Cl | —CF$_3$ | —C≡C-cycPr | —CH$_2$Ph | 402.0846 |
| 6 | 6-Cl | —CF$_3$ | —C≡C-cycPr | —CH(CH$_3$) | 356.1016 |
| 7 | 5,6-diF | —CF$_3$ | —C≡C-cycPr | —H | 316.0739 |
| 8 | 6-Cl | —CF$_3$ | —C≡C-cycPr | —OH | 330.0495 |

*Unless otherwise indicated, stereochemisty is (+/−).

Tables 2 and 3 show representative compounds envisaged by the scope of the present invention. Each formula shown at the start of Table 2 and Table 3 is intended to be paired with each entry in the table which follows. Unless otherwise noted, the compounds represented in Table 2 and Table 3 have stereochemistry (+/−) and, in R$^2$, all double bonds are trans.

TABLE 2

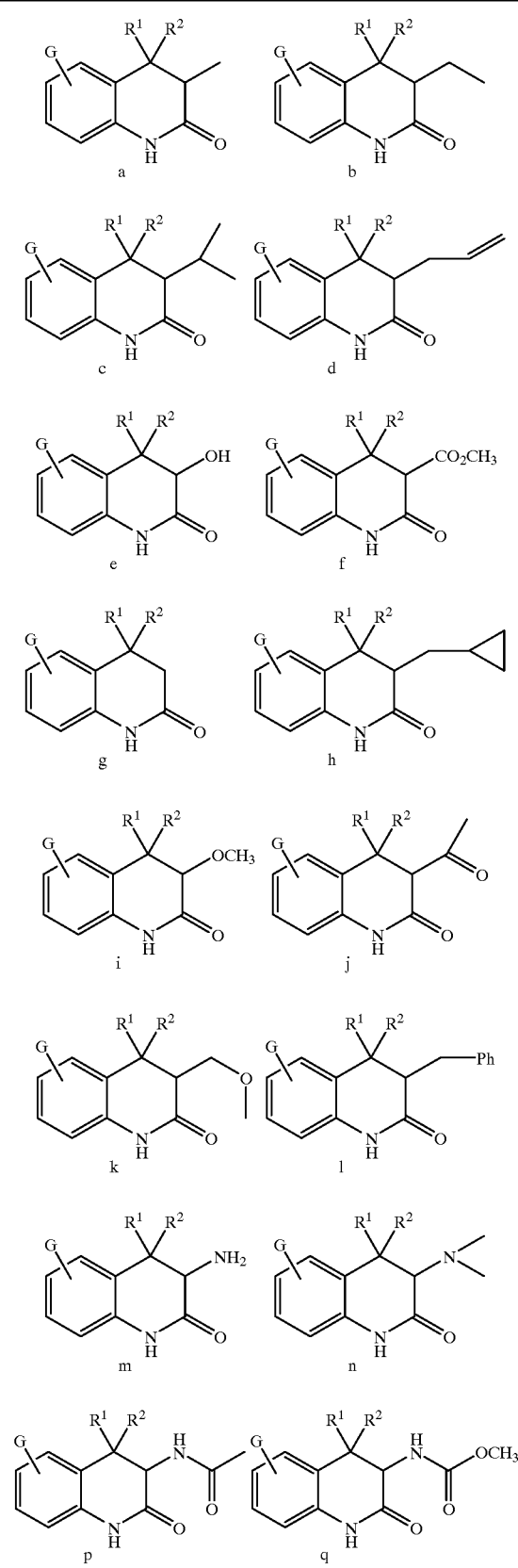

| Ex. # | G | R¹ | R² |
|---|---|---|---|
| 1001 | 5-Cl | $CF_3$ | $CH_2CH_2CH_3$ |
| 1002 | 5-Cl | $CF_3$ | $CH_2CH_2CH_2CH_3$ |
| 1003 | 5-Cl | $CF_3$ | $CH_2CH_2CH_2CH_2CH_3$ |
| 1004 | 5-Cl | $CF_3$ | $CH_2CH_2CH(CH_3)_2$ |
| 1005 | 5-Cl | $CF_3$ | $CH_2CH_2$-tBu |
| 1006 | 5-Cl | $CF_3$ | $CH_2$-cycPr |
| 1007 | 5-Cl | $CF_3$ | $CH_2$—Ph |
| 1008 | 5-Cl | $CF_3$ | $CH_2$-2-Pyridyl |
| 1009 | 5-Cl | $CF_3$ | $CH_2$-3-Pyridyl |
| 1010 | 5-Cl | $CF_3$ | $CH_2$-4-Pyridyl |
| 1011 | 5-Cl | $CF_3$ | $CH_2$-2-furanyl |
| 1012 | 5-Cl | $CF_3$ | $CH_2$-3-furanyl |
| 1013 | 5-Cl | $CF_3$ | $CH_2$-2-thienyl |
| 1014 | 5-Cl | $CF_3$ | $CH_2$-3-thienyl |
| 1015 | 5-Cl | $CF_3$ | $CH_2CH_2$-cycPr |
| 1016 | 5-Cl | $CF_3$ | $CH_2CH_2$—Ph |
| 1017 | 5-Cl | $CF_3$ | $CH_2CH_2$-2-Pyridyl |
| 1018 | 5-Cl | $CF_3$ | $CH_2CH_2$-3-Pyridyl |
| 1019 | 5-Cl | $CF_3$ | $CH_2CH_2$-4-Pyridyl |
| 1020 | 5-Cl | $CF_3$ | $CH_2CH_2$-2-furanyl |
| 1021 | 5-Cl | $CF_3$ | $CH_2CH_2$-3-furanyl |
| 1022 | 5-Cl | $CF_3$ | $CH_2CH_2$-2-thienyl |
| 1023 | 5-Cl | $CF_3$ | $CH_2CH_2$-3-thienyl |
| 1024 | 5-Cl | $CF_3$ | C≡C—Et |
| 1025 | 5-Cl | $CF_3$ | C≡C-iPr |
| 1026 | 5-Cl | $CF_3$ | C≡C-cycPr |
| 1027 | 5-Cl | $CF_3$ | C≡C-1-(Me)cycPr |
| 1028 | 5-Cl | $CF_3$ | C≡C-2-pyridyl |
| 1029 | 5-Cl | $CF_3$ | C≡C-3-pyridyl |
| 1030 | 5-Cl | $CF_3$ | C≡C-4-pyridyl |
| 1031 | 5-Cl | $CF_3$ | C≡C-2-furanyl |
| 1032 | 5-Cl | $CF_3$ | C≡C-3-furanyl |
| 1033 | 5-Cl | $CF_3$ | C≡C-2-thienyl |
| 1034 | 5-Cl | $CF_3$ | C≡C-3-thienyl |
| 1035 | 5-Cl | $CF_3$ | CH=CH—Et |
| 1036 | 5-Cl | $CF_3$ | CH=CH-iPr |
| 1037 | 5-Cl | $CF_3$ | CH=CH-cycPr |
| 1038 | 5-Cl | $CF_3$ | CH=CH-1-(Me)cycPr |
| 1039 | 5-Cl | $CF_3$ | CH=CH-2-pyridyl |
| 1040 | 5-Cl | $CF_3$ | CH=CH-3-pyridyl |
| 1041 | 5-Cl | $CF_3$ | CH=CH-4-pyridyl |
| 1042 | 5-Cl | $CF_3$ | CH=CH-2-furanyl |
| 1043 | 5-Cl | $CF_3$ | CH=CH-3-furanyl |
| 1044 | 5-Cl | $CF_3$ | CH=CH-2-thienyl |
| 1045 | 5-Cl | $CF_3$ | CH=CH-3-thienyl |
| 1046 | 5-Cl | $CF_3$ | $CH_2$—C≡C-cycPr |
| 1047 | 5-Cl | $CF_3$ | $CH_2$—C≡C-2-furanyl |
| 1048 | 5-Cl | $CF_3$ | $CH_2$CH=CH-cycPr |
| 1049 | 5-Cl | $CF_3$ | $CH_2$CH=CH-2-furanyl |
| 1050 | 5-Cl | $CF_3$ | CH=$CHCH_2$-cycPr |
| 1051 | 5-Cl | $CF_3$ | CH=$CHCH_2$-2-furanyl |
| 1052 | 6-Cl | $CF_3$ | $CH_2CH_2CH_3$ |
| 1053 | 6-Cl | $CF_3$ | $CH_2CH_2CH_2CH_3$ |
| 1054 | 6-Cl | $CF_3$ | $CH_2CH_2CH_2CH_2CH_3$ |
| 1055 | 6-Cl | $CF_3$ | $CH_2CH_2CH(CH_3)_2$ |
| 1056 | 6-Cl | $CF_3$ | $CH_2CH_2$-tBu |
| 1057 | 6-Cl | $CF_3$ | $CH_2$-cycPr |

TABLE 2-continued

| | | | |
|---|---|---|---|
| 1058 | 6-Cl | $CF_3$ | $CH_2$—Ph |
| 1059 | 6-Cl | $CF_3$ | $CH_2$-2-Pyridyl |
| 1060 | 6-Cl | $CF_3$ | $CH_2$-3-Pyridyl |
| 1061 | 6-Cl | $CF_3$ | $CH_2$-4-Pyridyl |
| 1062 | 6-Cl | $CF_3$ | $CH_2$-2-furanyl |
| 1063 | 6-Cl | $CF_3$ | $CH_2$-3-furanyl |
| 1064 | 6-Cl | $CF_3$ | $CH_2$-2-thienyl |
| 1065 | 6-Cl | $CF_3$ | $CH_2$-3-thienyl |
| 1066 | 6-Cl | $CF_3$ | $CH_2CH_2$-cycPr |
| 1067 | 6-Cl | $CF_3$ | $CH_2CH_2$—Ph |
| 1068 | 6-Cl | $CF_3$ | $CH_2CH_2$-2-Pyridyl |
| 1069 | 6-Cl | $CF_3$ | $CH_2CH_2$-3-Pyridyl |
| 1070 | 6-Cl | $CF_3$ | $CH_2CH_2$-4-Pyridyl |
| 1071 | 6-Cl | $CF_3$ | $CH_2CH_2$-2-furanyl |
| 1072 | 6-Cl | $CF_3$ | $CH_2CH_2$-3-furanyl |
| 1073 | 6-Cl | $CF_3$ | $CH_2CH_2$-2-thienyl |
| 1074 | 6-Cl | $CF_3$ | $CH_2CH_2$-3-thienyl |
| 1075 | 6-Cl | $CF_3$ | C≡C—Et |
| 1076 | 6-Cl | $CF_3$ | C≡C-iPr |
| 1077 | 6-Cl | $CF_3$ | C≡C-cycPr |
| 1078 | 6-Cl | $CF_3$ | C≡C-1-(Me)cycPr |
| 1079 | 6-Cl | $CF_3$ | C≡C-2-pyridyl |
| 1080 | 6-Cl | $CF_3$ | C≡C-3-pyridyl |
| 1081 | 6-Cl | $CF_3$ | C≡C-4-pyridyl |
| 1082 | 6-Cl | $CF_3$ | C≡C-2-furanyl |
| 1083 | 6-Cl | $CF_3$ | C≡C-3-furanyl |
| 1084 | 6-Cl | $CF_3$ | C≡C-2-thienyl |
| 1085 | 6-Cl | $CF_3$ | C≡C-3-thienyl |
| 1086 | 6-Cl | $CF_3$ | CH═CH—Et |
| 1087 | 6-Cl | $CF_3$ | CH═CH-iPr |
| 1088 | 6-Cl | $CF_3$ | CH═CH-cycPr |
| 1089 | 6-Cl | $CF_3$ | CH═CH-1-(Me)cycPr |
| 1090 | 6-Cl | $CF_3$ | CH═CH-2-pyridyl |
| 1091 | 6-Cl | $CF_3$ | CH═CH-3-pyridyl |
| 1092 | 6-Cl | $CF_3$ | CH═CH-4-pyridyl |
| 1093 | 6-Cl | $CF_3$ | CH═CH-2-furanyl |
| 1094 | 6-Cl | $CF_3$ | CH═CH-3-furanyl |
| 1095 | 6-Cl | $CF_3$ | CH═CH-2-thienyl |
| 1096 | 6-Cl | $CF_3$ | CH═CH-3-thienyl |
| 1097 | 6-Cl | $CF_3$ | $CH_2$—C≡C-cycPr |
| 1098 | 6-Cl | $CF_3$ | $CH_2$—C≡C-2-furanyl |
| 1099 | 6-Cl | $CF_3$ | $CH_2$CH═CH-cycPr |
| 1100 | 6-Cl | $CF_3$ | $CH_2$CH═CH-2-furanyl |
| 1101 | 6-Cl | $CF_3$ | CH═CHCH$_2$-cycPr |
| 1102 | 6-Cl | $CF_3$ | CH═CHCH$_2$-2-furanyl |
| 1103 | 5-F | $CF_3$ | $CH_2CH_2CH_3$ |
| 1104 | 5-F | $CF_3$ | $CH_2CH_2CH_2CH_3$ |
| 1105 | 5-F | $CF_3$ | $CH_2CH_2CH_2CH_2CH_3$ |
| 1106 | 5-F | $CF_3$ | $CH_2CH_2CH(CH_3)_2$ |
| 1107 | 5-F | $CF_3$ | $CH_2CH_2$-tBu |
| 1108 | 5-F | $CF_3$ | $CH_2$-cycPr |
| 1109 | 5-F | $CF_3$ | $CH_2$—Ph |
| 1110 | 5-F | $CF_3$ | $CH_2$-2-Pyridyl |
| 1111 | 5-F | $CF_3$ | $CH_2$-3-Pyridyl |
| 1112 | 5-F | $CF_3$ | $CH_2$-4-Pyridyl |
| 1113 | 5-F | $CF_3$ | $CH_2$-2-furanyl |
| 1114 | 5-F | $CF_3$ | $CH_2$-3-furanyl |
| 1115 | 5-F | $CF_3$ | $CH_2$-2-thienyl |
| 1116 | 5-F | $CF_3$ | $CH_2$-3-thienyl |
| 1117 | 5-F | $CF_3$ | $CH_2CH_2$-cycPr |
| 1118 | 5-F | $CF_3$ | $CH_2CH_2$—Ph |
| 1119 | 5-F | $CF_3$ | $CH_2CH_2$-2-Pyridyl |
| 1120 | 5-F | $CF_3$ | $CH_2CH_2$-3-Pyridyl |
| 1121 | 5-F | $CF_3$ | $CH_2CH_2$-4-Pyridyl |
| 1122 | 5-F | $CF_3$ | $CH_2CH_2$-2-furanyl |
| 1123 | 5-F | $CF_3$ | $CH_2CH_2$-3-furanyl |
| 1124 | 5-F | $CF_3$ | $CH_2CH_2$-2-thienyl |
| 1125 | 5-F | $CF_3$ | $CH_2CH_2$-3-thienyl |
| 1126 | 5-F | $CF_3$ | C≡C—Et |
| 1127 | 5-F | $CF_3$ | C≡C-iPr |
| 1128 | 5-F | $CF_3$ | C≡C-cycPr |
| 1129 | 5-F | $CF_3$ | C≡C-1-(Me)cycPr |
| 1130 | 5-F | $CF_3$ | C≡C-2-pyridyl |
| 1131 | 5-F | $CF_3$ | C≡C-3-pyridyl |
| 1132 | 5-F | $CF_3$ | C≡C-4-pyridyl |
| 1133 | 5-F | $CF_3$ | C≡C-2-furanyl |
| 1134 | 5-F | $CF_3$ | C≡C-3-furanyl |
| 1135 | 5-F | $CF_3$ | C≡C-2-thienyl |
| 1136 | 5-F | $CF_3$ | C≡C-3-thienyl |
| 1137 | 5-F | $CF_3$ | CH═CH—Et |
| 1138 | 5-F | $CF_3$ | CH═CH-iPr |
| 1139 | 5-F | $CF_3$ | CH═CH-cycPr |
| 1140 | 5-F | $CF_3$ | CH═CH-1-(Me)cycPr |
| 1141 | 5-F | $CF_3$ | CH═CH-2-pyridyl |
| 1142 | 5-F | $CF_3$ | CH═CH-3-pyridyl |
| 1143 | 5-F | $CF_3$ | CH═CH-4-pyridyl |
| 1144 | 5-F | $CF_3$ | CH═CH-2-furanyl |
| 1145 | 5-F | $CF_3$ | CH═CH-3-furanyl |
| 1146 | 5-F | $CF_3$ | CH═CH-2-thienyl |
| 1147 | 5-F | $CF_3$ | CH═CH-3-thienyl |
| 1148 | 5-F | $CF_3$ | $CH_2$—C≡C-cycPr |
| 1149 | 5-F | $CF_3$ | $CH_2$—C≡C-2-furanyl |
| 1150 | 5-F | $CF_3$ | $CH_2$CH═CH-cycPr |
| 1151 | 5-F | $CF_3$ | $CH_2$CH═CH-2-furanyl |
| 1152 | 5-F | $CF_3$ | CH═CHCH$_2$-cycPr |
| 1153 | 5-F | $CF_3$ | CH═CHCH$_2$-2-furanyl |
| 1154 | 6-F | $CF_3$ | $CH_2CH_2CH_3$ |
| 1155 | 6-F | $CF_3$ | $CH_2CH_2CH_2CH_3$ |
| 1156 | 6-F | $CF_3$ | $CH_2CH_2CH_2CH_2CH_3$ |
| 1157 | 6-F | $CF_3$ | $CH_2CH_2CH(CH_3)_2$ |
| 1158 | 6-F | $CF_3$ | $CH_2CH_2$-tBu |
| 1159 | 6-F | $CF_3$ | $CH_2$-cycPr |
| 1160 | 6-F | $CF_3$ | $CH_2$—Ph |
| 1161 | 6-F | $CF_3$ | $CH_2$-2-Pyridyl |
| 1162 | 6-F | $CF_3$ | $CH_2$-3-Pyridyl |
| 1163 | 6-F | $CF_3$ | $CH_2$-4-Pyridyl |
| 1164 | 6-F | $CF_3$ | $CH_2$-2-furanyl |
| 1165 | 6-F | $CF_3$ | $CH_2$-3-furanyl |
| 1166 | 6-F | $CF_3$ | $CH_2$-2-thienyl |
| 1167 | 6-F | $CF_3$ | $CH_2$-3-thienyl |
| 1168 | 6-F | $CF_3$ | $CH_2CH_2$-cycPr |
| 1169 | 6-F | $CF_3$ | $CH_2CH_2$—Ph |
| 1170 | 6-F | $CF_3$ | $CH_2CH_2$-2-Pyridyl |
| 1171 | 6-F | $CF_3$ | $CH_2CH_2$-3-Pyridyl |
| 1172 | 6-F | $CF_3$ | $CH_2CH_2$-4-Pyridyl |
| 1173 | 6-F | $CF_3$ | $CH_2CH_2$-2-furanyl |
| 1174 | 6-F | $CF_3$ | $CH_2CH_2$-3-furanyl |
| 1175 | 6-F | $CF_3$ | $CH_2CH_2$-2-thienyl |
| 1176 | 6-F | $CF_3$ | $CH_2CH_2$-3-thienyl |
| 1177 | 6-F | $CF_3$ | C≡C—Et |
| 1178 | 6-F | $CF_3$ | C≡C-iPr |
| 1179 | 6-F | $CF_3$ | C≡C-cycPr |
| 1180 | 6-F | $CF_3$ | C≡C-1-(Me)cycPr |
| 1181 | 6-F | $CF_3$ | C≡C-2-pyridyl |
| 1182 | 6-F | $CF_3$ | C≡C-3-pyridyl |
| 1183 | 6-F | $CF_3$ | C≡C-4-pyridyl |
| 1184 | 6-F | $CF_3$ | C≡C-2-furanyl |
| 1185 | 6-F | $CF_3$ | C≡C-3-furanyl |
| 1186 | 6-F | $CF_3$ | C≡C-2-thienyl |
| 1187 | 6-F | $CF_3$ | C≡C-3-thienyl |
| 1188 | 6-F | $CF_3$ | CH═CH—Et |
| 1189 | 6-F | $CF_3$ | CH═CH-iPr |
| 1190 | 6-F | $CF_3$ | CH═CH-cycPr |
| 1191 | 6-F | $CF_3$ | CH═CH-1-(Me)cycPr |
| 1192 | 6-F | $CF_3$ | CH═CH-2-pyridyl |
| 1193 | 6-F | $CF_3$ | CH═CH-3-pyridyl |
| 1194 | 6-F | $CF_3$ | CH═CH-4-pyridyl |
| 1195 | 6-F | $CF_3$ | CH═CH-2-furanyl |
| 1196 | 6-F | $CF_3$ | CH═CH-3-furanyl |
| 1197 | 6-F | $CF_3$ | CH═CH-2-thienyl |
| 1198 | 6-F | $CF_3$ | CH═CH-3-thienyl |
| 1199 | 6-F | $CF_3$ | $CH_2$—C≡C-cycPr |
| 1200 | 6-F | $CF_3$ | $CH_2$—C≡C-2-furanyl |
| 1201 | 6-F | $CF_3$ | $CH_2$CH═CH-cycPr |
| 1202 | 6-F | $CF_3$ | $CH_2$CH═CH-2-furanyl |
| 1203 | 6-F | $CF_3$ | CH═CHCH$_2$-cycPr |
| 1204 | 6-F | $CF_3$ | CH═CHCH$_2$-2-furanyl |
| 1205 | 5,6-diCl | $CF_3$ | $CH_2CH_2CH_3$ |
| 1206 | 5,6-diCl | $CF_3$ | $CH_2CH_2CH_2CH_3$ |
| 1207 | 5,6-diCl | $CF_3$ | $CH_2CH_2CH_2CH_2CH_3$ |
| 1208 | 5,6-diCl | $CF_3$ | $CH_2CH_2CH(CH_3)_2$ |
| 1209 | 5,6-diCl | $CF_3$ | $CH_2CH_2$-tBu |
| 1210 | 5,6-diCl | $CF_3$ | $CH_2$-cycPr |
| 1211 | 5,6-diCl | $CF_3$ | $CH_2$—Ph |
| 1212 | 5,6-diCl | $CF_3$ | $CH_2$-2-Pyridyl |
| 1213 | 5,6-diCl | $CF_3$ | $CH_2$-3-Pyridyl |
| 1214 | 5,6-diCl | $CF_3$ | $CH_2$-4-Pyridyl |
| 1215 | 5,6-diCl | $CF_3$ | $CH_2$-2-furanyl |

TABLE 2-continued

| | | | |
|---|---|---|---|
| 1216 | 5,6-diCl | $CF_3$ | $CH_2$-3-furanyl |
| 1217 | 5,6-diCl | $CF_3$ | $CH_2$-2-thienyl |
| 1218 | 5,6-diCl | $CF_3$ | $CH_2$-3-thienyl |
| 1219 | 5,6-diCl | $CF_3$ | $CH_2CH_2$-cycPr |
| 1220 | 5,6-diCl | $CF_3$ | $CH_2CH_2$—Ph |
| 1221 | 5,6-diCl | $CF_3$ | $CH_2CH_2$-2-Pyridyl |
| 1222 | 5,6-diCl | $CF_3$ | $CH_2CH_2$-3-Pyridyl |
| 1223 | 5,6-diCl | $CF_3$ | $CH_2CH_2$-4-Pyridyl |
| 1224 | 5,6-diCl | $CF_3$ | $CH_2CH_2$-2-furanyl |
| 1225 | 5,6-diCl | $CF_3$ | $CH_2CH_2$-3-furanyl |
| 1226 | 5,6-diCl | $CF_3$ | $CH_2CH_2$-2-thienyl |
| 1227 | 5,6-diCl | $CF_3$ | $CH_2CH_2$-3-thienyl |
| 1228 | 5,6-diCl | $CF_3$ | C≡C—Et |
| 1229 | 5,6-diCl | $CF_3$ | C≡C-iPr |
| 1230 | 5,6-diCl | $CF_3$ | C≡C-cycPr |
| 1231 | 5,6-diCl | $CF_3$ | C≡C-1-(Me)cycPr |
| 1232 | 5,6-diCl | $CF_3$ | C≡C-2-pyridyl |
| 1233 | 5,6-diCl | $CF_3$ | C≡C-3-pyridyl |
| 1234 | 5,6-diCl | $CF_3$ | C≡C-4-pyridyl |
| 1235 | 5,6-diCl | $CF_3$ | C≡C-2-furanyl |
| 1236 | 5,6-diCl | $CF_3$ | C≡C-3-furanyl |
| 1237 | 5,6-diCl | $CF_3$ | C≡C-2-thienyl |
| 1238 | 5,6-diCl | $CF_3$ | C≡C-3-thienyl |
| 1239 | 5,6-diCl | $CF_3$ | CH=CH—Et |
| 1240 | 5,6-diCl | $CF_3$ | CH=CH-iPr |
| 1241 | 5,6-diCl | $CF_3$ | CH=CH-cycPr |
| 1242 | 5,6-diCl | $CF_3$ | CH=CH-1-(Me)cycPr |
| 1243 | 5,6-diCl | $CF_3$ | CH=CH-2-pyridyl |
| 1244 | 5,6-diCl | $CF_3$ | CH=CH-3-pyridyl |
| 1245 | 5,6-diCl | $CF_3$ | CH=CH-4-pyridyl |
| 1246 | 5,6-diCl | $CF_3$ | CH=CH-2-furanyl |
| 1247 | 5,6-diCl | $CF_3$ | CH=CH-3-furanyl |
| 1248 | 5,6-diCl | $CF_3$ | CH=CH-2-thienyl |
| 1249 | 5,6-diCl | $CF_3$ | CH=CH-3-thienyl |
| 1250 | 5,6-diCl | $CF_3$ | $CH_2$—C≡C-cycPr |
| 1251 | 5,6-diCl | $CF_3$ | $CH_2$—C≡C-2-furanyl |
| 1252 | 5,6-diCl | $CF_3$ | $CH_2$CH=CH-cycPr |
| 1253 | 5,6-diCl | $CF_3$ | $CH_2$CH=CH-2-furanyl |
| 1254 | 5,6-diCl | $CF_3$ | CH=CH$CH_2$-cycPr |
| 1255 | 5,6-diCl | $CF_3$ | CH=CH$CH_2$-2-furanyl |
| 1256 | 5,6-diF | $CF_3$ | $CH_2CH_2CH_3$ |
| 1257 | 5,6-diF | $CF_3$ | $CH_2CH_2CH_2CH_3$ |
| 1258 | 5,6-diF | $CF_3$ | $CH_2CH_2CH_2CH_2CH_3$ |
| 1259 | 5,6-diF | $CF_3$ | $CH_2CH_2CH(CH_3)_2$ |
| 1260 | 5,6-diF | $CF_3$ | $CH_2CH_2$-tBu |
| 1261 | 5,6-diF | $CF_3$ | $CH_2$-cycPr |
| 1262 | 5,6-diF | $CF_3$ | $CH_2$—Ph |
| 1263 | 5,6-diF | $CF_3$ | $CH_2$-2-Pyridyl |
| 1264 | 5,6-diF | $CF_3$ | $CH_2$-3-Pyridyl |
| 1265 | 5,6-diF | $CF_3$ | $CH_2$-4-Pyridyl |
| 1266 | 5,6-diF | $CF_3$ | $CH_2$-2-furanyl |
| 1267 | 5,6-diF | $CF_3$ | $CH_2$-3-furanyl |
| 1268 | 5,6-diF | $CF_3$ | $CH_2$-2-thienyl |
| 1269 | 5,6-diF | $CF_3$ | $CH_2$-3-thienyl |
| 1270 | 5,6-diF | $CF_3$ | $CH_2CH_2$-cycPr |
| 1271 | 5,6-diF | $CF_3$ | $CH_2CH_2$—Ph |
| 1272 | 5,6-diF | $CF_3$ | $CH_2CH_2$-2-Pyridyl |
| 1273 | 5,6-diF | $CF_3$ | $CH_2CH_2$-3-Pyridyl |
| 1274 | 5,6-diF | $CF_3$ | $CH_2CH_2$-4-Pyridyl |
| 1275 | 5,6-diF | $CF_3$ | $CH_2CH_2$-2-furanyl |
| 1276 | 5,6-diF | $CF_3$ | $CH_2CH_2$-3-furanyl |
| 1277 | 5,6-diF | $CF_3$ | $CH_2CH_2$-2-thienyl |
| 1278 | 5,6-diF | $CF_3$ | $CH_2CH_2$-3-thienyl |
| 1279 | 5,6-diF | $CF_3$ | C≡C—Et |
| 1280 | 5,6-diF | $CF_3$ | C≡C-iPr |
| 1281 | 5,6-diF | $CF_3$ | C≡C-cycPr |
| 1282 | 5,6-diF | $CF_3$ | C≡C-1-(Me)cycPr |
| 1283 | 5,6-diF | $CF_3$ | C≡C-2-pyridyl |
| 1284 | 5,6-diF | $CF_3$ | C≡C-3-pyridyl |
| 1285 | 5,6-diF | $CF_3$ | C≡C-4-pyridyl |
| 1286 | 5,6-diF | $CF_3$ | C≡C-2-furanyl |
| 1287 | 5,6-diF | $CF_3$ | C≡C-3-furanyl |
| 1288 | 5,6-diF | $CF_3$ | C≡C-2-thienyl |
| 1289 | 5,6-diF | $CF_3$ | C≡C-3-thienyl |
| 1290 | 5,6-diF | $CF_3$ | CH=CH—Et |
| 1291 | 5,6-diF | $CF_3$ | CH=CH-iPr |
| 1292 | 5,6-diF | $CF_3$ | CH=CH-cycPr |
| 1293 | 5,6-diF | $CF_3$ | CH=CH-1-(Me)cycPr |
| 1294 | 5,6-diF | $CF_3$ | CH=CH-2-pyridyl |
| 1295 | 5,6-diF | $CF_3$ | CH=CH-3-pyridyl |
| 1296 | 5,6-diF | $CF_3$ | CH=CH-4-pyridyl |
| 1297 | 5,6-diF | $CF_3$ | CH=CH-2-furanyl |
| 1298 | 5,6-diF | $CF_3$ | CH=CH-3-furanyl |
| 1299 | 5,6-diF | $CF_3$ | CH=CH-2-thienyl |
| 1300 | 5,6-diF | $CF_3$ | CH=CH-3-thienyl |
| 1301 | 5,6-diF | $CF_3$ | $CH_2$—C≡C-cycPr |
| 1302 | 5,6-diF | $CF_3$ | $CH_2$—C≡C-2-furanyl |
| 1303 | 5,6-diF | $CF_3$ | $CH_2$CH=CH-cycPr |
| 1304 | 5,6-diF | $CF_3$ | $CH_2$CH=CH-2-furanyl |
| 1305 | 5,6-diF | $CF_3$ | CH=CH$CH_2$-cycPr |
| 1306 | 5,6-diF | $CF_3$ | CH=CH$CH_2$-2-furanyl |
| 1307 | 5-Cl, 6-F | $CF_3$ | $CH_2CH_2CH_3$ |
| 1308 | 5-Cl, 6-F | $CF_3$ | $CH_2CH_2CH_2CH_3$ |
| 1309 | 5-Cl, 6-F | $CF_3$ | $CH_2CH_2CH_2CH_2CH_3$ |
| 1310 | 5-Cl, 6-F | $CF_3$ | $CH_2CH_2CH(CH_3)_2$ |
| 1311 | 5-Cl, 6-F | $CF_3$ | $CH_2CH_2$-tBu |
| 1312 | 5-Cl, 6-F | $CF_3$ | $CH_2$-cycPr |
| 1313 | 5-Cl, 6-F | $CF_3$ | $CH_2$—Ph |
| 1314 | 5-Cl, 6-F | $CF_3$ | $CH_2$-2-Pyridyl |
| 1315 | 5-Cl, 6-F | $CF_3$ | $CH_2$-3-Pyridyl |
| 1316 | 5-Cl, 6-F | $CF_3$ | $CH_2$-4-Pyridyl |
| 1317 | 5-Cl, 6-F | $CF_3$ | $CH_2$-2-furanyl |
| 1318 | 5-Cl, 6-F | $CF_3$ | $CH_2$-3-furanyl |
| 1319 | 5-Cl, 6-F | $CF_3$ | $CH_2$-2-thienyl |
| 1320 | 5-Cl, 6-F | $CF_3$ | $CH_2$-3-thienyl |
| 1321 | 5-Cl, 6-F | $CF_3$ | $CH_2CH_2$-cycPr |
| 1322 | 5-Cl, 6-F | $CF_3$ | $CH_2CH_2$—Ph |
| 1323 | 5-Cl, 6-F | $CF_3$ | $CH_2CH_2$-2-Pyridyl |
| 1324 | 5-Cl, 6-F | $CF_3$ | $CH_2CH_2$-3-Pyridyl |
| 1325 | 5-Cl, 6-F | $CF_3$ | $CH_2CH_2$-4-Pyridyl |
| 1326 | 5-Cl, 6-F | $CF_3$ | $CH_2CH_2$-2-furanyl |
| 1327 | 5-Cl, 6-F | $CF_3$ | $CH_2CH_2$-3-furanyl |
| 1328 | 5-Cl, 6-F | $CF_3$ | $CH_2CH_2$-2-thienyl |
| 1329 | 5-Cl, 6-F | $CF_3$ | $CH_2CH_2$-3-thienyl |
| 1330 | 5-Cl, 6-F | $CF_3$ | C≡C—Et |
| 1331 | 5-Cl, 6-F | $CF_3$ | C≡C-iPr |
| 1332 | 5-Cl, 6-F | $CF_3$ | C≡C-cycPr |
| 1333 | 5-Cl, 6-F | $CF_3$ | C≡C-1-(Me)cycPr |
| 1334 | 5-Cl, 6-F | $CF_3$ | C≡C-2-pyridyl |
| 1335 | 5-Cl, 6-F | $CF_3$ | C≡C-3-pyridyl |
| 1336 | 5-Cl, 6-F | $CF_3$ | C≡C-4-pyridyl |
| 1337 | 5-Cl, 6-F | $CF_3$ | C≡C-2-furanyl |
| 1338 | 5-Cl, 6-F | $CF_3$ | C≡C-3-furanyl |
| 1339 | 5-Cl, 6-F | $CF_3$ | C≡C-2-thienyl |
| 1340 | 5-Cl, 6-F | $CF_3$ | C≡C-3-thienyl |
| 1341 | 5-Cl, 6-F | $CF_3$ | CH=CH—Et |
| 1342 | 5-Cl, 6-F | $CF_3$ | CH=CH-iPr |
| 1343 | 5-Cl, 6-F | $CF_3$ | CH=CH-cycPr |
| 1344 | 5-Cl, 6-F | $CF_3$ | CH=CH-1-(Me)cycPr |
| 1345 | 5-Cl, 6-F | $CF_3$ | CH=CH-2-pyridyl |
| 1346 | 5-Cl, 6-F | $CF_3$ | CH=CH-3-pyridyl |
| 1347 | 5-Cl, 6-F | $CF_3$ | CH=CH-4-pyridyl |
| 1348 | 5-Cl, 6-F | $CF_3$ | CH=CH-2-furanyl |
| 1349 | 5-Cl, 6-F | $CF_3$ | CH=CH-3-furanyl |
| 1350 | 5-Cl, 6-F | $CF_3$ | CH=CH-2-thienyl |
| 1351 | 5-Cl, 6-F | $CF_3$ | CH=CH-3-thienyl |
| 1352 | 5-Cl, 6-F | $CF_3$ | $CH_2$—C≡C-cycPr |
| 1353 | 5-Cl, 6-F | $CF_3$ | $CH_2$—C≡C-2-furanyl |
| 1354 | 5-Cl, 6-F | $CF_3$ | $CH_2$CH=CH-cycPr |
| 1355 | 5-Cl, 6-F | $CF_3$ | $CH_2$CH=CH-2-furanyl |
| 1356 | 5-Cl, 6-F | $CF_3$ | CH=CH$CH_2$-cycPr |
| 1357 | 5-Cl, 6-F | $CF_3$ | CH=CH$CH_2$-2-furanyl |
| 1358 | 5-F, 6-Cl | $CF_3$ | $CH_2CH_2CH_3$ |
| 1359 | 5-F, 6-Cl | $CF_3$ | $CH_2CH_2CH_2CH_3$ |
| 1360 | 5-F, 6-Cl | $CF_3$ | $CH_2CH_2CH_2CH_2CH_3$ |
| 1361 | 5-F, 6-Cl | $CF_3$ | $CH_2CH_2CH(CH_3)_2$ |
| 1362 | 5-F, 6-Cl | $CF_3$ | $CH_2CH_2$-tBu |
| 1363 | 5-F, 6-Cl | $CF_3$ | $CH_2$-cycPr |
| 1364 | 5-F, 6-Cl | $CF_3$ | $CH_2$—Ph |
| 1365 | 5-F, 6-Cl | $CF_3$ | $CH_2$-2-Pyridyl |
| 1366 | 5-F, 6-Cl | $CF_3$ | $CH_2$-3-Pyridyl |
| 1367 | 5-F, 6-Cl | $CF_3$ | $CH_2$-4-Pyridyl |
| 1368 | 5-F, 6-Cl | $CF_3$ | $CH_2$-2-furanyl |
| 1369 | 5-F, 6-Cl | $CF_3$ | $CH_2$-3-furanyl |
| 1370 | 5-F, 6-Cl | $CF_3$ | $CH_2$-2-thienyl |
| 1371 | 5-F, 6-Cl | $CF_3$ | $CH_2$-3-thienyl |
| 1372 | 5-F, 6-Cl | $CF_3$ | $CH_2CH_2$-cycPr |
| 1373 | 5-F, 6-Cl | $CF_3$ | $CH_2CH_2$—Ph |

TABLE 2-continued

| | | | |
|---|---|---|---|
| 1374 | 5-F, 6-Cl | CF$_3$ | CH$_2$CH$_2$-2-Pyridyl |
| 1375 | 5-F, 6-Cl | CF$_3$ | CH$_2$CH$_2$-3-Pyridyl |
| 1376 | 5-F, 6-Cl | CF$_3$ | CH$_2$CH$_2$-4-Pyridyl |
| 1377 | 5-F, 6-Cl | CF$_3$ | CH$_2$CH$_2$-2-furanyl |
| 1378 | 5-F, 6-Cl | CF$_3$ | CH$_2$CH$_2$-3-furanyl |
| 1379 | 5-F, 6-Cl | CF$_3$ | CH$_2$CH$_2$-2-thienyl |
| 1380 | 5-F, 6-Cl | CF$_3$ | CH$_2$CH$_2$-3-thienyl |
| 1381 | 5-F, 6-Cl | CF$_3$ | C≡C—Et |
| 1382 | 5-F, 6-Cl | CF$_3$ | C≡C-iPr |
| 1383 | 5-F, 6-Cl | CF$_3$ | C≡C-cycPr |
| 1384 | 5-F, 6-Cl | CF$_3$ | C≡C-1-(Me)cycPr |
| 1385 | 5-F, 6-Cl | CF$_3$ | C≡C-2-pyridyl |
| 1386 | 5-F, 6-Cl | CF$_3$ | C≡C-3-pyridyl |
| 1387 | 5-F, 6-Cl | CF$_3$ | C≡C-4-pyridyl |
| 1388 | 5-F, 6-Cl | CF$_3$ | C≡C-2-furanyl |
| 1389 | 5-F, 6-Cl | CF$_3$ | C≡C-3-furanyl |
| 1390 | 5-F, 6-Cl | CF$_3$ | C≡C-2-thienyl |
| 1391 | 5-F, 6-Cl | CF$_3$ | C≡C-3-thienyl |
| 1392 | 5-F, 6-Cl | CF$_3$ | CH=CH—Et |
| 1393 | 5-F, 6-Cl | CF$_3$ | CH=CH-iPr |
| 1394 | 5-F, 6-Cl | CF$_3$ | CH=CH-cycPr |
| 1395 | 5-F, 6-Cl | CF$_3$ | CH=CH-1-(Me)cycPr |
| 1396 | 5-F, 6-Cl | CF$_3$ | CH=CH-2-pyridyl |
| 1397 | 5-F, 6-Cl | CF$_3$ | CH=CH-3-pyridyl |
| 1398 | 5-F, 6-Cl | CF$_3$ | CH=CH-4-pyridyl |
| 1399 | 5-F, 6-Cl | CF$_3$ | CH=CH-2-furanyl |
| 1400 | 5-F, 6-Cl | CF$_3$ | CH=CH-3-furanyl |
| 1401 | 5-F, 6-Cl | CF$_3$ | CH=CH-2-thienyl |
| 1402 | 5-F, 6-Cl | CF$_3$ | CH=CH-3-thienyl |
| 1403 | 5-F, 6-Cl | CF$_3$ | CH$_2$—C≡C-cycPr |
| 1404 | 5-F, 6-Cl | CF$_3$ | CH$_2$—C≡C-2-furanyl |
| 1405 | 5-F, 6-Cl | CF$_3$ | CH$_2$CH=CH-cycPr |
| 1406 | 5-F, 6-Cl | CF$_3$ | CH$_2$CH=CH-2-furanyl |
| 1407 | 5-F, 6-Cl | CF$_3$ | CH=CHCH$_2$-cycPr |
| 1408 | 5-F, 6-Cl | CF$_3$ | CH=CHCH$_2$-2-furanyl |
| 1409 | 6-CH$_3$ | CF$_3$ | CH$_2$CH$_2$CH$_3$ |
| 1410 | 6-CH$_3$ | CF$_3$ | CH$_2$CH$_2$CH$_2$CH$_3$ |
| 1411 | 6-CH$_3$ | CF$_3$ | CH$_2$CH$_2$CH$_2$CH$_2$CH$_3$ |
| 1412 | 6-CH$_3$ | CF$_3$ | CH$_2$CH$_2$CH(CH$_3$)$_2$ |
| 1413 | 6-CH$_3$ | CF$_3$ | CH$_2$CH$_2$-tBu |
| 1414 | 6-CH$_3$ | CF$_3$ | CH$_2$-cycPr |
| 1415 | 6-CH$_3$ | CF$_3$ | CH$_2$—Ph |
| 1416 | 6-CH$_3$ | CF$_3$ | CH$_2$-2-Pyridyl |
| 1417 | 6-CH$_3$ | CF$_3$ | CH$_2$-3-Pyridyl |
| 1418 | 6-CH$_3$ | CF$_3$ | CH$_2$-4-Pyridyl |
| 1419 | 6-CH$_3$ | CF$_3$ | CH$_2$-2-furanyl |
| 1420 | 6-CH$_3$ | CF$_3$ | CH$_2$-3-furanyl |
| 1421 | 6-CH$_3$ | CF$_3$ | CH$_2$-2-thienyl |
| 1422 | 6-CH$_3$ | CF$_3$ | CH$_2$-3-thienyl |
| 1423 | 6-CH$_3$ | CF$_3$ | CH$_2$CH$_2$-cycPr |
| 1424 | 6-CH$_3$ | CF$_3$ | CH$_2$CH$_2$—Ph |
| 1425 | 6-CH$_3$ | CF$_3$ | CH$_2$CH$_2$-2-Pyridyl |
| 1426 | 6-CH$_3$ | CF$_3$ | CH$_2$CH$_2$-3-Pyridyl |
| 1427 | 6-CH$_3$ | CF$_3$ | CH$_2$CH$_2$-4-Pyridyl |
| 1428 | 6-CH$_3$ | CF$_3$ | CH$_2$CH$_2$-2-furanyl |
| 1429 | 6-CH$_3$ | CF$_3$ | CH$_2$CH$_2$-3-furanyl |
| 1430 | 6-CH$_3$ | CF$_3$ | CH$_2$CH$_2$-2-thienyl |
| 1431 | 6-CH$_3$ | CF$_3$ | CH$_2$CH$_2$-3-thienyl |
| 1432 | 6-CH$_3$ | CF$_3$ | C≡C—Et |
| 1433 | 6-CH$_3$ | CF$_3$ | C≡C-iPr |
| 1434 | 6-CH$_3$ | CF$_3$ | C≡C-cycPr |
| 1435 | 6-CH$_3$ | CF$_3$ | C≡C-1-(Me)cycPr |
| 1436 | 6-CH$_3$ | CF$_3$ | C≡C-2-pyridyl |
| 1437 | 6-CH$_3$ | CF$_3$ | C≡C-3-pyridyl |
| 1438 | 6-CH$_3$ | CF$_3$ | C≡C-4-pyridyl |
| 1439 | 6-CH$_3$ | CF$_3$ | C≡C-2-furanyl |
| 1440 | 6-CH$_3$ | CF$_3$ | C≡C-3-furanyl |
| 1441 | 6-CH$_3$ | CF$_3$ | C≡C-2-thienyl |
| 1442 | 6-CH$_3$ | CF$_3$ | C≡C-3-thienyl |
| 1443 | 6-CH$_3$ | CF$_3$ | CH=CH—Et |
| 1444 | 6-CH$_3$ | CF$_3$ | CH=CH-iPr |
| 1445 | 6-CH$_3$ | CF$_3$ | CH=CH-cycPr |
| 1446 | 6-CH$_3$ | CF$_3$ | CH=CH-1-(Me)cycPr |
| 1447 | 6-CH$_3$ | CF$_3$ | CH=CH-2-pyridyl |
| 1448 | 6-CH$_3$ | CF$_3$ | CH=CH-3-pyridyl |
| 1449 | 6-CH$_3$ | CF$_3$ | CH=CH-4-pyridyl |
| 1450 | 6-CH$_3$ | CF$_3$ | CH=CH-2-furanyl |
| 1451 | 6-CH$_3$ | CF$_3$ | CH=CH-3-furanyl |
| 1452 | 6-CH$_3$ | CF$_3$ | CH=CH-2-thienyl |
| 1453 | 6-CH$_3$ | CF$_3$ | CH=CH-3-thienyl |
| 1454 | 6-CH$_3$ | CF$_3$ | CH$_2$—C≡C-cycPr |
| 1455 | 6-CH$_3$ | CF$_3$ | CH$_2$—C≡C-2-furanyl |
| 1456 | 6-CH$_3$ | CF$_3$ | CH$_2$CH=CH-cycPr |
| 1457 | 6-CH$_3$ | CF$_3$ | CH$_2$CH=CH-2-furanyl |
| 1458 | 6-CH$_3$ | CF$_3$ | CH=CHCH$_2$-cycPr |
| 1459 | 6-CH$_3$ | CF$_3$ | CH=CHCH$_2$-2-furanyl |
| 1460 | 6-OCH$_3$ | CF$_3$ | CH$_2$CH$_2$CH$_3$ |
| 1461 | 6-OCH$_3$ | CF$_3$ | CH$_2$CH$_2$CH$_2$CH$_3$ |
| 1462 | 6-OCH$_3$ | CF$_3$ | CH$_2$CH$_2$CH$_2$CH$_2$CH$_3$ |
| 1463 | 6-OCH$_3$ | CF$_3$ | CH$_2$CH$_2$CH(CH$_3$)$_2$ |
| 1464 | 6-OCH$_3$ | CF$_3$ | CH$_2$CH$_2$-tBu |
| 1465 | 6-OCH$_3$ | CF$_3$ | CH$_2$-cycPr |
| 1466 | 6-OCH$_3$ | CF$_3$ | CH$_2$—Ph |
| 1467 | 6-OCH$_3$ | CF$_3$ | CH$_2$-2-Pyridyl |
| 1478 | 6-OCH$_3$ | CF$_3$ | CH$_2$-3-Pyridyl |
| 1479 | 6-OCH$_3$ | CF$_3$ | CH$_2$-4-Pyridyl |
| 1470 | 6-OCH$_3$ | CF$_3$ | CH$_2$-2-furanyl |
| 1471 | 6-OCH$_3$ | CF$_3$ | CH$_2$-3-furanyl |
| 1472 | 6-OCH$_3$ | CF$_3$ | CH$_2$-2-thienyl |
| 1473 | 6-OCH$_3$ | CF$_3$ | CH$_2$-3-thienyl |
| 1474 | 6-OCH$_3$ | CF$_3$ | CH$_2$CH$_2$-cycPr |
| 1475 | 6-OCH$_3$ | CF$_3$ | CH$_2$CH$_2$—Ph |
| 1476 | 6-OCH$_3$ | CF$_3$ | CH$_2$CH$_2$-2-Pyridyl |
| 1477 | 6-OCH$_3$ | CF$_3$ | CH$_2$CH$_2$-3-Pyridyl |
| 1488 | 6-OCH$_3$ | CF$_3$ | CH$_2$CH$_2$-4-Pyridyl |
| 1489 | 6-OCH$_3$ | CF$_3$ | CH$_2$CH$_2$-2-furanyl |
| 1480 | 6-OCH$_3$ | CF$_3$ | CH$_2$CH$_2$-3-furanyl |
| 1481 | 6-OCH$_3$ | CF$_3$ | CH$_2$CH$_2$-2-thienyl |
| 1482 | 6-OCH$_3$ | CF$_3$ | CH$_2$CH$_2$-3-thienyl |
| 1483 | 6-OCH$_3$ | CF$_3$ | C≡C—Et |
| 1484 | 6-OCH$_3$ | CF$_3$ | C≡C-iPr |
| 1485 | 6-OCH$_3$ | CF$_3$ | C≡C-cycPr |
| 1486 | 6-OCH$_3$ | CF$_3$ | C≡C-1-(Me)cycPr |
| 1487 | 6-OCH$_3$ | CF$_3$ | C≡C-2-pyridyl |
| 1488 | 6-OCH$_3$ | CF$_3$ | C≡C-3-pyridyl |
| 1489 | 6-OCH$_3$ | CF$_3$ | C≡C-4-pyridyl |
| 1490 | 6-OCH$_3$ | CF$_3$ | C≡C-2-furanyl |
| 1491 | 6-OCH$_3$ | CF$_3$ | C≡C-3-furanyl |
| 1492 | 6-OCH$_3$ | CF$_3$ | C≡C-2-thienyl |
| 1493 | 6-OCH$_3$ | CF$_3$ | C≡C-3-thienyl |
| 1494 | 6-OCH$_3$ | CF$_3$ | CH=CH—Et |
| 1495 | 6-OCH$_3$ | CF$_3$ | CH=CH-iPr |
| 1496 | 6-OCH$_3$ | CF$_3$ | CH=CH-cycPr |
| 1497 | 6-OCH$_3$ | CF$_3$ | CH=CH-1-(Me)cycPr |
| 1498 | 6-OCH$_3$ | CF$_3$ | CH=CH-2-pyridyl |
| 1499 | 6-OCH$_3$ | CF$_3$ | CH=CH-3-pyridyl |
| 1500 | 6-OCH$_3$ | CF$_3$ | CH=CH-4-pyridyl |
| 1501 | 6-OCH$_3$ | CF$_3$ | CH=CH-2-furanyl |
| 1502 | 6-OCH$_3$ | CF$_3$ | CH=CH-3-furanyl |
| 1503 | 6-OCH$_3$ | CF$_3$ | CH=CH-2-thienyl |
| 1504 | 6-OCH$_3$ | CF$_3$ | CH=CH-3-thienyl |
| 1505 | 6-OCH$_3$ | CF$_3$ | CH$_2$—C≡C-cycPr |
| 1506 | 6-OCH$_3$ | CF$_3$ | CH$_2$—C≡C-2-furanyl |
| 1507 | 6-OCH$_3$ | CF$_3$ | CH$_2$CH=CH-cycPr |
| 1508 | 6-OCH$_3$ | CF$_3$ | CH$_2$CH=CH-2-furanyl |
| 1509 | 6-OCH$_3$ | CF$_3$ | CH=CHCH$_2$-cycPr |
| 1510 | 6-OCH$_3$ | CF$_3$ | CH=CHCH$_2$-2-furanyl |
| 1511 | 5,6-OCH$_2$O— | CF$_3$ | CH$_2$CH$_2$CH$_3$ |
| 1512 | 5,6-OCH$_2$O— | CF$_3$ | CH$_2$CH$_2$CH$_2$CH$_3$ |
| 1513 | 5,6-OCH$_2$O— | CF$_3$ | CH$_2$CH$_2$CH$_2$CH$_2$CH$_3$ |
| 1514 | 5,6-OCH$_2$O— | CF$_3$ | CH$_2$CH$_2$CH(CH$_3$)$_2$ |
| 1515 | 5,6-OCH$_2$O— | CF$_3$ | CH$_2$CH$_2$-tBu |
| 1516 | 5,6-OCH$_2$O— | CF$_3$ | CH$_2$-cycPr |
| 1517 | 5,6-OCH$_2$O— | CF$_3$ | CH$_2$—Ph |
| 1518 | 5,6-OCH$_2$O— | CF$_3$ | CH$_2$-2-Pyridyl |
| 1519 | 5,6-OCH$_2$O— | CF$_3$ | CH$_2$-3-Pyridyl |
| 1520 | 5,6-OCH$_2$O— | CF$_3$ | CH$_2$-4-Pyridyl |
| 1521 | 5,6-OCH$_2$O— | CF$_3$ | CH$_2$-2-furanyl |
| 1522 | 5,6-OCH$_2$O— | CF$_3$ | CH$_2$-3-furanyl |
| 1523 | 5,6-OCH$_2$O— | CF$_3$ | CH$_2$-2-thienyl |
| 1524 | 5,6-OCH$_2$O— | CF$_3$ | CH$_2$-3-thienyl |
| 1525 | 5,6-OCH$_2$O— | CF$_3$ | CH$_2$CH$_2$-cycPr |
| 1526 | 5,6-OCH$_2$O— | CF$_3$ | CH$_2$CH$_2$—Ph |
| 1527 | 5,6-OCH$_2$O— | CF$_3$ | CH$_2$CH$_2$-2-Pyridyl |
| 1528 | 5,6-OCH$_2$O— | CF$_3$ | CH$_2$CH$_2$-3-Pyridyl |
| 1529 | 5,6-OCH$_2$O— | CF$_3$ | CH$_2$CH$_2$-4-Pyridyl |
| 1530 | 5,6-OCH$_2$O— | CF$_3$ | CH$_2$CH$_2$-2-furanyl |
| 1531 | 5,6-OCH$_2$O— | CF$_3$ | CH$_2$CH$_2$-3-furanyl |

TABLE 2-continued

| | | | |
|---|---|---|---|
| 1532 | 5,6-OCH$_2$O— | CF$_3$ | CH$_2$CH$_2$-2-thienyl |
| 1533 | 5,6-OCH$_2$O— | CF$_3$ | CH$_2$CH$_2$-3-thienyl |
| 1534 | 5,6-OCH$_2$O— | CF$_3$ | C≡C—Et |
| 1535 | 5,6-OCH$_2$O— | CF$_3$ | C≡C-iPr |
| 1536 | 5,6-OCH$_2$O— | CF$_3$ | C≡C-cycPr |
| 1537 | 5,6-OCH$_2$O— | CF$_3$ | C≡C-1-(Me)cycPr |
| 1538 | 5,6-OCH$_2$O— | CF$_3$ | C≡C-2-pyridyl |
| 1539 | 5,6-OCH$_2$O— | CF$_3$ | C≡C-3-pyridyl |
| 1540 | 5,6-OCH$_2$O— | CF$_3$ | C≡C-4-pyridyl |
| 1541 | 5,6-OCH$_2$O— | CF$_3$ | C≡C-2-furanyl |
| 1542 | 5,6-OCH$_2$O— | CF$_3$ | C≡C-3-furanyl |
| 1543 | 5,6-OCH$_2$O— | CF$_3$ | C≡C-2-thienyl |
| 1544 | 5,6-OCH$_2$O— | CF$_3$ | C≡C-3-thienyl |
| 1545 | 5,6-OCH$_2$O— | CF$_3$ | CH=CH—Et |
| 1546 | 5,6-OCH$_2$O— | CF$_3$ | CH=CH-iPr |
| 1547 | 5,6-OCH$_2$O— | CF$_3$ | CH=CH-cycPr |
| 1548 | 5,6-OCH$_2$O— | CF$_3$ | CH=CH-1-(Me)cycPr |
| 1549 | 5,6-OCH$_2$O— | CF$_3$ | CH=CH-2-pyridyl |
| 1550 | 5,6-OCH$_2$O— | CF$_3$ | CH=CH-3-pyridyl |
| 1551 | 5,6-OCH$_2$O— | CF$_3$ | CH=CH-4-pyridyl |
| 1552 | 5,6-OCH$_2$O— | CF$_3$ | CH=CH-2-furanyl |
| 1553 | 5,6-OCH$_2$O— | CF$_3$ | CH=CH-3-furanyl |
| 1554 | 5,6-OCH$_2$O— | CF$_3$ | CH=CH-2-thienyl |
| 1555 | 5,6-OCH$_2$O— | CF$_3$ | CH=CH-3-thienyl |
| 1556 | 5,6-OCH$_2$O— | CF$_3$ | CH$_2$—C≡C-cycPr |
| 1557 | 5,6-OCH$_2$O— | CF$_3$ | CH$_2$—C≡C-2-furanyl |
| 1558 | 5,6-OCH$_2$O— | CF$_3$ | CH$_2$CH=CH-cycPr |
| 1559 | 5,6-OCH$_2$O— | CF$_3$ | CH$_2$CH=CH-2-furanyl |
| 1560 | 5,6-OCH$_2$O— | CF$_3$ | CH=CHCH$_2$-cycPr |
| 1561 | 5,6-OCH$_2$O— | CF$_3$ | CH=CHCH$_2$-2-furanyl |
| 1601 | 5-Cl | CF$_2$CF$_3$ | CH$_2$CH$_2$CH$_3$ |
| 1602 | 5-Cl | CF$_2$CF$_3$ | CH$_2$CH$_2$CH$_2$CH$_3$ |
| 1603 | 5-Cl | CF$_2$CF$_3$ | CH$_2$CH$_2$CH$_2$CH$_2$CH$_3$ |
| 1604 | 5-Cl | CF$_2$CF$_3$ | CH$_2$CH$_2$CH(CH$_3$)$_2$ |
| 1605 | 5-Cl | CF$_2$CF$_3$ | CH$_2$CH$_2$-tBu |
| 1606 | 5-Cl | CF$_2$CF$_3$ | CH$_2$-cycPr |
| 1607 | 5-Cl | CF$_2$CF$_3$ | CH$_2$—Ph |
| 1608 | 5-Cl | CF$_2$CF$_3$ | CH$_2$-2-Pyridyl |
| 1609 | 5-Cl | CF$_2$CF$_3$ | CH$_2$-3-Pyridyl |
| 1610 | 5-Cl | CF$_2$CF$_3$ | CH$_2$-4-Pyridyl |
| 1611 | 5-Cl | CF$_2$CF$_3$ | CH$_2$-2-furanyl |
| 1612 | 5-Cl | CF$_2$CF$_3$ | CH$_2$-3-furanyl |
| 1613 | 5-Cl | CF$_2$CF$_3$ | CH$_2$-2-thienyl |
| 1614 | 5-Cl | CF$_2$CF$_3$ | CH$_2$-3-thienyl |
| 1615 | 5-Cl | CF$_2$CF$_3$ | CH$_2$CH$_2$-cycPr |
| 1616 | 5-Cl | CF$_2$CF$_3$ | CH$_2$CH$_2$—Ph |
| 1617 | 5-Cl | CF$_2$CF$_3$ | CH$_2$CH$_2$-2-Pyridyl |
| 1618 | 5-Cl | CF$_2$CF$_3$ | CH$_2$CH$_2$-3-Pyridyl |
| 1619 | 5-Cl | CF$_2$CF$_3$ | CH$_2$CH$_2$-4-Pyridyl |
| 1620 | 5-Cl | CF$_2$CF$_3$ | CH$_2$CH$_2$-2-furanyl |
| 1621 | 5-Cl | CF$_2$CF$_3$ | CH$_2$CH$_2$-3-furanyl |
| 1622 | 5-Cl | CF$_2$CF$_3$ | CH$_2$CH$_2$-2-thienyl |
| 1623 | 5-Cl | CF$_2$CF$_3$ | CH$_2$CH$_2$-3-thienyl |
| 1624 | 5-Cl | CF$_2$CF$_3$ | C≡C—Et |
| 1625 | 5-Cl | CF$_2$CF$_3$ | C≡C-iPr |
| 1626 | 5-Cl | CF$_2$CF$_3$ | C≡C-cycPr |
| 1627 | 5-Cl | CF$_2$CF$_3$ | C≡C-1-(Me)cycPr |
| 1628 | 5-Cl | CF$_2$CF$_3$ | C≡C-2-pyridyl |
| 1629 | 5-Cl | CF$_2$CF$_3$ | C≡C-3-pyridyl |
| 1630 | 5-Cl | CF$_2$CF$_3$ | C≡C-4-pyridyl |
| 1631 | 5-Cl | CF$_2$CF$_3$ | C≡C-2-furanyl |
| 1632 | 5-Cl | CF$_2$CF$_3$ | C≡C-3-furanyl |
| 1633 | 5-Cl | CF$_2$CF$_3$ | C≡C-2-thienyl |
| 1634 | 5-Cl | CF$_2$CF$_3$ | C≡C-3-thienyl |
| 1635 | 5-Cl | CF$_2$CF$_3$ | CH=CH—Et |
| 1636 | 5-Cl | CF$_2$CF$_3$ | CH=CH-iPr |
| 1637 | 5-Cl | CF$_2$CF$_3$ | CH=CH-cycPr |
| 1638 | 5-Cl | CF$_2$CF$_3$ | CH=CH-1-(Me)cycPr |
| 1639 | 5-Cl | CF$_2$CF$_3$ | CH=CH-2-pyridyl |
| 1640 | 5-Cl | CF$_2$CF$_3$ | CH=CH-3-pyridyl |
| 1641 | 5-Cl | CF$_2$CF$_3$ | CH=CH-4-pyridyl |
| 1642 | 5-Cl | CF$_2$CF$_3$ | CH=CH-2-furanyl |
| 1643 | 5-Cl | CF$_2$CF$_3$ | CH=CH-3-furanyl |
| 1644 | 5-Cl | CF$_2$CF$_3$ | CH=CH-2-thienyl |
| 1645 | 5-Cl | CF$_2$CF$_3$ | CH=CH-3-thienyl |
| 1646 | 5-Cl | CF$_2$CF$_3$ | CH$_2$—C≡C-cycPr |
| 1647 | 5-Cl | CF$_2$CF$_3$ | CH$_2$—C≡C-2-furanyl |
| 1648 | 5-Cl | CF$_2$CF$_3$ | CH$_2$CH=CH-cycPr |
| 1649 | 5-Cl | CF$_2$CF$_3$ | CH$_2$CH=CH-2-furanyl |
| 1650 | 5-Cl | CF$_2$CF$_3$ | CH=CHCH$_2$-cycPr |
| 1651 | 5-Cl | CF$_2$CF$_3$ | CH=CHCH$_2$-2-furanyl |
| 1652 | 6-Cl | CF$_2$CF$_3$ | CH$_2$CH$_2$CH$_3$ |
| 1653 | 6-Cl | CF$_2$CF$_3$ | CH$_2$CH$_2$CH$_2$CH$_3$ |
| 1654 | 6-Cl | CF$_2$CF$_3$ | CH$_2$CH$_2$CH$_2$CH$_2$CH$_3$ |
| 1655 | 6-Cl | CF$_2$CF$_3$ | CH$_2$CH$_2$CH(CH$_3$)$_2$ |
| 1656 | 6-Cl | CF$_2$CF$_3$ | CH$_2$CH$_2$-tBu |
| 1657 | 6-Cl | CF$_2$CF$_3$ | CH$_2$-cycPr |
| 1658 | 6-Cl | CF$_2$CF$_3$ | CH$_2$—Ph |
| 1659 | 6-Cl | CF$_2$CF$_3$ | CH$_2$-2-Pyridyl |
| 1660 | 6-Cl | CF$_2$CF$_3$ | CH$_2$-3-Pyridyl |
| 1661 | 6-Cl | CF$_2$CF$_3$ | CH$_2$-4-Pyridyl |
| 1662 | 6-Cl | CF$_2$CF$_3$ | CH$_2$-2-furanyl |
| 1663 | 6-Cl | CF$_2$CF$_3$ | CH$_2$-3-furanyl |
| 1664 | 6-Cl | CF$_2$CF$_3$ | CH$_2$-2-thienyl |
| 1665 | 6-Cl | CF$_2$CF$_3$ | CH$_2$-3-thienyl |
| 1666 | 6-Cl | CF$_2$CF$_3$ | CH$_2$CH$_2$-cycPr |
| 1667 | 6-Cl | CF$_2$CF$_3$ | CH$_2$CH$_2$—Ph |
| 1668 | 6-Cl | CF$_2$CF$_3$ | CH$_2$CH$_2$-2-Pyridyl |
| 1669 | 6-Cl | CF$_2$CF$_3$ | CH$_2$CH$_2$-3-Pyridyl |
| 1670 | 6-Cl | CF$_2$CF$_3$ | CH$_2$CH$_2$-4-Pyridyl |
| 1671 | 6-Cl | CF$_2$CF$_3$ | CH$_2$CH$_2$-2-furanyl |
| 1672 | 6-Cl | CF$_2$CF$_3$ | CH$_2$CH$_2$-3-furanyl |
| 1673 | 6-Cl | CF$_2$CF$_3$ | CH$_2$CH$_2$-2-thienyl |
| 1674 | 6-Cl | CF$_2$CF$_3$ | CH$_2$CH$_2$-3-thienyl |
| 1675 | 6-Cl | CF$_2$CF$_3$ | C≡C—Et |
| 1676 | 6-Cl | CF$_2$CF$_3$ | C≡C-iPr |
| 1677 | 6-Cl | CF$_2$CF$_3$ | C≡C-cycPr |
| 1678 | 6-Cl | CF$_2$CF$_3$ | C≡C-1-(Me)cycPr |
| 1679 | 6-Cl | CF$_2$CF$_3$ | C≡C-2-pyridyl |
| 1680 | 6-Cl | CF$_2$CF$_3$ | C≡C-3-pyridyl |
| 1681 | 6-Cl | CF$_2$CF$_3$ | C≡C-4-pyridyl |
| 1682 | 6-Cl | CF$_2$CF$_3$ | C≡C-2-furanyl |
| 1683 | 6-Cl | CF$_2$CF$_3$ | C≡C-3-furanyl |
| 1684 | 6-Cl | CF$_2$CF$_3$ | C≡C-2-thienyl |
| 1685 | 6-Cl | CF$_2$CF$_3$ | C≡C-3-thienyl |
| 1686 | 6-Cl | CF$_2$CF$_3$ | CH=CH—Et |
| 1687 | 6-Cl | CF$_2$CF$_3$ | CH=CH-iPr |
| 1688 | 6-Cl | CF$_2$CF$_3$ | CH=CH-cycPr |
| 1689 | 6-Cl | CF$_2$CF$_3$ | CH=CH-1-(Me)cycPr |
| 1690 | 6-Cl | CF$_2$CF$_3$ | CH=CH-2-pyridyl |
| 1691 | 6-Cl | CF$_2$CF$_3$ | CH=CH-3-pyridyl |
| 1692 | 6-Cl | CF$_2$CF$_3$ | CH=CH-4-pyridyl |
| 1693 | 6-Cl | CF$_2$CF$_3$ | CH=CH-2-furanyl |
| 1694 | 6-Cl | CF$_2$CF$_3$ | CH=CH-3-furanyl |
| 1695 | 6-Cl | CF$_2$CF$_3$ | CH=CH-2-thienyl |
| 1696 | 6-Cl | CF$_2$CF$_3$ | CH=CH-3-thienyl |
| 1697 | 6-Cl | CF$_2$CF$_3$ | CH$_2$—C≡C-cycPr |
| 1698 | 6-Cl | CF$_2$CF$_3$ | CH$_2$—C≡C-2-furanyl |
| 1699 | 6-Cl | CF$_2$CF$_3$ | CH$_2$CH=CH-cycPr |
| 1700 | 6-Cl | CF$_2$CF$_3$ | CH$_2$CH=CH-2-furanyl |
| 1701 | 6-Cl | CF$_2$CF$_3$ | CH=CHCH$_2$-cycPr |
| 1702 | 6-Cl | CF$_2$CF$_3$ | CH=CHCH$_2$-2-furanyl |
| 1703 | 5-F | CF$_2$CF$_3$ | CH$_2$CH$_2$CH$_3$ |
| 1704 | 5-F | CF$_2$CF$_3$ | CH$_2$CH$_2$CH$_2$CH$_3$ |
| 1705 | 5-F | CF$_2$CF$_3$ | CH$_2$CH$_2$CH$_2$CH$_2$CH$_3$ |
| 1706 | 5-F | CF$_2$CF$_3$ | CH$_2$CH$_2$CH(CH$_3$)$_2$ |
| 1707 | 5-F | CF$_2$CF$_3$ | CH$_2$CH$_2$-tBu |
| 1708 | 5-F | CF$_2$CF$_3$ | CH$_2$-cycPr |
| 1709 | 5-F | CF$_2$CF$_3$ | CH$_2$—Ph |
| 1710 | 5-F | CF$_2$CF$_3$ | CH$_2$-2-Pyridyl |
| 1711 | 5-F | CF$_2$CF$_3$ | CH$_2$-3-Pyridyl |
| 1712 | 5-F | CF$_2$CF$_3$ | CH$_2$-4-Pyridyl |
| 1713 | 5-F | CF$_2$CF$_3$ | CH$_2$-2-furanyl |
| 1714 | 5-F | CF$_2$CF$_3$ | CH$_2$-3-furanyl |
| 1715 | 5-F | CF$_2$CF$_3$ | CH$_2$-2-thienyl |
| 1716 | 5-F | CF$_2$CF$_3$ | CH$_2$-3-thienyl |
| 1717 | 5-F | CF$_2$CF$_3$ | CH$_2$CH$_2$-cycPr |
| 1718 | 5-F | CF$_2$CF$_3$ | CH$_2$CH$_2$—Ph |
| 1719 | 5-F | CF$_2$CF$_3$ | CH$_2$CH$_2$-2-Pyridyl |
| 1720 | 5-F | CF$_2$CF$_3$ | CH$_2$CH$_2$-3-Pyridyl |
| 1721 | 5-F | CF$_2$CF$_3$ | CH$_2$CH$_2$-4-Pyridyl |
| 1722 | 5-F | CF$_2$CF$_3$ | CH$_2$CH$_2$-2-furanyl |
| 1723 | 5-F | CF$_2$CF$_3$ | CH$_2$CH$_2$-3-furanyl |
| 1724 | 5-F | CF$_2$CF$_3$ | CH$_2$CH$_2$-2-thienyl |
| 1725 | 5-F | CF$_2$CF$_3$ | CH$_2$CH$_2$-3-thienyl |
| 1726 | 5-F | CF$_2$CF$_3$ | C≡C—Et |
| 1727 | 5-F | CF$_2$CF$_3$ | C≡C-iPr |
| 1728 | 5-F | CF$_2$CF$_3$ | C≡C-cycPr |

TABLE 2-continued

| | | | |
|---|---|---|---|
| 1729 | 5-F | CF$_2$CF$_3$ | C≡C-1-(Me)cycPr |
| 1730 | 5-F | CF$_2$CF$_3$ | C≡C-2-pyridyl |
| 1731 | 5-F | CF$_2$CF$_3$ | C≡C-3-pyridyl |
| 1732 | 5-F | CF$_2$CF$_3$ | C≡C-4-pyridyl |
| 1733 | 5-F | CF$_2$CF$_3$ | C≡C-2-furanyl |
| 1734 | 5-F | CF$_2$CF$_3$ | C≡C-3-furanyl |
| 1735 | 5-F | CF$_2$CF$_3$ | C≡C-2-thienyl |
| 1736 | 5-F | CF$_2$CF$_3$ | C≡C-3-thienyl |
| 1737 | 5-F | CF$_2$CF$_3$ | CH=CH—Et |
| 1738 | 5-F | CF$_2$CF$_3$ | CH=CH-iPr |
| 1739 | 5-F | CF$_2$CF$_3$ | CH=CH-cycPr |
| 1740 | 5-F | CF$_2$CF$_3$ | CH=CH-1-(Me)cycPr |
| 1741 | 5-F | CF$_2$CF$_3$ | CH=CH-2-pyridyl |
| 1742 | 5-F | CF$_2$CF$_3$ | CH=CH-3-pyridyl |
| 1743 | 5-F | CF$_2$CF$_3$ | CH=CH-4-pyridyl |
| 1744 | 5-F | CF$_2$CF$_3$ | CH=CH-2-furanyl |
| 1745 | 5-F | CF$_2$CF$_3$ | CH=CH-3-furanyl |
| 1746 | 5-F | CF$_2$CF$_3$ | CH=CH-2-thienyl |
| 1747 | 5-F | CF$_2$CF$_3$ | CH=CH-3-thienyl |
| 1748 | 5-F | CF$_2$CF$_3$ | CH$_2$—C≡C-cycPr |
| 1749 | 5-F | CF$_2$CF$_3$ | CH$_2$—C≡C-2-furanyl |
| 1750 | 5-F | CF$_2$CF$_3$ | CH$_2$CH=CH-cycPr |
| 1751 | 5-F | CF$_2$CF$_3$ | CH$_2$CH=CH-2-furanyl |
| 1752 | 5-F | CF$_2$CF$_3$ | CH=CHCH$_2$-cycPr |
| 1753 | 5-F | CF$_2$CF$_3$ | CH=CHCH$_2$-2-furanyl |
| 1754 | 6-F | CF$_2$CF$_3$ | CH$_2$CH$_2$CH$_3$ |
| 1755 | 6-F | CF$_2$CF$_3$ | CH$_2$CH$_2$CH$_2$CH$_3$ |
| 1756 | 6-F | CF$_2$CF$_3$ | CH$_2$CH$_2$CH$_2$CH$_2$CH$_3$ |
| 1757 | 6-F | CF$_2$CF$_3$ | CH$_2$CH$_2$CH(CH$_3$)$_2$ |
| 1758 | 6-F | CF$_2$CF$_3$ | CH$_2$CH$_2$-tBu |
| 1759 | 6-F | CF$_2$CF$_3$ | CH$_2$-cycPr |
| 1760 | 6-F | CF$_2$CF$_3$ | CH$_2$—Ph |
| 1761 | 6-F | CF$_2$CF$_3$ | CH$_2$-2-Pyridyl |
| 1762 | 6-F | CF$_2$CF$_3$ | CH$_2$-3-Pyridyl |
| 1763 | 6-F | CF$_2$CF$_3$ | CH$_2$-4-Pyridyl |
| 1764 | 6-F | CF$_2$CF$_3$ | CH$_2$-2-furanyl |
| 1765 | 6-F | CF$_2$CF$_3$ | CH$_2$-3-furanyl |
| 1766 | 6-F | CF$_2$CF$_3$ | CH$_2$-2-thienyl |
| 1767 | 6-F | CF$_2$CF$_3$ | CH$_2$-3-thienyl |
| 1768 | 6-F | CF$_2$CF$_3$ | CH$_2$CH$_2$-cycPr |
| 1769 | 6-F | CF$_2$CF$_3$ | CH$_2$CH$_2$—Ph |
| 1770 | 6-F | CF$_2$CF$_3$ | CH$_2$CH$_2$-2-Pyridyl |
| 1771 | 6-F | CF$_2$CF$_3$ | CH$_2$CH$_2$-3-Pyridyl |
| 1772 | 6-F | CF$_2$CF$_3$ | CH$_2$CH$_2$-4-Pyridyl |
| 1773 | 6-F | CF$_2$CF$_3$ | CH$_2$CH$_2$-2-furanyl |
| 1774 | 6-F | CF$_2$CF$_3$ | CH$_2$CH$_2$-3-furanyl |
| 1775 | 6-F | CF$_2$CF$_3$ | CH$_2$CH$_2$-2-thienyl |
| 1776 | 6-F | CF$_2$CF$_3$ | CH$_2$CH$_2$-3-thienyl |
| 1777 | 6-F | CF$_2$CF$_3$ | C≡C—Et |
| 1778 | 6-F | CF$_2$CF$_3$ | C≡C-iPr |
| 1779 | 6-F | CF$_2$CF$_3$ | C≡C-cycPr |
| 1780 | 6-F | CF$_2$CF$_3$ | C≡C-1-(Me)cycPr |
| 1781 | 6-F | CF$_2$CF$_3$ | C≡C-2-pyridyl |
| 1782 | 6-F | CF$_2$CF$_3$ | C≡C-3-pyridyl |
| 1783 | 6-F | CF$_2$CF$_3$ | C≡C-4-pyridyl |
| 1784 | 6-F | CF$_2$CF$_3$ | C≡C-2-furanyl |
| 1785 | 6-F | CF$_2$CF$_3$ | C≡C-3-furanyl |
| 1786 | 6-F | CF$_2$CF$_3$ | C≡C-2-thienyl |
| 1787 | 6-F | CF$_2$CF$_3$ | C≡C-3-thienyl |
| 1788 | 6-F | CF$_2$CF$_3$ | CH=CH—Et |
| 1789 | 6-F | CF$_2$CF$_3$ | CH=CH-iPr |
| 1790 | 6-F | CF$_2$CF$_3$ | CH=CH-cycPr |
| 1791 | 6-F | CF$_2$CF$_3$ | CH=CH-1-(Me)cycPr |
| 1792 | 6-F | CF$_2$CF$_3$ | CH=CH-2-pyridyl |
| 1793 | 6-F | CF$_2$CF$_3$ | CH=CH-3-pyridyl |
| 1794 | 6-F | CF$_2$CF$_3$ | CH=CH-4-pyridyl |
| 1795 | 6-F | CF$_2$CF$_3$ | CH=CH-2-furanyl |
| 1796 | 6-F | CF$_2$CF$_3$ | CH=CH-3-furanyl |
| 1797 | 6-F | CF$_2$CF$_3$ | CH=CH-2-thienyl |
| 1798 | 6-F | CF$_2$CF$_3$ | CH=CH-3-thienyl |
| 1799 | 6-F | CF$_2$CF$_3$ | CH$_2$—C≡C-cycPr |
| 1800 | 6-F | CF$_2$CF$_3$ | CH$_2$—C≡C-2-furanyl |
| 1801 | 6-F | CF$_2$CF$_3$ | CH$_2$CH=CH-cycPr |
| 1802 | 6-F | CF$_2$CF$_3$ | CH$_2$CH=CH-2-furanyl |
| 1803 | 6-F | CF$_2$CF$_3$ | CH=CHCH$_2$-cycPr |
| 1804 | 6-F | CF$_2$CF$_3$ | CH=CHCH$_2$-2-furanyl |
| 1805 | 5,6-diCl | CF$_2$CF$_3$ | CH$_2$CH$_2$CH$_3$ |
| 1806 | 5,6-diCl | CF$_2$CF$_3$ | CH$_2$CH$_2$CH$_2$CH$_3$ |
| 1807 | 5,6-diCl | CF$_2$CF$_3$ | CH$_2$CH$_2$CH$_2$CH$_2$CH$_3$ |
| 1808 | 5,6-diCl | CF$_2$CF$_3$ | CH$_2$CH$_2$CH(CH$_3$)$_2$ |
| 1809 | 5,6-diCl | CF$_2$CF$_3$ | CH$_2$CH$_2$-tBu |
| 1810 | 5,6-diCl | CF$_2$CF$_3$ | CH$_2$-cycPr |
| 1811 | 5,6-diCl | CF$_2$CF$_3$ | CH$_2$—Ph |
| 1812 | 5,6-diCl | CF$_2$CF$_3$ | CH$_2$-2-Pyridyl |
| 1813 | 5,6-diCl | CF$_2$CF$_3$ | CH$_2$-3-Pyridyl |
| 1814 | 5,6-diCl | CF$_2$CF$_3$ | CH$_2$-4-Pyridyl |
| 1815 | 5,6-diCl | CF$_2$CF$_3$ | CH$_2$-2-furanyl |
| 1816 | 5,6-diCl | CF$_2$CF$_3$ | CH$_2$-3-furanyl |
| 1817 | 5,6-diCl | CF$_2$CF$_3$ | CH$_2$-2-thienyl |
| 1818 | 5,6-diCl | CF$_2$CF$_3$ | CH$_2$-3-thienyl |
| 1819 | 5,6-diCl | CF$_2$CF$_3$ | CH$_2$CH$_2$-cycPr |
| 1820 | 5,6-diCl | CF$_2$CF$_3$ | CH$_2$CH$_2$—Ph |
| 1821 | 5,6-diCl | CF$_2$CF$_3$ | CH$_2$CH$_2$-2-Pyridyl |
| 1822 | 5,6-diCl | CF$_2$CF$_3$ | CH$_2$CH$_2$-3-Pyridyl |
| 1823 | 5,6-diCl | CF$_2$CF$_3$ | CH$_2$CH$_2$-4-Pyridyl |
| 1824 | 5,6-diCl | CF$_2$CF$_3$ | CH$_2$CH$_2$-2-furanyl |
| 1825 | 5,6-diCl | CF$_2$CF$_3$ | CH$_2$CH$_2$-3-furanyl |
| 1826 | 5,6-diCl | CF$_2$CF$_3$ | CH$_2$CH$_2$-2-thienyl |
| 1827 | 5,6-diCl | CF$_2$CF$_3$ | CH$_2$CH$_2$-3-thienyl |
| 1828 | 5,6-diCl | CF$_2$CF$_3$ | C≡C—Et |
| 1829 | 5,6-diCl | CF$_2$CF$_3$ | C≡C-iPr |
| 1830 | 5,6-diCl | CF$_2$CF$_3$ | C≡C-cycPr |
| 1831 | 5,6-diCl | CF$_2$CF$_3$ | C≡C-1-(Me)cycPr |
| 1832 | 5,6-diCl | CF$_2$CF$_3$ | C≡C-2-pyridyl |
| 1833 | 5,6-diCl | CF$_2$CF$_3$ | C≡C-3-pyridyl |
| 1834 | 5,6-diCl | CF$_2$CF$_3$ | C≡C-4-pyridyl |
| 1835 | 5,6-diCl | CF$_2$CF$_3$ | C≡C-2-furanyl |
| 1836 | 5,6-diCl | CF$_2$CF$_3$ | C≡C-3-furanyl |
| 1837 | 5,6-diCl | CF$_2$CF$_3$ | C≡C-2-thienyl |
| 1838 | 5,6-diCl | CF$_2$CF$_3$ | C≡C-3-thienyl |
| 1839 | 5,6-diCl | CF$_2$CF$_3$ | CH=CH—Et |
| 1840 | 5,6-diCl | CF$_2$CF$_3$ | CH=CH-iPr |
| 1841 | 5,6-diCl | CF$_2$CF$_3$ | CH=CH-cycPr |
| 1842 | 5,6-diCl | CF$_2$CF$_3$ | CH=CH-1-(Me)cycPr |
| 1843 | 5,6-diCl | CF$_2$CF$_3$ | CH=CH-2-pyridyl |
| 1844 | 5,6-diCl | CF$_2$CF$_3$ | CH=CH-3-pyridyl |
| 1845 | 5,6-diCl | CF$_2$CF$_3$ | CH=CH-4-pyridyl |
| 1846 | 5,6-diCl | CF$_2$CF$_3$ | CH=CH-2-furanyl |
| 1847 | 5,6-diCl | CF$_2$CF$_3$ | CH=CH-3-furanyl |
| 1848 | 5,6-diCl | CF$_2$CF$_3$ | CH=CH-2-thienyl |
| 1849 | 5,6-diCl | CF$_2$CF$_3$ | CH=CH-3-thienyl |
| 1850 | 5,6-diCl | CF$_2$CF$_3$ | CH$_2$—C≡C-cycPr |
| 1851 | 5,6-diCl | CF$_2$CF$_3$ | CH$_2$—C≡C-2-furanyl |
| 1852 | 5,6-diCl | CF$_2$CF$_3$ | CH$_2$CH=CH-cycPr |
| 1853 | 5,6-diCl | CF$_2$CF$_3$ | CH$_2$CH=CH-2-furanyl |
| 1854 | 5,6-diCl | CF$_2$CF$_3$ | CH=CHCH$_2$-cycPr |
| 1855 | 5,6-diCl | CF$_2$CF$_3$ | CH=CHCH$_2$-2-furanyl |
| 1856 | 5,6-diF | CF$_2$CF$_3$ | CH$_2$CH$_2$CH$_3$ |
| 1857 | 5,6-diF | CF$_2$CF$_3$ | CH$_2$CH$_2$CH$_2$CH$_3$ |
| 1858 | 5,6-diF | CF$_2$CF$_3$ | CH$_2$CH$_2$CH$_2$CH$_2$CH$_3$ |
| 1859 | 5,6-diF | CF$_2$CF$_3$ | CH$_2$CH$_2$CH(CH$_3$)$_2$ |
| 1860 | 5,6-diF | CF$_2$CF$_3$ | CH$_2$CH$_2$-tBu |
| 1861 | 5,6-diF | CF$_2$CF$_3$ | CH$_2$-cycPr |
| 1862 | 5,6-diF | CF$_2$CF$_3$ | CH$_2$—Ph |
| 1863 | 5,6-diF | CF$_2$CF$_3$ | CH$_2$-2-Pyridyl |
| 1864 | 5,6-diF | CF$_2$CF$_3$ | CH$_2$-3-Pyridyl |
| 1865 | 5,6-diF | CF$_2$CF$_3$ | CH$_2$-4-Pyridyl |
| 1866 | 5,6-diF | CF$_2$CF$_3$ | CH$_2$-2-furanyl |
| 1867 | 5,6-diF | CF$_2$CF$_3$ | CH$_2$-3-furanyl |
| 1868 | 5,6-diF | CF$_2$CF$_3$ | CH$_2$-2-thienyl |
| 1869 | 5,6-diF | CF$_2$CF$_3$ | CH$_2$-3-thienyl |
| 1870 | 5,6-diF | CF$_2$CF$_3$ | CH$_2$CH$_2$-cycPr |
| 1871 | 5,6-diF | CF$_2$CF$_3$ | CH$_2$CH$_2$—Ph |
| 1872 | 5,6-diF | CF$_2$CF$_3$ | CH$_2$CH$_2$-2-Pyridyl |
| 1873 | 5,6-diF | CF$_2$CF$_3$ | CH$_2$CH$_2$-3-Pyridyl |
| 1874 | 5,6-diF | CF$_2$CF$_3$ | CH$_2$CH$_2$-4-Pyridyl |
| 1875 | 5,6-diF | CF$_2$CF$_3$ | CH$_2$CH$_2$-2-furanyl |
| 1876 | 5,6-diF | CF$_2$CF$_3$ | CH$_2$CH$_2$-3-furanyl |
| 1877 | 5,6-diF | CF$_2$CF$_3$ | CH$_2$CH$_2$-2-thienyl |
| 1878 | 5,6-diF | CF$_2$CF$_3$ | CH$_2$CH$_2$-3-thienyl |
| 1879 | 5,6-diF | CF$_2$CF$_3$ | C≡C—Et |
| 1880 | 5,6-diF | CF$_2$CF$_3$ | C≡C-iPr |
| 1881 | 5,6-diF | CF$_2$CF$_3$ | C≡C-cycPr |
| 1882 | 5,6-diF | CF$_2$CF$_3$ | C≡C-1-(Me)cycPr |
| 1883 | 5,6-diF | CF$_2$CF$_3$ | C≡C-2-pyridyl |
| 1884 | 5,6-diF | CF$_2$CF$_3$ | C≡C-3-pyridyl |
| 1885 | 5,6-diF | CF$_2$CF$_3$ | C≡C-4-pyridyl |
| 1886 | 5,6-diF | CF$_2$CF$_3$ | C≡C-2-furanyl |

TABLE 2-continued

| | | | |
|---|---|---|---|
| 1887 | 5,6-diF | $CF_2CF_3$ | C≡C-3-furanyl |
| 1888 | 5,6-diF | $CF_2CF_3$ | C≡C-2-thienyl |
| 1889 | 5,6-diF | $CF_2CF_3$ | C≡C-3-thienyl |
| 1890 | 5,6-diF | $CF_2CF_3$ | CH=CH—Et |
| 1891 | 5,6-diF | $CF_2CF_3$ | CH=CH-iPr |
| 1892 | 5,6-diF | $CF_2CF_3$ | CH=CH-cycPr |
| 1893 | 5,6-diF | $CF_2CF_3$ | CH=CH-1-(Me)cycPr |
| 1894 | 5,6-diF | $CF_2CF_3$ | CH=CH-2-pyridyl |
| 1895 | 5,6-diF | $CF_2CF_3$ | CH=CH-3-pyridyl |
| 1896 | 5,6-diF | $CF_2CF_3$ | CH=CH-4-pyridyl |
| 1897 | 5,6-diF | $CF_2CF_3$ | CH=CH-2-furanyl |
| 1898 | 5,6-diF | $CF_2CF_3$ | CH=CH-3-furanyl |
| 1899 | 5,6-diF | $CF_2CF_3$ | CH=CH-2-thienyl |
| 1900 | 5,6-diF | $CF_2CF_3$ | CH=CH-3-thienyl |
| 1901 | 5,6-diF | $CF_2CF_3$ | $CH_2$—C≡C-cycPr |
| 1902 | 5,6-diF | $CF_2CF_3$ | $CH_2$—C≡C-2-furanyl |
| 1903 | 5,6-diF | $CF_2CF_3$ | $CH_2$CH=CH-cycPr |
| 1904 | 5,6-diF | $CF_2CF_3$ | $CH_2$CH=CH-2-furanyl |
| 1905 | 5,6-diF | $CF_2CF_3$ | CH=CHCH$_2$-cycPr |
| 1906 | 5,6-diF | $CF_2CF_3$ | CH=CHCH$_2$-2-furanyl |
| 1907 | 5-Cl, 6-F | $CF_2CF_3$ | $CH_2CH_2CH_3$ |
| 1908 | 5-Cl, 6-F | $CF_2CF_3$ | $CH_2CH_2CH_2CH_3$ |
| 1909 | 5-Cl, 6-F | $CF_2CF_3$ | $CH_2CH_2CH_2CH_2CH_3$ |
| 1910 | 5-Cl, 6-F | $CF_2CF_3$ | $CH_2CH_2CH(CH_3)_2$ |
| 1911 | 5-Cl, 6-F | $CF_2CF_3$ | $CH_2CH_2$-tBu |
| 1912 | 5-Cl, 6-F | $CF_2CF_3$ | $CH_2$-cycPr |
| 1913 | 5-Cl, 6-F | $CF_2CF_3$ | $CH_2$—Ph |
| 1914 | 5-Cl, 6-F | $CF_2CF_3$ | $CH_2$-2-Pyridyl |
| 1915 | 5-Cl, 6-F | $CF_2CF_3$ | $CH_2$-3-Pyridyl |
| 1916 | 5-Cl, 6-F | $CF_2CF_3$ | $CH_2$-4-Pyridyl |
| 1917 | 5-Cl, 6-F | $CF_2CF_3$ | $CH_2$-2-furanyl |
| 1918 | 5-Cl, 6-F | $CF_2CF_3$ | $CH_2$-3-furanyl |
| 1919 | 5-Cl, 6-F | $CF_2CF_3$ | $CH_2$-2-thienyl |
| 1920 | 5-Cl, 6-F | $CF_2CF_3$ | $CH_2$-3-thienyl |
| 1921 | 5-Cl, 6-F | $CF_2CF_3$ | $CH_2CH_2$-cycPr |
| 1922 | 5-Cl, 6-F | $CF_2CF_3$ | $CH_2CH_2$—Ph |
| 1923 | 5-Cl, 6-F | $CF_2CF_3$ | $CH_2CH_2$-2-Pyridyl |
| 1924 | 5-Cl, 6-F | $CF_2CF_3$ | $CH_2CH_2$-3-Pyridyl |
| 1925 | 5-Cl, 6-F | $CF_2CF_3$ | $CH_2CH_2$-4-Pyridyl |
| 1926 | 5-Cl, 6-F | $CF_2CF_3$ | $CH_2CH_2$-2-furanyl |
| 1927 | 5-Cl, 6-F | $CF_2CF_3$ | $CH_2CH_2$-3-furanyl |
| 1928 | 5-Cl, 6-F | $CF_2CF_3$ | $CH_2CH_2$-2-thienyl |
| 1929 | 5-Cl, 6-F | $CF_2CF_3$ | $CH_2CH_2$-3-thienyl |
| 1930 | 5-Cl, 6-F | $CF_2CF_3$ | C≡C—Et |
| 1931 | 5-Cl, 6-F | $CF_2CF_3$ | C≡C-iPr |
| 1932 | 5-Cl, 6-F | $CF_2CF_3$ | C≡C-cycPr |
| 1933 | 5-Cl, 6-F | $CF_2CF_3$ | C≡C-1-(Me)cycPr |
| 1934 | 5-Cl, 6-F | $CF_2CF_3$ | C≡C-2-pyridyl |
| 1935 | 5-Cl, 6-F | $CF_2CF_3$ | C≡C-3-pyridyl |
| 1936 | 5-Cl, 6-F | $CF_2CF_3$ | C≡C-4-pyridyl |
| 1937 | 5-Cl, 6-F | $CF_2CF_3$ | C≡C-2-furanyl |
| 1938 | 5-Cl, 6-F | $CF_2CF_3$ | C≡C-3-furanyl |
| 1939 | 5-Cl, 6-F | $CF_2CF_3$ | C≡C-2-thienyl |
| 1940 | 5-Cl, 6-F | $CF_2CF_3$ | C≡C-3-thienyl |
| 1941 | 5-Cl, 6-F | $CF_2CF_3$ | CH=CH—Et |
| 1942 | 5-Cl, 6-F | $CF_2CF_3$ | CH=CH-iPr |
| 1943 | 5-Cl, 6-F | $CF_2CF_3$ | CH=CH-cycPr |
| 1944 | 5-Cl, 6-F | $CF_2CF_3$ | CH=CH-1-(Me)cycPr |
| 1945 | 5-Cl, 6-F | $CF_2CF_3$ | CH=CH-2-pyridyl |
| 1946 | 5-Cl, 6-F | $CF_2CF_3$ | CH=CH-3-pyridyl |
| 1947 | 5-Cl, 6-F | $CF_2CF_3$ | CH=CH-4-pyridyl |
| 1948 | 5-Cl, 6-F | $CF_2CF_3$ | CH=CH-2-furanyl |
| 1949 | 5-Cl, 6-F | $CF_2CF_3$ | CH=CH-3-furanyl |
| 1950 | 5-Cl, 6-F | $CF_2CF_3$ | CH=CH-2-thienyl |
| 1951 | 5-Cl, 6-F | $CF_2CF_3$ | CH=CH-3-thienyl |
| 1952 | 5-Cl, 6-F | $CF_2CF_3$ | $CH_2$—C≡C-cycPr |
| 1953 | 5-Cl, 6-F | $CF_2CF_3$ | $CH_2$—C≡C-2-furanyl |
| 1954 | 5-Cl, 6-F | $CF_2CF_3$ | $CH_2$CH=CH-cycPr |
| 1955 | 5-Cl, 6-F | $CF_2CF_3$ | $CH_2$CH=CH-2-furanyl |
| 1956 | 5-Cl, 6-F | $CF_2CF_3$ | CH=CHCH$_2$-cycPr |
| 1957 | 5-Cl, 6-F | $CF_2CF_3$ | CH=CHCH$_2$-2-furanyl |
| 1958 | 5-F, 6-Cl | $CF_2CF_3$ | $CH_2CH_2CH_3$ |
| 1959 | 5-F, 6-Cl | $CF_2CF_3$ | $CH_2CH_2CH_2CH_3$ |
| 1960 | 5-F, 6-Cl | $CF_2CF_3$ | $CH_2CH_2CH_2CH_2CH_3$ |
| 1961 | 5-F, 6-Cl | $CF_2CF_3$ | $CH_2CH_2CH(CH_3)_2$ |
| 1962 | 5-F, 6-Cl | $CF_2CF_3$ | $CH_2CH_2$-tBu |
| 1963 | 5-F, 6-Cl | $CF_2CF_3$ | $CH_2$-cycPr |
| 1964 | 5-F, 6-Cl | $CF_2CF_3$ | $CH_2$—Ph |
| 1965 | 5-F, 6-Cl | $CF_2CF_3$ | $CH_2$-2-Pyridyl |
| 1966 | 5-F, 6-Cl | $CF_2CF_3$ | $CH_2$-3-Pyridyl |
| 1967 | 5-F, 6-Cl | $CF_2CF_3$ | $CH_2$-4-Pyridyl |
| 1968 | 5-F, 6-Cl | $CF_2CF_3$ | $CH_2$-2-furanyl |
| 1969 | 5-F, 6-Cl | $CF_2CF_3$ | $CH_2$-3-furanyl |
| 1970 | 5-F, 6-Cl | $CF_2CF_3$ | $CH_2$-2-thienyl |
| 1971 | 5-F, 6-Cl | $CF_2CF_3$ | $CH_2$-3-thienyl |
| 1972 | 5-F, 6-Cl | $CF_2CF_3$ | $CH_2CH_2$-cycPr |
| 1973 | 5-F, 6-Cl | $CF_2CF_3$ | $CH_2CH_2$—Ph |
| 1974 | 5-F, 6-Cl | $CF_2CF_3$ | $CH_2CH_2$-2-Pyridyl |
| 1975 | 5-F, 6-Cl | $CF_2CF_3$ | $CH_2CH_2$-3-Pyridyl |
| 1976 | 5-F, 6-Cl | $CF_2CF_3$ | $CH_2CH_2$-4-Pyridyl |
| 1977 | 5-F, 6-Cl | $CF_2CF_3$ | $CH_2CH_2$-2-furanyl |
| 1978 | 5-F, 6-Cl | $CF_2CF_3$ | $CH_2CH_2$-3-furanyl |
| 1979 | 5-F, 6-Cl | $CF_2CF_3$ | $CH_2CH_2$-2-thienyl |
| 1980 | 5-F, 6-Cl | $CF_2CF_3$ | $CH_2CH_2$-3-thienyl |
| 1981 | 5-F, 6-Cl | $CF_2CF_3$ | C≡C—Et |
| 1982 | 5-F, 6-Cl | $CF_2CF_3$ | C≡C-iPr |
| 1983 | 5-F, 6-Cl | $CF_2CF_3$ | C≡C-cycPr |
| 1984 | 5-F, 6-Cl | $CF_2CF_3$ | C≡C-1-(Me)cycPr |
| 1985 | 5-F, 6-Cl | $CF_2CF_3$ | C≡C-2-pyridyl |
| 1986 | 5-F, 6-Cl | $CF_2CF_3$ | C≡C-3-pyridyl |
| 1987 | 5-F, 6-Cl | $CF_2CF_3$ | C≡C-4-pyridyl |
| 1988 | 5-F, 6-Cl | $CF_2CF_3$ | C≡C-2-furanyl |
| 1989 | 5-F, 6-Cl | $CF_2CF_3$ | C≡C-3-furanyl |
| 1990 | 5-F, 6-Cl | $CF_2CF_3$ | C≡C-2-thienyl |
| 1991 | 5-F, 6-Cl | $CF_2CF_3$ | C≡C-3-thienyl |
| 1992 | 5-F, 6-Cl | $CF_2CF_3$ | CH=CH—Et |
| 1993 | 5-F, 6-Cl | $CF_2CF_3$ | CH=CH-iPr |
| 1994 | 5-F, 6-Cl | $CF_2CF_3$ | CH=CH-cycPr |
| 1995 | 5-F, 6-Cl | $CF_2CF_3$ | CH=CH-1-(Me)cycPr |
| 1996 | 5-F, 6-Cl | $CF_2CF_3$ | CH=CH-2-pyridyl |
| 1997 | 5-F, 6-Cl | $CF_2CF_3$ | CH=CH-3-pyridyl |
| 1998 | 5-F, 6-Cl | $CF_2CF_3$ | CH=CH-4-pyridyl |
| 1999 | 5-F, 6-Cl | $CF_2CF_3$ | CH=CH-2-furanyl |
| 2000 | 5-F, 6-Cl | $CF_2CF_3$ | CH=CH-3-furanyl |
| 2001 | 5-F, 6-Cl | $CF_2CF_3$ | CH=CH-2-thienyl |
| 2002 | 5-F, 6-Cl | $CF_2CF_3$ | CH=CH-3-thienyl |
| 2003 | 5-F, 6-Cl | $CF_2CF_3$ | $CH_2$—C≡C-cycPr |
| 2004 | 5-F, 6-Cl | $CF_2CF_3$ | $CH_2$—C≡C-2-furanyl |
| 2005 | 5-F, 6-Cl | $CF_2CF_3$ | $CH_2$CH=CH-cycPr |
| 2006 | 5-F, 6-Cl | $CF_2CF_3$ | $CH_2$CH=CH-2-furanyl |
| 2007 | 5-F, 6-Cl | $CF_2CF_3$ | CH=CHCH$_2$-cycPr |
| 2008 | 5-F, 6-Cl | $CF_2CF_3$ | CH=CHCH$_2$-2-furanyl |
| 2009 | 6-CH$_3$ | $CF_2CF_3$ | $CH_2CH_2CH_3$ |
| 2010 | 6-CH$_3$ | $CF_2CF_3$ | $CH_2CH_2CH_2CH_3$ |
| 2011 | 6-CH$_3$ | $CF_2CF_3$ | $CH_2CH_2CH_2CH_2CH_3$ |
| 2012 | 6-CH$_3$ | $CF_2CF_3$ | $CH_2CH_2CH(CH_3)_2$ |
| 2013 | 6-CH$_3$ | $CF_2CF_3$ | $CH_2CH_2$-tBu |
| 2014 | 6-CH$_3$ | $CF_2CF_3$ | $CH_2$-cycPr |
| 2015 | 6-CH$_3$ | $CF_2CF_3$ | $CH_2$—Ph |
| 2016 | 6-CH$_3$ | $CF_2CF_3$ | $CH_2$-2-Pyridyl |
| 2017 | 6-CH$_3$ | $CF_2CF_3$ | $CH_2$-3-Pyridyl |
| 2018 | 6-CH$_3$ | $CF_2CF_3$ | $CH_2$-4-Pyridyl |
| 2019 | 6-CH$_3$ | $CF_2CF_3$ | $CH_2$-2-furanyl |
| 2020 | 6-CH$_3$ | $CF_2CF_3$ | $CH_2$-3-furanyl |
| 2021 | 6-CH$_3$ | $CF_2CF_3$ | $CH_2$-2-thienyl |
| 2022 | 6-CH$_3$ | $CF_2CF_3$ | $CH_2$-3-thienyl |
| 2023 | 6-CH$_3$ | $CF_2CF_3$ | $CH_2CH_2$-cycPr |
| 2024 | 6-CH$_3$ | $CF_2CF_3$ | $CH_2CH_2$—Ph |
| 2025 | 6-CH$_3$ | $CF_2CF_3$ | $CH_2CH_2$-2-Pyridyl |
| 2026 | 6-CH$_3$ | $CF_2CF_3$ | $CH_2CH_2$-3-Pyridyl |
| 2027 | 6-CH$_3$ | $CF_2CF_3$ | $CH_2CH_2$-4-Pyridyl |
| 2028 | 6-CH$_3$ | $CF_2CF_3$ | $CH_2CH_2$-2-furanyl |
| 2029 | 6-CH$_3$ | $CF_2CF_3$ | $CH_2CH_2$-3-furanyl |
| 2030 | 6-CH$_3$ | $CF_2CF_3$ | $CH_2CH_2$-2-thienyl |
| 2031 | 6-CH$_3$ | $CF_2CF_3$ | $CH_2CH_2$-3-thienyl |
| 2032 | 6-CH$_3$ | $CF_2CF_3$ | C≡C—Et |
| 2033 | 6-CH$_3$ | $CF_2CF_3$ | C≡C-iPr |
| 2034 | 6-CH$_3$ | $CF_2CF_3$ | C≡C-cycPr |
| 2035 | 6-CH$_3$ | $CF_2CF_3$ | C≡C-1-(Me)cycPr |
| 2036 | 6-CH$_3$ | $CF_2CF_3$ | C≡C-2-pyridyl |
| 2037 | 6-CH$_3$ | $CF_2CF_3$ | C≡C-3-pyridyl |
| 2038 | 6-CH$_3$ | $CF_2CF_3$ | C≡C-4-pyridyl |
| 2039 | 6-CH$_3$ | $CF_2CF_3$ | C≡C-2-furanyl |
| 2040 | 6-CH$_3$ | $CF_2CF_3$ | C≡C-3-furanyl |
| 2041 | 6-CH$_3$ | $CF_2CF_3$ | C≡C-2-thienyl |
| 2042 | 6-CH$_3$ | $CF_2CF_3$ | C≡C-3-thienyl |
| 2043 | 6-CH$_3$ | $CF_2CF_3$ | CH=CH—Et |
| 2044 | 6-CH$_3$ | $CF_2CF_3$ | CH=CH-iPr |

TABLE 2-continued

| | | | |
|---|---|---|---|
| 2045 | 6-CH₃ | CF₂CF₃ | CH=CH-cycPr |
| 2046 | 6-CH₃ | CF₂CF₃ | CH=CH-1-(Me)cycPr |
| 2047 | 6-CH₃ | CF₂CF₃ | CH=CH-2-pyridyl |
| 2048 | 6-CH₃ | CF₂CF₃ | CH=CH-3-pyridyl |
| 2049 | 6-CH₃ | CF₂CF₃ | CH=CH-4-pyridyl |
| 2050 | 6-CH₃ | CF₂CF₃ | CH=CH-2-furanyl |
| 2051 | 6-CH₃ | CF₂CF₃ | CH=CH-3-furanyl |
| 2052 | 6-CH₃ | CF₂CF₃ | CH=CH-2-thienyl |
| 2053 | 6-CH₃ | CF₂CF₃ | CH=CH-3-thienyl |
| 2054 | 6-CH₃ | CF₂CF₃ | CH₂—C≡C-cycPr |
| 2055 | 6-CH₃ | CF₂CF₃ | CH₂—C≡C-2-furanyl |
| 2056 | 6-CH₃ | CF₂CF₃ | CH₂CH=CH-cycPr |
| 2057 | 6-CH₃ | CF₂CF₃ | CH₂CH=CH-2-furanyl |
| 2058 | 6-CH₃ | CF₂CF₃ | CH=CHCH₂-cycPr |
| 2059 | 6-CH₃ | CF₂CF₃ | CH=CHCH₂-2-furanyl |
| 2060 | 6-OCH₃ | CF₂CF₃ | CH₂CH₂CH₃ |
| 2061 | 6-OCH₃ | CF₂CF₃ | CH₂CH₂CH₂CH₃ |
| 2062 | 6-OCH₃ | CF₂CF₃ | CH₂CH₂CH₂CH₂CH₃ |
| 2063 | 6-OCH₃ | CF₂CF₃ | CH₂CH₂CH(CH₃)₂ |
| 2064 | 6-OCH₃ | CF₂CF₃ | CH₂CH₂-tBu |
| 2065 | 6-OCH₃ | CF₂CF₃ | CH₂-cycPr |
| 2066 | 6-OCH₃ | CF₂CF₃ | CH₂—Ph |
| 2067 | 6-OCH₃ | CF₂CF₃ | CH₂-2-Pyridyl |
| 2078 | 6-OCH₃ | CF₂CF₃ | CH₂-3-Pyridyl |
| 2079 | 6-OCH₃ | CF₂CF₃ | CH₂-4-Pyridyl |
| 2070 | 6-OCH₃ | CF₂CF₃ | CH₂-2-furanyl |
| 2071 | 6-OCH₃ | CF₂CF₃ | CH₂-3-furanyl |
| 2072 | 6-OCH₃ | CF₂CF₃ | CH₂-2-thienyl |
| 2073 | 6-OCH₃ | CF₂CF₃ | CH₂-3-thienyl |
| 2074 | 6-OCH₃ | CF₂CF₃ | CH₂CH₂-cycPr |
| 2075 | 6-OCH₃ | CF₂CF₃ | CH₂CH₂—Ph |
| 2076 | 6-OCH₃ | CF₂CF₃ | CH₂CH₂-2-Pyridyl |
| 2077 | 6-OCH₃ | CF₂CF₃ | CH₂CH₂-3-Pyridyl |
| 2088 | 6-OCH₃ | CF₂CF₃ | CH₂CH₂-4-Pyridyl |
| 2089 | 6-OCH₃ | CF₂CF₃ | CH₂CH₂-2-furanyl |
| 2080 | 6-OCH₃ | CF₂CF₃ | CH₂CH₂-3-furanyl |
| 2081 | 6-OCH₃ | CF₂CF₃ | CH₂CH₂-2-thienyl |
| 2082 | 6-OCH₃ | CF₂CF₃ | CH₂CH₂-3-thienyl |
| 2083 | 6-OCH₃ | CF₂CF₃ | C≡C—Et |
| 2084 | 6-OCH₃ | CF₂CF₃ | C≡C-iPr |
| 2085 | 6-OCH₃ | CF₂CF₃ | C≡C-cycPr |
| 2086 | 6-OCH₃ | CF₂CF₃ | C≡C-1-(Me)cycPr |
| 2087 | 6-OCH₃ | CF₂CF₃ | C≡C-2-pyridyl |
| 2088 | 6-OCH₃ | CF₂CF₃ | C≡C-3-pyridyl |
| 2089 | 6-OCH₃ | CF₂CF₃ | C≡C-4-pyridyl |
| 2090 | 6-OCH₃ | CF₂CF₃ | C≡C-2-furanyl |
| 2091 | 6-OCH₃ | CF₂CF₃ | C≡C-3-furanyl |
| 2092 | 6-OCH₃ | CF₂CF₃ | C≡C-2-thienyl |
| 2093 | 6-OCH₃ | CF₂CF₃ | C≡C-3-thienyl |
| 2094 | 6-OCH₃ | CF₂CF₃ | CH=CH—Et |
| 2095 | 6-OCH₃ | CF₂CF₃ | CH=CH-iPr |
| 2096 | 6-OCH₃ | CF₂CF₃ | CH=CH-cycPr |
| 2097 | 6-OCH₃ | CF₂CF₃ | CH=CH-1-(Me)cycPr |
| 2098 | 6-OCH₃ | CF₂CF₃ | CH=CH-2-pyridyl |
| 2099 | 6-OCH₃ | CF₂CF₃ | CH=CH-3-pyridyl |
| 2100 | 6-OCH₃ | CF₂CF₃ | CH=CH-4-pyridyl |
| 2101 | 6-OCH₃ | CF₂CF₃ | CH=CH-2-furanyl |
| 2102 | 6-OCH₃ | CF₂CF₃ | CH=CH-3-furanyl |
| 2103 | 6-OCH₃ | CF₂CF₃ | CH=CH-2-thienyl |
| 2104 | 6-OCH₃ | CF₂CF₃ | CH=CH-3-thienyl |
| 2105 | 6-OCH₃ | CF₂CF₃ | CH₂—C≡C-cycPr |
| 2106 | 6-OCH₃ | CF₂CF₃ | CH₂—C≡C-2-furanyl |
| 2107 | 6-OCH₃ | CF₂CF₃ | CH₂CH=CH-cycPr |
| 2108 | 6-OCH₃ | CF₂CF₃ | CH₂CH=CH-2-furanyl |
| 2109 | 6-OCH₃ | CF₂CF₃ | CH=CHCH₂-cycPr |
| 2110 | 6-OCH₃ | CF₂CF₃ | CH=CHCH₂-2-furanyl |
| 2111 | 5,6-OCH₂O— | CF₂CF₃ | CH₂CH₂CH₃ |
| 2112 | 5,6-OCH₂O— | CF₂CF₃ | CH₂CH₂CH₂CH₃ |
| 2113 | 5,6-OCH₂O— | CF₂CF₃ | CH₂CH₂CH₂CH₂CH₃ |
| 2114 | 5,6-OCH₂O— | CF₂CF₃ | CH₂CH₂CH(CH₃)₂ |
| 2115 | 5,6-OCH₂O— | CF₂CF₃ | CH₂CH₂-tBu |
| 2116 | 5,6-OCH₂O— | CF₂CF₃ | CH₂-cycPr |
| 2117 | 5,6-OCH₂O— | CF₂CF₃ | CH₂—Ph |
| 2118 | 5,6-OCH₂O— | CF₂CF₃ | CH₂-2-Pyridyl |
| 2119 | 5,6-OCH₂O— | CF₂CF₃ | CH₂-3-Pyridyl |
| 2120 | 5,6-OCH₂O— | CF₂CF₃ | CH₂-4-Pyridyl |
| 2121 | 5,6-OCH₂O— | CF₂CF₃ | CH₂-2-furanyl |
| 2122 | 5,6-OCH₂O— | CF₂CF₃ | CH₂-3-furanyl |
| 2123 | 5,6-OCH₂O— | CF₂CF₃ | CH₂-2-thienyl |
| 2124 | 5,6-OCH₂O— | CF₂CF₃ | CH₂-3-thienyl |
| 2125 | 5,6-OCH₂O— | CF₂CF₃ | CH₂CH₂-cycPr |
| 2126 | 5,6-OCH₂O— | CF₂CF₃ | CH₂CH₂—Ph |
| 2127 | 5,6-OCH₂O— | CF₂CF₃ | CH₂CH₂-2-Pyridyl |
| 2128 | 5,6-OCH₂O— | CF₂CF₃ | CH₂CH₂-3-Pyridyl |
| 2129 | 5,6-OCH₂O— | CF₂CF₃ | CH₂CH₂-4-Pyridyl |
| 2130 | 5,6-OCH₂O— | CF₂CF₃ | CH₂CH₂-2-furanyl |
| 2131 | 5,6-OCH₂O— | CF₂CF₃ | CH₂CH₂-3-furanyl |
| 2132 | 5,6-OCH₂O— | CF₂CF₃ | CH₂CH₂-2-thienyl |
| 2133 | 5,6-OCH₂O— | CF₂CF₃ | CH₂CH₂-3-thienyl |
| 2134 | 5,6-OCH₂O— | CF₂CF₃ | C≡C—Et |
| 2135 | 5,6-OCH₂O— | CF₂CF₃ | C≡C-iPr |
| 2136 | 5,6-OCH₂O— | CF₂CF₃ | C≡C-cycPr |
| 2137 | 5,6-OCH₂O— | CF₂CF₃ | C≡C-1-(Me)cycPr |
| 2138 | 5,6-OCH₂O— | CF₂CF₃ | C≡C-2-pyridyl |
| 2139 | 5,6-OCH₂O— | CF₂CF₃ | C≡C-3-pyridyl |
| 2140 | 5,6-OCH₂O— | CF₂CF₃ | C≡C-4-pyridyl |
| 2141 | 5,6-OCH₂O— | CF₂CF₃ | C≡C-2-furanyl |
| 2142 | 5,6-OCH₂O— | CF₂CF₃ | C≡C-3-furanyl |
| 2143 | 5,6-OCH₂O— | CF₂CF₃ | C≡C-2-thienyl |
| 2144 | 5,6-OCH₂O— | CF₂CF₃ | C≡C-3-thienyl |
| 2145 | 5,6-OCH₂O— | CF₂CF₃ | CH=CH—Et |
| 2146 | 5,6-OCH₂O— | CF₂CF₃ | CH=CH-iPr |
| 2147 | 5,6-OCH₂O— | CF₂CF₃ | CH=CH-cycPr |
| 2148 | 5,6-OCH₂O— | CF₂CF₃ | CH=CH-1-(Me)cycPr |
| 2149 | 5,6-OCH₂O— | CF₂CF₃ | CH=CH-2-pyridyl |
| 2150 | 5,6-OCH₂O— | CF₂CF₃ | CH=CH-3-pyridyl |
| 2151 | 5,6-OCH₂O— | CF₂CF₃ | CH=CH-4-pyridyl |
| 2152 | 5,6-OCH₂O— | CF₂CF₃ | CH=CH-2-furanyl |
| 2153 | 5,6-OCH₂O— | CF₂CF₃ | CH=CH-3-furanyl |
| 2154 | 5,6-OCH₂O— | CF₂CF₃ | CH=CH-2-thienyl |
| 2155 | 5,6-OCH₂O— | CF₂CF₃ | CH=CH-3-thienyl |
| 2156 | 5,6-OCH₂O— | CF₂CF₃ | CH₂—C≡C-cycPr |
| 2157 | 5,6-OCH₂O— | CF₂CF₃ | CH₂—C≡C-2-furanyl |
| 2158 | 5,6-OCH₂O— | CF₂CF₃ | CH₂CH=CH-cycPr |
| 2159 | 5,6-OCH₂O— | CF₂CF₃ | CH₂CH=CH-2-furanyl |
| 2160 | 5,6-OCH₂O— | CF₂CF₃ | CH=CHCH₂-cycPr |
| 2161 | 5,6-OCH₂O— | CF₂CF₃ | CH=CHCH₂-2-furanyl |
| 2201 | 5-Cl | cycPr | CH₂CH₂CH₃ |
| 2202 | 5-Cl | cycPr | CH₂CH₂CH₂CH₃ |
| 2203 | 5-Cl | cycPr | CH₂CH₂CH₂CH₂CH₃ |
| 2204 | 5-Cl | cycPr | CH₂CH₂CH(CH₃)₂ |
| 2205 | 5-Cl | cycPr | CH₂CH₂-tBu |
| 2206 | 5-Cl | cycPr | CH₂-cycPr |
| 2207 | 5-Cl | cycPr | CH₂—Ph |
| 2208 | 5-Cl | cycPr | CH₂-2-Pyridyl |
| 2209 | 5-Cl | cycPr | CH₂-3-Pyridyl |
| 2210 | 5-Cl | cycPr | CH₂-4-Pyridyl |
| 2211 | 5-Cl | cycPr | CH₂-2-furanyl |
| 2212 | 5-Cl | cycPr | CH₂-3-furanyl |
| 2213 | 5-Cl | cycPr | CH₂-2-thienyl |
| 2214 | 5-Cl | cycPr | CH₂-3-thienyl |
| 2215 | 5-Cl | cycPr | CH₂CH₂-cycPr |
| 2216 | 5-Cl | cycPr | CH₂CH₂—Ph |
| 2217 | 5-Cl | cycPr | CH₂CH₂-2-Pyridyl |
| 2218 | 5-Cl | cycPr | CH₂CH₂-3-Pyridyl |
| 2219 | 5-Cl | cycPr | CH₂CH₂-4-Pyridyl |
| 2220 | 5-Cl | cycPr | CH₂CH₂-2-furanyl |
| 2221 | 5-Cl | cycPr | CH₂CH₂-3-furanyl |
| 2222 | 5-Cl | cycPr | CH₂CH₂-2-thienyl |
| 2223 | 5-Cl | cycPr | CH₂CH₂-3-thienyl |
| 2224 | 5-Cl | cycPr | C≡C—Et |
| 2225 | 5-Cl | cycPr | C≡C-iPr |
| 2226 | 5-Cl | cycPr | C≡C-cycPr |
| 2227 | 5-Cl | cycPr | C≡C-1-(Me)cycPr |
| 2228 | 5-Cl | cycPr | C≡C-2-pyridyl |
| 2229 | 5-Cl | cycPr | C≡C-3-pyridyl |
| 2230 | 5-Cl | cycPr | C≡C-4-pyridyl |
| 2231 | 5-Cl | cycPr | C≡C-2-furanyl |
| 2232 | 5-Cl | cycPr | C≡C-3-furanyl |
| 2233 | 5-Cl | cycPr | C≡C-2-thienyl |
| 2234 | 5-Cl | cycPr | C≡C-3-thienyl |
| 2235 | 5-Cl | cycPr | CH=CH—Et |
| 2236 | 5-Cl | cycPr | CH=CH-iPr |
| 2237 | 5-Cl | cycPr | CH=CH-cycPr |
| 2238 | 5-Cl | cycPr | CH=CH-1-(Me)cycPr |
| 2239 | 5-Cl | cycPr | CH=CH-2-pyridyl |
| 2240 | 5-Cl | cycPr | CH=CH-3-pyridyl |
| 2241 | 5-Cl | cycPr | CH=CH-4-pyridyl |

TABLE 2-continued

| | | | |
|---|---|---|---|
| 2242 | 5-Cl | cycPr | CH=CH-2-furanyl |
| 2243 | 5-Cl | cycPr | CH=CH-3-furanyl |
| 2244 | 5-Cl | cycPr | CH=CH-2-thienyl |
| 2245 | 5-Cl | cycPr | CH=CH-3-thienyl |
| 2246 | 5-Cl | cycPr | $CH_2$—C≡C-cycPr |
| 2247 | 5-Cl | cycPr | $CH_2$—C≡C-2-furanyl |
| 2248 | 5-Cl | cycPr | $CH_2$CH=CH-cycPr |
| 2249 | 5-Cl | cycPr | $CH_2$CH=CH-2-furanyl |
| 2250 | 5-Cl | cycPr | CH=CH$CH_2$-cycPr |
| 2251 | 5-Cl | cycPr | CH=CH$CH_2$-2-furanyl |
| 2252 | 6-Cl | cycPr | $CH_2CH_2CH_3$ |
| 2253 | 6-Cl | cycPr | $CH_2CH_2CH_2CH_3$ |
| 2254 | 6-Cl | cycPr | $CH_2CH_2CH_2CH_2CH_3$ |
| 2255 | 6-Cl | cycPr | $CH_2CH_2CH(CH_3)_2$ |
| 2256 | 6-Cl | cycPr | $CH_2CH_2$-tBu |
| 2257 | 6-Cl | cycPr | $CH_2$-cycPr |
| 2258 | 6-Cl | cycPr | $CH_2$—Ph |
| 2259 | 6-Cl | cycPr | $CH_2$-2-Pyridyl |
| 2260 | 6-Cl | cycPr | $CH_2$-3-Pyridyl |
| 2261 | 6-Cl | cycPr | $CH_2$-4-Pyridyl |
| 2262 | 6-Cl | cycPr | $CH_2$-2-furanyl |
| 2263 | 6-Cl | cycPr | $CH_2$-3-furanyl |
| 2264 | 6-Cl | cycPr | $CH_2$-2-thienyl |
| 2265 | 6-Cl | cycPr | $CH_2$-3-thienyl |
| 2266 | 6-Cl | cycPr | $CH_2CH_2$-cycPr |
| 2267 | 6-Cl | cycPr | $CH_2CH_2$—Ph |
| 2268 | 6-Cl | cycPr | $CH_2CH_2$-2-Pyridyl |
| 2269 | 6-Cl | cycPr | $CH_2CH_2$-3-Pyridyl |
| 2270 | 6-Cl | cycPr | $CH_2CH_2$-4-Pyridyl |
| 2271 | 6-Cl | cycPr | $CH_2CH_2$-2-furanyl |
| 2272 | 6-Cl | cycPr | $CH_2CH_2$-3-furanyl |
| 2273 | 6-Cl | cycPr | $CH_2CH_2$-2-thienyl |
| 2274 | 6-Cl | cycPr | $CH_2CH_2$-3-thienyl |
| 2275 | 6-Cl | cycPr | C≡C—Et |
| 2276 | 6-Cl | cycPr | C≡C-iPr |
| 2277 | 6-Cl | cycPr | C≡C-cycPr |
| 2278 | 6-Cl | cycPr | C≡C-1-(Me)cycPr |
| 2279 | 6-Cl | cycPr | C≡C-2-pyridyl |
| 2280 | 6-Cl | cycPr | C≡C-3-pyridyl |
| 2281 | 6-Cl | cycPr | C≡C-4-pyridyl |
| 2282 | 6-Cl | cycPr | C≡C-2-furanyl |
| 2283 | 6-Cl | cycPr | C≡C-3-furanyl |
| 2284 | 6-Cl | cycPr | C≡C-2-thienyl |
| 2285 | 6-Cl | cycPr | C≡C-3-thienyl |
| 2286 | 6-Cl | cycPr | CH=CH—Et |
| 2287 | 6-Cl | cycPr | CH=CH-iPr |
| 2288 | 6-Cl | cycPr | CH=CH-cycPr |
| 2289 | 6-Cl | cycPr | CH=CH-1-(Me)cycPr |
| 2290 | 6-Cl | cycPr | CH=CH-2-pyridyl |
| 2291 | 6-Cl | cycPr | CH=CH-3-pyridyl |
| 2292 | 6-Cl | cycPr | CH=CH-4-pyridyl |
| 2293 | 6-Cl | cycPr | CH=CH-2-furanyl |
| 2294 | 6-Cl | cycPr | CH=CH-3-furanyl |
| 2295 | 6-Cl | cycPr | CH=CH-2-thienyl |
| 2296 | 6-Cl | cycPr | CH=CH-3-thienyl |
| 2297 | 6-Cl | cycPr | $CH_2$—C≡C-cycPr |
| 2298 | 6-cl | cycPr | $CH_2$—C≡C-2-furanyl |
| 2299 | 6-Cl | cycPr | $CH_2$CH=CH-cycPr |
| 2300 | 6-Cl | cycPr | $CH_2$CH=CH-2-furanyl |
| 2301 | 6-Cl | cycPr | CH=CH$CH_2$-cycPr |
| 2302 | 6-Cl | cycPr | CH=CH$CH_2$-2-furanyl |
| 2303 | 5-F | cycPr | $CH_2CH_2CH_3$ |
| 2304 | 5-F | cycPr | $CH_2CH_2CH_2CH_3$ |
| 2305 | 5-F | cycPr | $CH_2CH_2CH_2CH_2CH_3$ |
| 2306 | 5-F | cycPr | $CH_2CH_2CH(CH_3)_2$ |
| 2307 | 5-F | cycPr | $CH_2CH_2$-tBu |
| 2308 | 5-F | cycPr | $CH_2$-cycPr |
| 2309 | 5-F | cycPr | $CH_2$—Ph |
| 2310 | 5-F | cycPr | $CH_2$-2-Pyridyl |
| 2311 | 5-F | cycPr | $CH_2$-3-Pyridyl |
| 2312 | 5-F | cycPr | $CH_2$-4-Pyridyl |
| 2313 | 5-F | cycPr | $CH_2$-2-furanyl |
| 2314 | 5-F | cycPr | $CH_2$-3-furanyl |
| 2315 | 5-F | cycPr | $CH_2$-2-thienyl |
| 2316 | 5-F | cycPr | $CH_2$-3-thienyl |
| 2317 | 5-F | cycPr | $CH_2CH_2$-cycPr |
| 2318 | 5-F | cycPr | $CH_2CH_2$—Ph |
| 2319 | 5-F | cycPr | $CH_2CH_2$-2-Pyridyl |
| 2320 | 5-F | cycPr | $CH_2CH_2$-3-Pyridyl |
| 2321 | 5-F | cycPr | $CH_2CH_2$-4-Pyridyl |
| 2322 | 5-F | cycPr | $CH_2CH_2$-2-furanyl |
| 2323 | 5-F | cycPr | $CH_2CH_2$-3-furanyl |
| 2324 | 5-F | cycPr | $CH_2CH_2$-2-thienyl |
| 2325 | 5-F | cycPr | $CH_2CH_2$-3-thienyl |
| 2326 | 5-F | cycPr | C≡C—Et |
| 2327 | 5-F | cycPr | C≡C-iPr |
| 2328 | 5-F | cycPr | C≡C-cycPr |
| 2329 | 5-F | cycPr | C≡C-1-(Me)cycPr |
| 2330 | 5-F | cycPr | C≡C-2-pyridyl |
| 2331 | 5-F | cycPr | C≡C-3-pyridyl |
| 2332 | 5-F | cycPr | C≡C-4-pyridyl |
| 2333 | 5-F | cycPr | C≡C-2-furanyl |
| 2334 | 5-F | cycPr | C≡C-3-furanyl |
| 2335 | 5-F | cycPr | C≡C-2-thienyl |
| 2336 | 5-F | cycPr | C≡C-3-thienyl |
| 2337 | 5-F | cycPr | CH=CH—Et |
| 2338 | 5-F | cycPr | CH=CH-iPr |
| 2339 | 5-F | cycPr | CH=CH-cycPr |
| 2340 | 5-F | cycPr | CH=CH-1-(Me)cycPr |
| 2341 | 5-F | cycPr | CH=CH-2-pyridyl |
| 2342 | 5-F | cycPr | CH=CH-3-pyridyl |
| 2343 | 5-F | cycPr | CH=CH-4-pyridyl |
| 2344 | 5-F | cycPr | CH=CH-2-furanyl |
| 2345 | 5-F | cycPr | CH=CH-3-furanyl |
| 2346 | 5-F | cycPr | CH=CH-2-thienyl |
| 2347 | 5-F | cycPr | CH=CH-3-thienyl |
| 2348 | 5-F | cycPr | $CH_2$—C≡C-cycPr |
| 2349 | 5-F | cycPr | $CH_2$—C≡C-2-furanyl |
| 2350 | 5-F | cycPr | $CH_2$CH=CH-cycPr |
| 2351 | 5-F | cycPr | $CH_2$CH=CH-2-furanyl |
| 2352 | 5-F | cycPr | CH=CH$CH_2$-cycPr |
| 2353 | 5-F | cycPr | CH=CH$CH_2$-2-furanyl |
| 2354 | 6-F | cycPr | $CH_2CH_2CH_3$ |
| 2355 | 6-F | cycPr | $CH_2CH_2CH_2CH_3$ |
| 2356 | 6-F | cycPr | $CH_2CH_2CH_2CH_2CH_3$ |
| 2357 | 6-F | cycPr | $CH_2CH_2CH(CH_3)_2$ |
| 2358 | 6-F | cycPr | $CH_2CH_2$-tBu |
| 2359 | 6-F | cycPr | $CH_2$-cycPr |
| 2360 | 6-F | cycPr | $CH_2$—Ph |
| 2361 | 6-F | cycPr | $CH_2$-2-Pyridyl |
| 2362 | 6-F | cycPr | $CH_2$-3-Pyridyl |
| 2363 | 6-F | cycPr | $CH_2$-4-Pyridyl |
| 2364 | 6-F | cycPr | $CH_2$-2-furanyl |
| 2365 | 6-F | cycPr | $CH_2$-3-furanyl |
| 2366 | 6-F | cycPr | $CH_2$-2-thienyl |
| 2367 | 6-F | cycPr | $CH_2$-3-thienyl |
| 2368 | 6-F | cycPr | $CH_2CH_2$-cycPr |
| 2369 | 6-F | cycPr | $CH_2CH_2$—Ph |
| 2370 | 6-F | cycPr | $CH_2CH_2$-2-Pyridyl |
| 2371 | 6-F | cycPr | $CH_2CH_2$-3-Pyridyl |
| 2372 | 6-F | cycPr | $CH_2CH_2$-4-Pyridyl |
| 2373 | 6-F | cycPr | $CH_2CH_2$-2-furanyl |
| 2374 | 6-F | cycPr | $CH_2CH_2$-3-furanyl |
| 2375 | 6-F | cycPr | $CH_2CH_2$-2-thienyl |
| 2376 | 6-F | cycPr | $CH_2CH_2$-3-thienyl |
| 2377 | 6-F | cycPr | C≡C—Et |
| 2378 | 6-F | cycPr | C≡C-iPr |
| 2379 | 6-F | cycPr | C≡C-cycPr |
| 2380 | 6-F | cycPr | C≡C-1-(Me)cycPr |
| 2381 | 6-F | cycPr | C≡C-2-pyridyl |
| 2382 | 6-F | cycPr | C≡C-3-pyridyl |
| 2383 | 6-F | cycPr | C≡C-4-pyridyl |
| 2384 | 6-F | cycPr | C≡C-2-furanyl |
| 2385 | 6-F | cycPr | C≡C-3-furanyl |
| 2386 | 6-F | cycPr | C≡C-2-thienyl |
| 2387 | 6-F | cycPr | C≡C-3-thienyl |
| 2388 | 6-F | cycPr | CH=CH—Et |
| 2389 | 6-F | cycPr | CH=CH-iPr |
| 2390 | 6-F | cycPr | CH=CH-cycPr |
| 2391 | 6-F | cycPr | CH=CH-1-(Me)cycPr |
| 2392 | 6-F | cycPr | CH=CH-2-pyridyl |
| 2393 | 6-F | cycPr | CH=CH-3-pyridyl |
| 2394 | 6-F | cycPr | CH=CH-4-pyridyl |
| 2395 | 6-F | cycPr | CH=CH-2-furanyl |
| 2396 | 6-F | cycPr | CH=CH-3-furanyl |
| 2397 | 6-F | cycPr | CH=CH-2-thienyl |
| 2398 | 6-F | cycPr | CH=CH-3-thienyl |
| 2399 | 6-F | cycPr | $CH_2$—C≡C-cycPr |

TABLE 2-continued

| | | | |
|---|---|---|---|
| 2400 | 6-F | cycPr | CH$_2$—C≡C-2-furanyl |
| 2401 | 6-F | cycPr | CH$_2$CH=CH-cycPr |
| 2402 | 6-F | cycPr | CH$_2$CH=CH-2-furanyl |
| 2403 | 6-F | cycPr | CH=CHCH$_2$-cycPr |
| 2404 | 6-F | cycPr | CH=CHCH$_2$-2-furanyl |
| 2405 | 5,6-diCl | cycPr | CH$_2$CH$_2$CH$_3$ |
| 2406 | 5,6-diCl | cycPr | CH$_2$CH$_2$CH$_2$CH$_3$ |
| 2407 | 5,6-diCl | cycPr | CH$_2$CH$_2$CH$_2$CH$_2$CH$_3$ |
| 2408 | 5,6-diCl | cycPr | CH$_2$CH$_2$CH(CH$_3$)$_2$ |
| 2409 | 5,6-diCl | cycPr | CH$_2$CH$_2$-tBu |
| 2410 | 5,6-diCl | cycPr | CH$_2$-cycPr |
| 2411 | 5,6-diCl | cycPr | CH$_2$—Ph |
| 2412 | 5,6-diCl | cycPr | CH$_2$-2-Pyridyl |
| 2413 | 5,6-diCl | cycPr | CH$_2$-3-Pyridyl |
| 2414 | 5,6-diCl | cycPr | CH$_2$-4-Pyridyl |
| 2415 | 5,6-diCl | cycPr | CH$_2$-2-furanyl |
| 2416 | 5,6-diCl | cycPr | CH$_2$-3-furanyl |
| 2417 | 5,6-diCl | cycPr | CH$_2$-2-thienyl |
| 2418 | 5,6-diCl | cycPr | CH$_2$-3-thienyl |
| 2419 | 5,6-diCl | cycPr | CH$_2$CH$_2$-cycPr |
| 2420 | 5,6-diCl | cycPr | CH$_2$CH$_2$—Ph |
| 2421 | 5,6-diCl | cycPr | CH$_2$CH$_2$-2-Pyridyl |
| 2422 | 5,6-diCl | cycPr | CH$_2$CH$_2$-3-Pyridyl |
| 2423 | 5,6-diCl | cycPr | CH$_2$CH$_2$-4-Pyridyl |
| 2424 | 5,6-diCl | cycPr | CH$_2$CH$_2$-2-furanyl |
| 2425 | 5,6-diCl | cycPr | CH$_2$CH$_2$-3-furanyl |
| 2426 | 5,6-diCl | cycPr | CH$_2$CH$_2$-2-thienyl |
| 2427 | 5,6-diCl | cycPr | CH$_2$CH$_2$-3-thienyl |
| 2428 | 5,6-diCl | cycPr | C≡C—Et |
| 2429 | 5,6-diCl | cycPr | C≡C-iPr |
| 2430 | 5,6-diCl | cycPr | C≡C-cycPr |
| 2431 | 5,6-diCl | cycPr | C≡C-1-(Me)cycPr |
| 2432 | 5,6-diCl | cycPr | C≡C-2-pyridyl |
| 2433 | 5,6-diCl | cycPr | C≡C-3-pyridyl |
| 2434 | 5,6-diCl | cycPr | C≡C-4-pyridyl |
| 2435 | 5,6-diCl | cycPr | C≡C-2-furanyl |
| 2436 | 5,6-diCl | cycPr | C≡C-3-furanyl |
| 2437 | 5,6-diCl | cycPr | C≡C-2-thienyl |
| 2438 | 5,6-diCl | cycPr | C≡C-3-thienyl |
| 2439 | 5,6-diCl | cycPr | CH=CH—Et |
| 2440 | 5,6-diCl | cycPr | CH=CH-iPr |
| 2441 | 5,6-diCl | cycPr | CH=CH-cycPr |
| 2442 | 5,6-diCl | cycPr | CH=CH-1-(Me)cycPr |
| 2443 | 5,6-diCl | cycPr | CH=CH-2-pyridyl |
| 2444 | 5,6-diCl | cycPr | CH=CH-3-pyridyl |
| 2445 | 5,6-diCl | cycPr | CH=CH-4-pyridyl |
| 2446 | 5,6-diCl | cycPr | CH=CH-2-furanyl |
| 2447 | 5,6-diCl | cycPr | CH=CH-3-furanyl |
| 2448 | 5,6-diCl | cycPr | CH=CH-2-thienyl |
| 2449 | 5,6-diCl | cycPr | CH=CH-3-thienyl |
| 2450 | 5,6-diCl | cycPr | CH$_2$—C≡C-cycPr |
| 2451 | 5,6-diCl | cycPr | CH$_2$—C≡C-2-furanyl |
| 2452 | 5,6-diCl | cycPr | CH$_2$CH=CH-cycPr |
| 2453 | 5,6-diCl | cycPr | CH$_2$CH=CH-2-furanyl |
| 2454 | 5,6-diCl | cycPr | CH=CHCH$_2$-cycPr |
| 2455 | 5,6-diCl | cycPr | CH=CHCH$_2$-2-furanyl |
| 2456 | 5,6-diF | cycPr | CH$_2$CH$_2$CH$_3$ |
| 2457 | 5,6-diF | cycPr | CH$_2$CH$_2$CH$_2$CH$_3$ |
| 2458 | 5,6-diF | cycPr | CH$_2$CH$_2$CH$_2$CH$_2$CH$_3$ |
| 2459 | 5,6-diF | cycPr | CH$_2$CH$_2$CH(CH$_3$)$_2$ |
| 2460 | 5,6-diF | cycPr | CH$_2$CH$_2$-tBu |
| 2461 | 5,6-diF | cycPr | CH$_2$-cycPr |
| 2462 | 5,6-diF | cycPr | CH$_2$—Ph |
| 2463 | 5,6-diF | cycPr | CH$_2$-2-Pyridyl |
| 2464 | 5,6-diF | cycPr | CH$_2$-3-Pyridyl |
| 2465 | 5,6-diF | cycPr | CH$_2$-4-Pyridyl |
| 2466 | 5,6-diF | cycPr | CH$_2$-2-furanyl |
| 2467 | 5,6-diF | cycPr | CH$_2$-3-furanyl |
| 2468 | 5,6-diF | cycPr | CH$_2$-2-thienyl |
| 2469 | 5,6-diF | cycPr | CH$_2$-3-thienyl |
| 2470 | 5,6-diF | cycPr | CH$_2$CH$_2$-cycPr |
| 2471 | 5,6-diF | cycPr | CH$_2$CH$_2$—Ph |
| 2472 | 5,6-diF | cycPr | CH$_2$CH$_2$-2-Pyridyl |
| 2473 | 5,6-diF | cycPr | CH$_2$CH$_2$-3-Pyridyl |
| 2474 | 5,6-diF | cycPr | CH$_2$CH$_2$-4-Pyridyl |
| 2475 | 5,6-diF | cycPr | CH$_2$CH$_2$-2-furanyl |
| 2476 | 5,6-diF | cycPr | CH$_2$CH$_2$-3-furanyl |
| 2477 | 5,6-diF | cycPr | CH$_2$CH$_2$-2-thienyl |
| 2478 | 5,6-diF | cycPr | CH$_2$CH$_2$-3-thienyl |
| 2479 | 5,6-diF | cycPr | C≡C—Et |
| 2480 | 5,6-diF | cycPr | C≡C-iPr |
| 2481 | 5,6-diF | cycPr | C≡C-cycPr |
| 2482 | 5,6-diF | cycPr | C≡C-1-(Me)cycPr |
| 2483 | 5,6-diF | cycPr | C≡C-2-pyridyl |
| 2484 | 5,6-diF | cycPr | C≡C-3-pyridyl |
| 2485 | 5,6-diF | cycPr | C≡C-4-pyridyl |
| 2486 | 5,6-diF | cycPr | C≡C-2-furanyl |
| 2487 | 5,6-diF | cycPr | C≡C-3-furanyl |
| 2488 | 5,6-diF | cycPr | C≡C-2-thienyl |
| 2489 | 5,6-diF | cycPr | C≡C-3-thienyl |
| 2490 | 5,6-diF | cycPr | CH=CH—Et |
| 2491 | 5,6-diF | cycPr | CH=CH-iPr |
| 2492 | 5,6-diF | cycPr | CH=CH-cycPr |
| 2493 | 5,6-diF | cycPr | CH=CH-1-(Me)cycPr |
| 2494 | 5,6-diF | cycPr | CH=CH-2-pyridyl |
| 2495 | 5,6-diF | cycPr | CH=CH-3-pyridyl |
| 2496 | 5,6-diF | cycPr | CH=CH-4-pyridyl |
| 2497 | 5,6-diF | cycPr | CH=CH-2-furanyl |
| 2498 | 5,6-diF | cycPr | CH=CH-3-furanyl |
| 2499 | 5,6-diF | cycPr | CH=CH-2-thienyl |
| 2500 | 5,6-diF | cycPr | CH=CH-3-thienyl |
| 2501 | 5,6-diF | cycPr | CH$_2$—C≡C-cycPr |
| 2502 | 5,6-diF | cycPr | CH$_2$—C≡C-2-furanyl |
| 2503 | 5,6-diF | cycPr | CH$_2$CH=CH-cycPr |
| 2504 | 5,6-diF | cycPr | CH$_2$CH=CH-2-furanyl |
| 2505 | 5,6-diF | cycPr | CH=CHCH$_2$-cycPr |
| 2506 | 5,6-diF | cycPr | CH=CHCH$_2$-2-furanyl |
| 2507 | 5-Cl, 6-F | cycPr | CH$_2$CH$_2$CH$_3$ |
| 2508 | 5-Cl, 6-F | cycPr | CH$_2$CH$_2$CH$_2$CH$_3$ |
| 2509 | 5-Cl, 6-F | cycPr | CH$_2$CH$_2$CH$_2$CH$_2$CH$_3$ |
| 2510 | 5-Cl, 6-F | cycPr | CH$_2$CH$_2$CH(CH$_3$)$_2$ |
| 2511 | 5-Cl, 6-F | cycPr | CH$_2$CH$_2$-tBu |
| 2512 | 5-Cl, 6-F | cycPr | CH$_2$-cycPr |
| 2513 | 5-Cl, 6-F | cycPr | CH$_2$—Ph |
| 2514 | 5-Cl, 6-F | cycPr | CH$_2$-2-Pyridyl |
| 2515 | 5-Cl, 6-F | cycPr | CH$_2$-3-Pyridyl |
| 2516 | 5-Cl, 6-F | cycPr | CH$_2$-4-Pyridyl |
| 2517 | 5-Cl, 6-F | cycPr | CH$_2$-2-furanyl |
| 2518 | 5-Cl, 6-F | cycPr | CH$_2$-3-furanyl |
| 2519 | 5-Cl, 6-F | cycPr | CH$_2$-2-thienyl |
| 2520 | 5-Cl, 6-F | cycPr | CH$_2$-3-thienyl |
| 2521 | 5-Cl, 6-F | cycPr | CH$_2$CH$_2$-cycPr |
| 2522 | 5-Cl, 6-F | cycPr | CH$_2$CH$_2$—Ph |
| 2523 | 5-Cl, 6-F | cycPr | CH$_2$CH$_2$-2-Pyridyl |
| 2524 | 5-Cl, 6-F | cycPr | CH$_2$CH$_2$-3-Pyridyl |
| 2525 | 5-Cl, 6-F | cycPr | CH$_2$CH-4-Pyridyl |
| 2526 | 5-Cl, 6-F | cycPr | CH$_2$CH-2-furanyl |
| 2527 | 5-Cl, 6-F | cycPr | CH$_2$CH-3-furanyl |
| 2528 | 5-Cl, 6-F | cycPr | CH$_2$CH-2-thienyl |
| 2529 | 5-Cl, 6-F | cycPr | CH$_2$CH-3-thienyl |
| 2530 | 5-Cl, 6-F | cycPr | C≡C—Et |
| 2531 | 5-Cl, 6-F | cycPr | C≡C-iPr |
| 2532 | 5-Cl, 6-F | cycPr | C≡C-cycPr |
| 2533 | 5-Cl, 6-F | cycPr | C≡C-1-(Me)cycPr |
| 2534 | 5-Cl, 6-F | cycPr | C≡C-2-pyridyl |
| 2535 | 5-Cl, 6-F | cycPr | C≡C-3-pyridyl |
| 2536 | 5-Cl, 6-F | cycPr | C≡C-4-pyridyl |
| 2537 | 5-Cl, 6-F | cycPr | C≡C-2-furanyl |
| 2538 | 5-Cl, 6-F | cycPr | C≡C-3-furanyl |
| 2539 | 5-Cl, 6-F | cycPr | C≡C-2-thienyl |
| 2540 | 5-Cl, 6-F | cycPr | C≡C-3-thienyl |
| 2541 | 5-Cl, 6-F | cycPr | CH=CH—Et |
| 2542 | 5-Cl, 6-F | cycPr | CH=CH-iPr |
| 2543 | 5-Cl, 6-F | cycPr | CH=CH-cycPr |
| 2544 | 5-Cl, 6-F | cycPr | CH=CH-1-(Me)cycPr |
| 2545 | 5-Cl, 6-F | cycPr | CH=CH-2-pyridyl |
| 2546 | 5-Cl, 6-F | cycPr | CH=CH-3-pyridyl |
| 2547 | 5-Cl, 6-F | cycPr | CH=CH-4-pyridyl |
| 2548 | 5-Cl, 6-F | cycPr | CH=CH-2-furanyl |
| 2549 | 5-Cl, 6-F | cycPr | CH=CH-3-furanyl |
| 2550 | 5-Cl, 6-F | cycPr | CH=CH-2-thienyl |
| 2551 | 5-Cl, 6-F | cycPr | CH=CH-3-thienyl |
| 2552 | 5-Cl, 6-F | cycPr | CH$_2$—C≡C-cycPr |
| 2553 | 5-Cl, 6-F | cycPr | CH$_2$—C≡C-2-furanyl |
| 2554 | 5-Cl, 6-F | cycPr | CH$_2$CH=CH-cycPr |
| 2555 | 5-Cl, 6-F | cycPr | CH$_2$CH=CH-2-furanyl |
| 2556 | 5-Cl, 6-F | cycPr | CH=CHCH$_2$-cycPr |
| 2557 | 5-Cl, 6-F | cycPr | CH=CHCH$_2$-2-furanyl |

TABLE 2-continued

| | | | |
|---|---|---|---|
| 2558 | 5-F, 6-Cl | cycPr | CH$_2$CH$_2$CH$_3$ |
| 2559 | 5-F, 6-Cl | cycPr | CH$_2$CH$_2$CH$_2$CH$_3$ |
| 2560 | 5-F, 6-Cl | cycPr | CH$_2$CH$_2$CH$_2$CH$_2$CH$_3$ |
| 2561 | 5-F, 6-Cl | cycPr | CH$_2$CH$_2$CH(CH$_3$)$_2$ |
| 2562 | 5-F, 6-Cl | cycPr | CH$_2$CH$_2$-tBu |
| 2563 | 5-F, 6-Cl | cycPr | CH$_2$-cycPr |
| 2564 | 5-F, 6-Cl | cycPr | CH$_2$—Ph |
| 2565 | 5-F, 6-Cl | cycPr | CH$_2$-2-Pyridyl |
| 2566 | 5-F, 6-Cl | cycPr | CH$_2$-3-Pyridyl |
| 2567 | 5-F, 6-Cl | cycPr | CH$_2$-4-Pyridyl |
| 2568 | 5-F, 6-Cl | cycPr | CH$_2$-2-furanyl |
| 2569 | 5-F, 6-Cl | cycPr | CH$_2$-3-furanyl |
| 2570 | 5-F, 6-Cl | cycPr | CH$_2$-2-thienyl |
| 2571 | 5-F, 6-Cl | cycPr | CH$_2$-3-thienyl |
| 2572 | 5-F, 6-Cl | cycPr | CH$_2$CH$_2$-cycPr |
| 2573 | 5-F, 6-Cl | cycPr | CH$_2$CH$_2$—Ph |
| 2574 | 5-F, 6-Cl | cycPr | CH$_2$CH-2-Pyridyl |
| 2575 | 5-F, 6-Cl | cycPr | CH$_2$CH-3-Pyridyl |
| 2576 | 5-F, 6-Cl | cycPr | CH$_2$CH-4-Pyridyl |
| 2577 | 5-F, 6-Cl | cycPr | CH$_2$CH$_2$-2-furanyl |
| 2578 | 5-F, 6-Cl | cycPr | CH$_2$CH$_2$-3-furanyl |
| 2579 | 5-F, 6-Cl | cycPr | CH$_2$CH$_2$-2-thienyl |
| 2580 | 5-F, 6-Cl | cycPr | CH$_2$CH$_2$-3-thienyl |
| 2581 | 5-F, 6-Cl | cycPr | C≡C—Et |
| 2582 | 5-F, 6-Cl | cycPr | C≡C-iPr |
| 2583 | 5-F, 6-Cl | cycPr | C≡C-cycPr |
| 2584 | 5-F, 6-Cl | cycPr | C≡C-1-(Me)cycPr |
| 2585 | 5-F, 6-Cl | cycPr | C≡C-2-pyridyl |
| 2586 | 5-F, 6-Cl | cycPr | C≡C-3-pyridyl |
| 2587 | 5-F, 6-Cl | cycPr | C≡C-4-pyridyl |
| 2588 | 5-F, 6-Cl | cycPr | C≡C-2-furanyl |
| 2589 | 5-F, 6-Cl | cycPr | C≡C-3-furanyl |
| 2590 | 5-F, 6-Cl | cycPr | C≡C-2-thienyl |
| 2591 | 5-F, 6-Cl | cycPr | C≡C-3-thienyl |
| 2592 | 5-F, 6-Cl | cycPr | CH=CH—Et |
| 2593 | 5-F, 6-Cl | cycPr | CH=CH-iPr |
| 2594 | 5-F, 6-Cl | cycPr | CH=CH-cycPr |
| 2595 | 5-F, 6-Cl | cycPr | CH=CH-1-(Me)cycPr |
| 2596 | 5-F, 6-Cl | cycPr | CH=CH-2-pyridyl |
| 2597 | 5-F, 6-Cl | cycPr | CH=CH-3-pyridyl |
| 2598 | 5-F, 6-Cl | cycPr | CH=CH-4-pyridyl |
| 2599 | 5-F, 6-Cl | cycPr | CH=CH-2-furanyl |
| 2600 | 5-F, 6-Cl | cycPr | CH=CH-3-furanyl |
| 2601 | 5-F, 6-Cl | cycPr | CH=CH-2-thienyl |
| 2602 | 5-F, 6-Cl | cycPr | CH=CH-3-thienyl |
| 2603 | 5-F, 6-Cl | cycPr | CH$_2$—C≡C-cycPr |
| 2604 | 5-F, 6-Cl | cycPr | CH$_2$—C≡C-2-furanyl |
| 2605 | 5-F, 6-Cl | cycPr | CH$_2$CH=CH-cycPr |
| 2606 | 5-F, 6-Cl | cycPr | CH$_2$CH=CH-2-furanyl |
| 2607 | 5-F, 6-Cl | cycPr | CH=CHCH$_2$-cycPr |
| 2608 | 5-F, 6-Cl | cycPr | CH=CHCH$_2$-2-furanyl |
| 2609 | 6-CH$_3$ | cycPr | CH$_2$CH$_2$CH$_3$ |
| 2610 | 6-CH$_3$ | cycPr | CH$_2$CH$_2$CH$_2$CH$_3$ |
| 2611 | 6-CH$_3$ | cycPr | CH$_2$CH$_2$CH$_2$CH$_2$CH$_3$ |
| 2612 | 6-CH$_3$ | cycPr | CH$_2$CH$_2$CH(CH$_3$)$_2$ |
| 2613 | 6-CH$_3$ | cycPr | CH$_2$CH$_2$-tBu |
| 2614 | 6-CH$_3$ | cycPr | CH$_2$-cycPr |
| 2615 | 6-CH$_3$ | cycPr | CH$_2$—Ph |
| 2616 | 6-CH$_3$ | cycPr | CH$_2$-2-Pyridyl |
| 2617 | 6-CH$_3$ | cycPr | CH$_2$-3-Pyridyl |
| 2618 | 6-CH$_3$ | cycPr | CH$_2$-4-Pyridyl |
| 2619 | 6-CH$_3$ | cycPr | CH$_2$-2-furanyl |
| 2620 | 6-CH$_3$ | cycPr | CH$_2$-3-furanyl |
| 2621 | 6-CH$_3$ | cycPr | CH$_2$-2-thienyl |
| 2622 | 6-CH$_3$ | cycPr | CH$_2$-3-thienyl |
| 2623 | 6-CH$_3$ | cycPr | CH$_2$CH$_2$-cycPr |
| 2624 | 6-CH$_3$ | cycPr | CH$_2$CH$_2$—Ph |
| 2625 | 6-CH$_3$ | cycPr | CH$_2$CH$_2$-2-Pyridyl |
| 2626 | 6-CH$_3$ | cycPr | CH$_2$CH$_2$-3-Pyridyl |
| 2627 | 6-CH$_3$ | cycPr | CH$_2$CH$_2$-4-Pyridyl |
| 2628 | 6-CH$_3$ | cycPr | CH$_2$CH$_2$-2-furanyl |
| 2629 | 6-CH$_3$ | cycPr | CH$_2$CH$_2$-3-furanyl |
| 2630 | 6-CH$_3$ | cycPr | CH$_2$CH$_2$-2-thienyl |
| 2631 | 6-CH$_3$ | cycPr | CH$_2$CH$_2$-3-thienyl |
| 2632 | 6-CH$_3$ | cycPr | C≡C—Et |
| 2633 | 6-CH$_3$ | cycPr | C≡C-iPr |
| 2634 | 6-CH$_3$ | cycPr | C≡C-cycPr |
| 2635 | 6-CH$_3$ | cycPr | C≡C-1-(Me)cycPr |
| 2636 | 6-CH$_3$ | cycPr | C≡C-2-pyridyl |
| 2637 | 6-CH$_3$ | cycPr | C≡C-3-pyridyl |
| 2638 | 6-CH$_3$ | cycPr | C≡C-4-pyridyl |
| 2639 | 6-CH$_3$ | cycPr | C≡C-2-furanyl |
| 2640 | 6-CH$_3$ | cycPr | C≡C-3-furanyl |
| 2641 | 6-CH$_3$ | cycPr | C≡C-2-thienyl |
| 2642 | 6-CH$_3$ | cycPr | C≡C-3-thienyl |
| 2643 | 6-CH$_3$ | cycPr | CH=CH—Et |
| 2644 | 6-CH$_3$ | cycPr | CH=CH-iPr |
| 2645 | 6-CH$_3$ | cycPr | CH=CH-cycPr |
| 2646 | 6-CH$_3$ | cycPr | CH=CH-1-(Me)cycPr |
| 2647 | 6-CH$_3$ | cycPr | CH=CH-2-pyridyl |
| 2648 | 6-CH$_3$ | cycPr | CH=CH-3-pyridyl |
| 2649 | 6-CH$_3$ | cycPr | CH=CH-4-pyridyl |
| 2650 | 6-CH$_3$ | cycPr | CH=CH-2-furanyl |
| 2651 | 6-CH$_3$ | cycPr | CH=CH-3-furanyl |
| 2652 | 6-CH$_3$ | cycPr | CH=CH-2-thienyl |
| 2653 | 6-CH$_3$ | cycPr | CH=CH-3-thienyl |
| 2654 | 6-CH$_3$ | cycPr | CH$_2$—C≡C-cycPr |
| 2655 | 6-CH$_3$ | cycPr | CH$_2$—C≡C-2-furanyl |
| 2656 | 6-CH$_3$ | cycPr | CH$_2$CH=CH-cycPr |
| 2657 | 6-CH$_3$ | cycPr | CH$_2$CH=CH-2-furanyl |
| 2658 | 6-CH$_3$ | cycPr | CH=CHCH$_2$-cycPr |
| 2659 | 6-CH$_3$ | cycPr | CH=CHCH$_2$-2-furanyl |
| 2660 | 6-OCH$_3$ | cycPr | CH$_2$CH$_2$CH$_3$ |
| 2661 | 6-OCH$_3$ | cycPr | CH$_2$CH$_2$CH$_2$CH$_3$ |
| 2662 | 6-OCH$_3$ | cycPr | CH$_2$CH$_2$CH$_2$CH$_2$CH$_3$ |
| 2663 | 6-OCH$_3$ | cycPr | CH$_2$CH$_2$CH(CH$_3$)$_2$ |
| 2664 | 6-OCH$_3$ | cycPr | CH$_2$CH$_2$-tBu |
| 2665 | 6-OCH$_3$ | cycPr | CH$_2$-cycPr |
| 2666 | 6-OCH$_3$ | cycPr | CH$_2$—Ph |
| 2667 | 6-OCH$_3$ | cycPr | CH$_2$-2-Pyridyl |
| 2668 | 6-OCH$_3$ | cycPr | CH$_2$-3-Pyridyl |
| 2669 | 6-OCH$_3$ | cycPr | CH$_2$-4-Pyridyl |
| 2670 | 6-OCH$_3$ | cycPr | CH$_2$-2-furanyl |
| 2671 | 6-OCH$_3$ | cycPr | CH$_2$-3-furanyl |
| 2672 | 6-OCH$_3$ | cycPr | CH$_2$-2-thienyl |
| 2673 | 6-OCH$_3$ | cycPr | CH$_2$-3-thienyl |
| 2674 | 6-OCH$_3$ | cycPr | CH$_2$CH$_2$-cycPr |
| 2675 | 6-OCH$_3$ | cycPr | CH$_2$CH$_2$—Ph |
| 2676 | 6-OCH$_3$ | cycPr | CH$_2$CH$_2$-2-Pyridyl |
| 2677 | 6-OCH$_3$ | cycPr | CH$_2$CH$_2$-3-Pyridyl |
| 2678 | 6-OCH$_3$ | cycPr | CH$_2$CH$_2$-4-Pyridyl |
| 2679 | 6-OCH$_3$ | cycPr | CH$_2$CH$_2$-2-furanyl |
| 2680 | 6-OCH$_3$ | cycPr | CH$_2$CH$_2$-3-furanyl |
| 2681 | 6-OCH$_3$ | cycPr | CH$_2$CH$_2$-2-thienyl |
| 2682 | 6-OCH$_3$ | cycPr | CH$_2$CH$_2$-3-thienyl |
| 2683 | 6-OCH$_3$ | cycPr | C≡C—Et |
| 2684 | 6-OCH$_3$ | cycPr | C≡C-iPr |
| 2685 | 6-OCH$_3$ | cycPr | C≡C-cycPr |
| 2686 | 6-OCH$_3$ | cycPr | C≡C-1-(Me)cycPr |
| 2687 | 6-OCH$_3$ | cycPr | C≡C-2-pyridyl |
| 2688 | 6-OCH$_3$ | cycPr | C≡C-3-pyridyl |
| 2689 | 6-OCH$_3$ | cycPr | C≡C-4-pyridyl |
| 2690 | 6-OCH$_3$ | cycPr | C≡C-2-furanyl |
| 2691 | 6-OCH$_3$ | cycPr | C≡C-3-furanyl |
| 2692 | 6-OCH$_3$ | cycPr | C≡C-2-thienyl |
| 2693 | 6-OCH$_3$ | cycPr | C≡C-3-thienyl |
| 2694 | 6-OCH$_3$ | cycPr | CH=CH—Et |
| 2695 | 6-OCH$_3$ | cycPr | CH=CH-iPr |
| 2696 | 6-OCH$_3$ | cycPr | CH=CH-cycPr |
| 2697 | 6-OCH$_3$ | cycPr | CH=CH-1-(Me)cycPr |
| 2698 | 6-OCH$_3$ | cycPr | CH=CH-2-pyridyl |
| 2699 | 6-OCH$_3$ | cycPr | CH=CH-3-pyridyl |
| 2700 | 6-OCH$_3$ | cycPr | CH=CH-4-pyridyl |
| 2701 | 6-OCH$_3$ | cycPr | CH=CH-2-furanyl |
| 2702 | 6-OCH$_3$ | cycPr | CH=CH-3-furanyl |
| 2703 | 6-OCH$_3$ | cycPr | CH=CH-2-thienyl |
| 2704 | 6-OCH$_3$ | cycPr | CH=CH-3-thienyl |
| 2705 | 6-OCH$_3$ | cycPr | CH$_2$—C≡C-cycPr |
| 2706 | 6-OCH$_3$ | cycPr | CH$_2$—C≡C-2-furanyl |
| 2707 | 6-OCH$_3$ | cycPr | CH$_2$CH=CH-cycPr |
| 2708 | 6-OCH$_3$ | cycPr | CH$_2$CH=CH-2-furanyl |
| 2709 | 6-OCH$_3$ | cycPr | CH=CHCH$_2$-cycPr |
| 2710 | 6-OCH$_3$ | cycPr | CH=CHCH$_2$-2-furanyl |
| 2711 | 5,6-OCH$_2$O— | cycPr | CH$_2$CH$_2$CH$_3$ |
| 2712 | 5,6-OCH$_2$O— | cycPr | CH$_2$CH$_2$CH$_2$CH$_3$ |
| 2713 | 5,6-OCH$_2$O— | cycPr | CH$_2$CH$_2$CH$_2$CH$_2$CH$_3$ |
| 2714 | 5,6-OCH$_2$O— | cycPr | CH$_2$CH$_2$CH(CH$_3$)$_2$ |
| 2715 | 5,6-OCH$_2$O— | cycPr | CH$_2$CH$_2$-tBu |

TABLE 2-continued

| | | | |
|---|---|---|---|
| 2716 | 5,6-OCH$_2$O— | cycPr | CH$_2$-cycPr |
| 2717 | 5,6-OCH$_2$O— | cycPr | CH$_2$—Ph |
| 2718 | 5,6-OCH$_2$O— | cycPr | CH$_2$-2-Pyridyl |
| 2719 | 5,6-OCH$_2$O— | cycPr | CH$_2$-3-Pyridyl |
| 2720 | 5,6-OCH$_2$O— | cycPr | CH$_2$-4-Pyridyl |
| 2721 | 5,6-OCH$_2$O— | cycPr | CH$_2$-2-furanyl |
| 2722 | 5,6-OCH$_2$O— | cycPr | CH$_2$-3-furanyl |
| 2723 | 5,6-OCH$_2$O— | cycPr | CH$_2$-2-thienyl |
| 2724 | 5,6-OCH$_2$O— | cycPr | CH$_2$-3-thienyl |
| 2725 | 5,6-OCH$_2$O— | cycPr | CH$_2$CH$_2$-cycPr |
| 2726 | 5,6-OCH$_2$O— | cycPr | CH$_2$CH$_2$—Ph |
| 2727 | 5,6-OCH$_2$O— | cycPr | CH$_2$CH$_2$-2-Pyridyl |
| 2728 | 5,6-OCH$_2$O— | cycPr | CH$_2$CH$_2$-3-Pyridyl |
| 2729 | 5,6-OCH$_2$O— | cycPr | CH$_2$CH$_2$-4-Pyridyl |
| 2730 | 5,6-OCH$_2$O— | cycPr | CH$_2$CH$_2$-2-furanyl |
| 2731 | 5,6-OCH$_2$O— | cycPr | CH$_2$CH$_2$-3-furanyl |
| 2732 | 5,6-OCH$_2$O— | cycPr | CH$_2$CH$_2$-2-thienyl |
| 2733 | 5,6-OCH$_2$O— | cycPr | CH$_2$CH$_2$-3-thienyl |
| 2734 | 5,6-OCH$_2$O— | cycPr | C≡C—Et |
| 2735 | 5,6-OCH$_2$O— | cycPr | C≡C-iPr |
| 2736 | 5,6-OCH$_2$O— | cycPr | C≡C-cycPr |
| 2737 | 5,6-OCH$_2$O— | cycPr | C≡C-1-(Me)cycPr |
| 2738 | 5,6-OCH$_2$O— | cycPr | C≡C-2-pyridyl |
| 2739 | 5,6-OCH$_2$O— | cycPr | C≡C-3-pyridyl |
| 2740 | 5,6-OCH$_2$O— | cycPr | C≡C-4-pyridyl |
| 2741 | 5,6-OCH$_2$O— | cycPr | C≡C-2-furanyl |
| 2742 | 5,6-OCH$_2$O— | cycPr | C≡C-3-furanyl |
| 2743 | 5,6-OCH$_2$O— | cycPr | C≡C-2-thienyl |
| 2744 | 5,6-OCH$_2$O— | cycPr | C≡C-3-thienyl |
| 2745 | 5,6-OCH$_2$O— | cycPr | CH=CH—Et |
| 2746 | 5,6-OCH$_2$O— | cycPr | CH=CH-iPr |
| 2747 | 5,6-OCH$_2$O— | cycPr | CH=CH-cycPr |
| 2748 | 5,6-OCH$_2$O— | cycPr | CH=CH-1-(Me)cycPr |
| 2749 | 5,6-OCH$_2$O— | cycPr | CH=CH-2-pyridyl |
| 2750 | 5,6-OCH$_2$O— | cycPr | CH=CH-3-pyridyl |
| 2751 | 5,6-OCH$_2$O— | cycPr | CH=CH-4-pyridyl |
| 2752 | 5,6-OCH$_2$O— | cycPr | CH=CH-2-furanyl |
| 2753 | 5,6-OCH$_2$O— | cycPr | CH=CH-3-furanyl |
| 2754 | 5,6-OCH$_2$O— | cycPr | CH=CH-2-thienyl |
| 2755 | 5,6-OCH$_2$O— | cycPr | CH=CH-3-thienyl |
| 2756 | 5,6-OCH$_2$O— | cycPr | CH$_2$—C≡C-cycPr |
| 2757 | 5,6-OCH$_2$O— | cycPr | CH$_2$—C≡C-2-furanyl |
| 2758 | 5,6-OCH$_2$O— | cycPr | CH$_2$CH=CH-cycPr |
| 2759 | 5,6-OCH$_2$O— | cycPr | CH$_2$CH=CH-2-furanyl |
| 2760 | 5,6-OCH$_2$O— | cycPr | CH=CHCH$_2$-cycPr |
| 2761 | 5,6-OCH$_2$O— | cycPr | CH=CHCH$_2$-2-furanyl |

TABLE 3

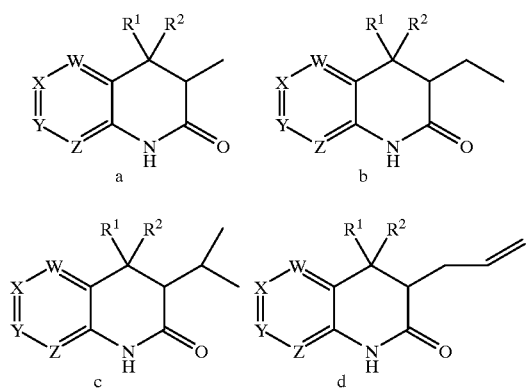

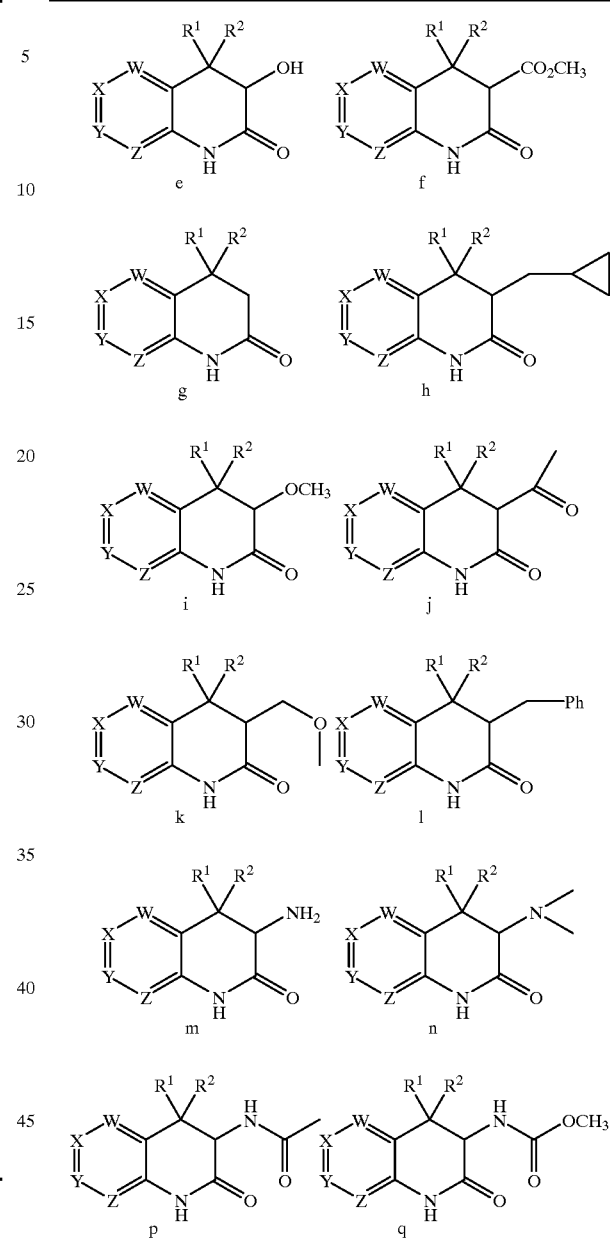

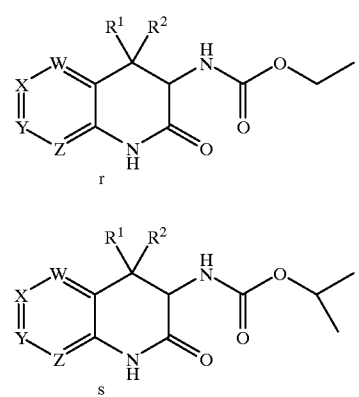

TABLE 3-continued

| Ex. # | W | X | Y | Z | R¹ | R² |
|---|---|---|---|---|---|---|
| 3001 | CH | CCl | CH | N | $CF_3$ | C≡C-nPr |
| 3002 | CH | CCl | CH | N | $CF_3$ | C≡C-Bu |
| 3003 | CH | CCl | CH | N | $CF_3$ | C≡C-iBu |
| 3004 | CH | CCl | CH | N | $CF_3$ | C≡C-tBu |
| 3005 | CH | CCl | CH | N | $CF_3$ | C≡C—Et |
| 3006 | CH | CCl | CH | N | $CF_3$ | C≡C—Me |
| 3007 | CH | CCl | CH | N | $CF_3$ | C≡C—Ph |
| 3008 | CH | CCl | CH | N | $CF_3$ | C≡C-cycPr |
| 3009 | CH | CCl | CH | N | $CF_3$ | C≡C-1-(Me)cycPr |
| 3010 | CH | CCl | CH | N | $CF_3$ | C≡C-2-Pyridyl |
| 3011 | CH | CCl | CH | N | $CF_3$ | C≡C-3-Pyridyl |
| 3012 | CH | CCl | CH | N | $CF_3$ | C≡C-4-Pyridyl |
| 3013 | CH | CCl | CH | N | $CF_3$ | C≡C-2-furanyl |
| 3014 | CH | CCl | CH | N | $CF_3$ | C≡C-3-furanyl |
| 3015 | CH | CCl | CH | N | $CF_3$ | C≡C-2-thienyl |
| 3016 | CH | CCl | CH | N | $CF_3$ | C≡C-3-thienyl |
| 3017 | CH | CCl | CH | N | $CF_3$ | CH=CH-cycPr |
| 3018 | CH | CCl | CH | N | $CF_3$ | CH=CH-iPr |
| 3019 | CH | CCl | CH | N | $CF_3$ | CH=CH-nPr |
| 3020 | CH | CCl | CH | N | $CF_3$ | CH=CH—Bu |
| 3021 | CH | CCl | CH | N | $CF_3$ | CH=CH-iBu |
| 3022 | CH | CCl | CH | N | $CF_3$ | CH=CH-tBu |
| 3023 | CH | CCl | CH | N | $CF_3$ | CH=CH—Et |
| 3024 | CH | CCl | CH | N | $CF_3$ | CH=CH—Me |
| 3025 | CH | CCl | CH | N | $CF_3$ | CH=CH—Ph |
| 3026 | CH | CCl | CH | N | $CF_3$ | CH=CH-2-Pyridyl |
| 3027 | CH | CCl | CH | N | $CF_3$ | CH=CH-3-Pyridyl |
| 3028 | CH | CCl | CH | N | $CF_3$ | CH=CH-4-Pyridyl |
| 3029 | CH | CCl | CH | N | $CF_3$ | CH=CH-2-furanyl |
| 3030 | CH | CCl | CH | N | $CF_3$ | CH=CH-3-furanyl |
| 3031 | CH | CCl | CH | N | $CF_3$ | CH=CH-2-thienyl |
| 3032 | CH | CCl | CH | N | $CF_3$ | CH=CH-3-thienyl |
| 3033 | CH | CCl | CH | N | $CF_3$ | $CH_2CH_2CH_2CH_2CH_3$ |
| 3034 | CH | CCl | CH | N | $CF_3$ | $CH_2CH_2CH(CH_3)_2$ |
| 3035 | CH | CCl | CH | N | $CF_3$ | $CH_2CH_2CH_2CH_3$ |
| 3036 | CH | CCl | CH | N | $CF_3$ | $CH_2CH_2CH_3$ |
| 3037 | CH | CCl | CH | N | $CF_3$ | $CH_2CH_2$-cycPr |
| 3038 | CH | CCl | CH | N | $CF_3$ | $CH_2CH_2$-tBu |
| 3039 | CH | CCl | CH | N | $CF_3$ | $CH_2CH_2$-2-Pyridyl |
| 3040 | CH | CCl | CH | N | $CF_3$ | $CH_2CH_2$-3-Pyridyl |
| 3041 | CH | CCl | CH | N | $CF_3$ | $CH_2CH_2$-4-Pyridyl |
| 3042 | CH | CCl | CH | N | $CF_3$ | $CH_2CH_2$-2-furanyl |
| 3043 | CH | CCl | CH | N | $CF_3$ | $CH_2CH_2$-3-furanyl |
| 3044 | CH | CCl | CH | N | $CF_3$ | $CH_2CH_2$-2-thienyl |
| 3045 | CH | CCl | CH | N | $CF_3$ | $CH_2CH_2$-3-thienyl |
| 3046 | CH | C(OCH$_3$) | CH | N | $CF_3$ | C≡C-cycPr |
| 3047 | CH | C(OCH$_3$) | CH | N | $CF_3$ | C≡C-1-(Me)cycPr |
| 3048 | CH | C(OCH$_3$) | CH | N | $CF_3$ | C≡C-iPr |
| 3049 | CH | C(OCH$_3$) | CH | N | $CF_3$ | C≡C-nPr |
| 3050 | CH | C(OCH$_3$) | CH | N | $CF_3$ | C≡C-Bu |
| 3051 | CH | C(OCH$_3$) | CH | N | $CF_3$ | C≡C-iBu |
| 3052 | CH | C(OCH$_3$) | CH | N | $CF_3$ | C≡C-tBu |
| 3053 | CH | C(OCH$_3$) | CH | N | $CF_3$ | C≡C—Et |
| 3054 | CH | C(OCH$_3$) | CH | N | $CF_3$ | C≡C—Me |
| 3055 | CH | C(OCH$_3$) | CH | N | $CF_3$ | C≡C—Ph |
| 3056 | CH | C(OCH$_3$) | CH | N | $CF_3$ | C≡C-2-Pyridyl |
| 3057 | CH | C(OCH$_3$) | CH | N | $CF_3$ | C≡C-3-Pyridyl |
| 3058 | CH | C(OCH$_3$) | CH | N | $CF_3$ | C≡C-4-Pyridyl |
| 3059 | CH | C(OCH$_3$) | CH | N | $CF_3$ | C≡C-2-furanyl |
| 3060 | CH | C(OCH$_3$) | CH | N | $CF_3$ | C≡C-3-furanyl |
| 3061 | CH | C(OCH$_3$) | CH | N | $CF_3$ | C≡C-2-thienyl |
| 3062 | CH | C(OCH$_3$) | CH | N | $CF_3$ | C≡C-3-thienyl |
| 3063 | CH | C(OCH$_3$) | CH | N | $CF_3$ | CH=CH-cycPr |
| 3064 | CH | C(OCH$_3$) | CH | N | $CF_3$ | CH=CH-iPr |
| 3065 | CH | C(OCH$_3$) | CH | N | $CF_3$ | CH=CH-nPr |
| 3066 | CH | C(OCH$_3$) | CH | N | $CF_3$ | CH=CH—Bu |
| 3067 | CH | C(OCH$_3$) | CH | N | $CF_3$ | CH=CH-iBu |
| 3068 | CH | C(OCH$_3$) | CH | N | $CF_3$ | CH=CH-tBu |
| 3069 | CH | C(OCH$_3$) | CH | N | $CF_3$ | CH=CH—Et |
| 3070 | CH | C(OCH$_3$) | CH | N | $CF_3$ | CH=CH—Me |
| 3071 | CH | C(OCH$_3$) | CH | N | $CF_3$ | CH=CH—Ph |
| 3072 | CH | C(OCH$_3$) | CH | N | $CF_3$ | CH=CH-2-Pyridyl |
| 3073 | CH | C(OCH$_3$) | CH | N | $CF_3$ | CH=CH-3-Pyridyl |
| 3074 | CH | C(OCH$_3$) | CH | N | $CF_3$ | CH=CH-4-Pyridyl |
| 3075 | CH | C(OCH$_3$) | CH | N | $CF_3$ | CH=CH-2-furanyl |
| 3076 | CH | C(OCH$_3$) | CH | N | $CF_3$ | CH=CH-3-furanyl |
| 3077 | CH | C(OCH$_3$) | CH | N | $CF_3$ | CH=CH-2-thienyl |
| 3078 | CH | C(OCH$_3$) | CH | N | $CF_3$ | CH=CH-3-thienyl |
| 3079 | CH | C(OCH$_3$) | CH | N | $CF_3$ | $CH_2CH_2CH_2CH_2CH_3$ |
| 3080 | CH | C(OCH$_3$) | CH | N | $CF_3$ | $CH_2CH_2CH(CH_3)_2$ |
| 3081 | CH | C(OCH$_3$) | CH | N | $CF_3$ | $CH_2CH_2CH_2CH_3$ |
| 3082 | CH | C(OCH$_3$) | CH | N | $CF_3$ | $CH_2CH_2CH_3$ |
| 3083 | CH | C(OCH$_3$) | CH | N | $CF_3$ | $CH_2CH_2$-cycPr |
| 3084 | CH | C(OCH$_3$) | CH | N | $CF_3$ | $CH_2CH_2$-tBu |
| 3085 | CH | C(OCH$_3$) | CH | N | $CF_3$ | $CH_2CH_2$—Ph |
| 3086 | CH | C(OCH$_3$) | CH | N | $CF_3$ | $CH_2CH_2$-2-Pyridyl |
| 3087 | CH | C(OCH$_3$) | CH | N | $CF_3$ | $CH_2CH_2$-3-Pyridyl |
| 3088 | CH | C(OCH$_3$) | CH | N | $CF_3$ | $CH_2CH_2$-4-Pyridyl |
| 3089 | CH | C(OCH$_3$) | CH | N | $CF_3$ | $CH_2CH_2$-2-furanyl |
| 3090 | CH | C(OCH$_3$) | CH | N | $CF_3$ | $CH_2CH_2$-3-furanyl |
| 3091 | CH | C(OCH$_3$) | CH | N | $CF_3$ | $CH_2CH_2$-2-thienyl |
| 3092 | CH | C(OCH$_3$) | CH | N | $CF_3$ | $CH_2CH_2$-3-thienyl |
| 3093 | CH | CH | CH | N | $CF_3$ | C≡C-cycPr |
| 3094 | CH | CH | CH | N | $CF_3$ | C≡C-1-(Me)cycPr |
| 3095 | CH | CH | CH | N | $CF_3$ | C≡C-iPr |
| 3096 | CH | CH | CH | N | $CF_3$ | C≡C-nPr |
| 3097 | CH | CH | CH | N | $CF_3$ | C≡C—Et |
| 3098 | CH | CH | CH | N | $CF_3$ | C≡C-3-Pyridyl |
| 3099 | CH | CH | CH | N | $CF_3$ | C≡C-2-furanyl |
| 3100 | CH | CH | CH | N | $CF_3$ | C≡C-3-furanyl |
| 3101 | CH | CH | CH | N | $CF_3$ | C≡C-2-thienyl |
| 3102 | CH | CH | CH | N | $CF_3$ | C≡C-3-thienyl |
| 3103 | CH | CCl | N | CH | $CF_3$ | C≡C-iPr |
| 3104 | CH | CCl | N | CH | $CF_3$ | C≡C-nPr |
| 3105 | CH | CCl | N | CH | $CF_3$ | C≡C—Bu |
| 3106 | CH | CCl | N | CH | $CF_3$ | C≡C-iBu |
| 3107 | CH | CCl | N | CH | $CF_3$ | C≡C-tBu |
| 3108 | CH | CCl | N | CH | $CF_3$ | C≡C—Et |
| 3109 | CH | CCl | N | CH | $CF_3$ | C≡C—Me |
| 3110 | CH | CCl | N | CH | $CF_3$ | C≡C—Ph |
| 3111 | CH | CCl | N | CH | $CF_3$ | C≡C-cycPr |
| 3112 | CH | CCl | N | CH | $CF_3$ | C≡C-1-(Me)cycPr |
| 3113 | CH | CCl | N | CH | $CF_3$ | C≡C-2-Pyridyl |
| 3114 | CH | CCl | N | CH | $CF_3$ | C≡C-3-Pyridyl |
| 3115 | CH | CCl | N | CH | $CF_3$ | C≡C-4-Pyridyl |
| 3116 | CH | CCl | N | CH | $CF_3$ | C≡C-2-furanyl |
| 3117 | CH | CCl | N | CH | $CF_3$ | C≡C-3-furanyl |
| 3118 | CH | CCl | N | CH | $CF_3$ | C≡C-2-thienyl |
| 3119 | CH | CCl | N | CH | $CF_3$ | C≡C-3-thienyl |
| 3120 | CH | CCl | N | CH | $CF_3$ | CH=CH-cycPr |
| 3121 | CH | CCl | N | CH | $CF_3$ | CH=CH-iPr |
| 3122 | CH | CCl | N | CH | $CF_3$ | CH=CH-nPr |
| 3123 | CH | CCl | N | CH | $CF_3$ | CH=CH—Bu |
| 3124 | CH | CCl | N | CH | $CF_3$ | CH=CH-iBu |
| 3125 | CH | CCl | N | CH | $CF_3$ | CH=CH-tBu |
| 3126 | CH | CCl | N | CH | $CF_3$ | CH=CH—Et |
| 3127 | CH | CCl | N | CH | $CF_3$ | CH=CH—Me |
| 3128 | CH | CCl | N | CH | $CF_3$ | CH=CH—Ph |
| 3129 | CH | CCl | N | CH | $CF_3$ | CH=CH-2-Pyridyl |
| 3130 | CH | CCl | N | CH | $CF_3$ | CH=CH-3-Pyridyl |
| 3131 | CH | CCl | N | CH | $CF_3$ | CH=CH-4-Pyridyl |
| 3132 | CH | CCl | N | CH | $CF_3$ | CH=CH-2-furanyl |
| 3133 | CH | CCl | N | CH | $CF_3$ | CH=CH-3-furanyl |
| 3134 | CH | CCl | N | CH | $CF_3$ | CH=CH-2-thienyl |
| 3135 | CH | CCl | N | CH | $CF_3$ | CH=CH-3-thienyl |
| 3136 | CH | CCl | N | CH | $CF_3$ | $CH_2CH_2CH_2CH_2CH_3$ |
| 3137 | CH | CCl | N | CH | $CF_3$ | $CH_2CH_2CH(CH_3)_2$ |
| 3138 | CH | CCl | N | CH | $CF_3$ | $CH_2CH_2CH_2CH_3$ |
| 3139 | CH | CCl | N | CH | $CF_3$ | $CH_2CH_2CH_3$ |
| 3140 | CH | CCl | N | CH | $CF_3$ | $CH_2CH_2$-cycPr |
| 3141 | CH | CCl | N | CH | $CF_3$ | $CH_2CH_2$-tBu |
| 3142 | CH | CCl | N | CH | $CF_3$ | $CH_2CH_2$—Ph |
| 3143 | CH | CCl | N | CH | $CF_3$ | $CH_2CH_2$-2-Pyridyl |
| 3144 | CH | CCl | N | CH | $CF_3$ | $CH_2CH_2$-3-Pyridyl |
| 3145 | CH | CCl | N | CH | $CF_3$ | $CH_2CH_2$-4-Pyridyl |
| 3146 | CH | CCl | N | CH | $CF_3$ | $CH_2CH_2$-2-furanyl |
| 3147 | CH | CCl | N | CH | $CF_3$ | $CH_2CH_2$-3-furanyl |
| 3148 | CH | CCl | N | CH | $CF_3$ | $CH_2CH_2$-2-furanyl |
| 3149 | CH | CCl | N | CH | $CF_3$ | $CH_2CH_2$-3-furanyl |
| 3150 | CH | C(OCH$_3$) | N | CH | $CF_3$ | C≡C-iPr |
| 3151 | CH | C(OCH$_3$) | N | CH | $CF_3$ | C≡C-nPr |
| 3152 | CH | C(OCH$_3$) | N | CH | $CF_3$ | C≡C—Bu |
| 3153 | CH | C(OCH$_3$) | N | CH | $CF_3$ | C≡C-iBu |
| 3154 | CH | C(OCH$_3$) | N | CH | $CF_3$ | C≡C-tBu |
| 3155 | CH | C(OCH$_3$) | N | CH | $CF_3$ | C≡C—Et |
| 3156 | CH | C(OCH$_3$) | N | CH | $CF_3$ | C≡C—Me |

TABLE 3-continued

| | | | | | | |
|---|---|---|---|---|---|---|
| 3157 | CH | C(OCH₃) | N | CH | CF₃ | C≡C—Ph |
| 3158 | CH | C(OCH₃) | N | CH | CF₃ | C≡C-cycPr |
| 3159 | CH | C(OCH₃) | N | CH | CF₃ | C≡C-1-(Me)cycPr |
| 3160 | CH | C(OCH₃) | N | CH | CF₃ | C≡C-2-Pyridyl |
| 3161 | CH | C(OCH₃) | N | CH | CF₃ | C≡C-3-Pyridyl |
| 3162 | CH | C(OCH₃) | N | CH | CF₃ | C≡C-4-Pyridyl |
| 3163 | CH | C(OCH₃) | N | CH | CF₃ | C≡C-2-furanyl |
| 3164 | CH | C(OCH₃) | N | CH | CF₃ | C≡C-3-furanyl |
| 3165 | CH | C(OCH₃) | N | CH | CF₃ | C≡C-2-thienyl |
| 3166 | CH | C(OCH₃) | N | CH | CF₃ | C≡C-3-thienyl |
| 3167 | CH | C(OCH₃) | N | CH | CF₃ | CH=CH-cycPr |
| 3168 | CH | C(OCH₃) | N | CH | CF₃ | CH=CH-iPr |
| 3169 | CH | C(OCH₃) | N | CH | CF₃ | CH=CH-nPr |
| 3170 | CH | C(OCH₃) | N | CH | CF₃ | CH=CH—Bu |
| 3171 | CH | C(OCH₃) | N | CH | CF₃ | CH=CH-iBu |
| 3172 | CH | C(OCH₃) | N | CH | CF₃ | CH=CH-tBu |
| 3173 | CH | C(OCH₃) | N | CH | CF₃ | CH=CH—Et |
| 3174 | CH | C(OCH₃) | N | CH | CF₃ | CH=CH—Me |
| 3175 | CH | C(OCH₃) | N | CH | CF₃ | CH=CH—Ph |
| 3176 | CH | C(OCH₃) | N | CH | CF₃ | CH=CH-2-Pyridyl |
| 3177 | CH | C(OCH₃) | N | CH | CF₃ | CH=CH-3-Pyridyl |
| 3178 | CH | C(OCH₃) | N | CH | CF₃ | CH=CH-4-Pyridyl |
| 3179 | CH | C(OCH₃) | N | CH | CF₃ | CH=CH-2-furanyl |
| 3180 | CH | C(OCH₃) | N | CH | CF₃ | CH=CH-3-furanyl |
| 3181 | CH | C(OCH₃) | N | CH | CF₃ | CH=CH-2-thienyl |
| 3182 | CH | C(OCH₃) | N | CH | CF₃ | CH=CH-3-thienyl |
| 3183 | CH | C(OCH₃) | N | CH | CF₃ | CH₂CH₂CH₂CH₂CH₃ |
| 3184 | CH | C(OCH₃) | N | CH | CF₃ | CH₂CH₂CH(CH₃)₂ |
| 3185 | CH | C(OCH₃) | N | CH | CF₃ | CH₂CH₂CH₂CH₃ |
| 3186 | CH | C(OCH₃) | N | CH | CF₃ | CH₂CH₂CH₃ |
| 3187 | CH | C(OCH₃) | N | CH | CF₃ | CH₂CH₂-cycPr |
| 3188 | CH | C(OCH₃) | N | CH | CF₃ | CH₂CH₂-tBu |
| 3189 | CH | C(OCH₃) | N | CH | CF₃ | CH₂CH₂—Ph |
| 3190 | CH | C(OCH₃) | N | CH | CF₃ | CH₂CH₂-2-Pyridyl |
| 3191 | CH | C(OCH₃) | N | CH | CF₃ | CH₂CH₂-3-Pyridyl |
| 3192 | CH | C(OCH₃) | N | CH | CF₃ | CH₂CH₂-4-Pyridyl |
| 3193 | CH | C(OCH₃) | N | CH | CF₃ | CH₂CH₂-2-furanyl |
| 3194 | CH | C(OCH₃) | N | CH | CF₃ | CH₂CH₂-3-furanyl |
| 3195 | CH | C(OCH₃) | N | CH | CF₃ | CH₂CH₂-2-thienyl |
| 3196 | CH | C(OCH₃) | N | CH | CF₃ | CH₂CH₂-3-thienyl |
| 3197 | CH | CH | N | CH | CF₃ | C≡C-cycPr |
| 3198 | CH | CH | N | CH | CF₃ | C≡C-1-(Me)cycPr |
| 3199 | CH | CH | N | CH | CF₃ | C≡C-iPr |
| 3200 | CH | CH | N | CH | CF₃ | C≡C-nPr |
| 3201 | CH | CH | N | CH | CF₃ | C≡C—Et |
| 3202 | CH | CH | N | CH | CF₃ | C≡C-3-Pyridyl |
| 3203 | CH | CH | N | CH | CF₃ | C≡C-2-furanyl |
| 3204 | CH | CH | N | CH | CF₃ | C≡C-3-furanyl |
| 3205 | CH | CH | N | CH | CF₃ | C≡C-2-thienyl |
| 3206 | CH | CH | N | CH | CF₃ | C≡C-3-thienyl |
| 3207 | CCl | N | CH | CH | CF₃ | C≡C-cycPr |
| 3208 | CCl | N | CH | CH | CF₃ | C≡C-1-(Me)cycPr |
| 3209 | CCl | N | CH | CH | CF₃ | C≡C-iPr |
| 3210 | CCl | N | CH | CH | CF₃ | C≡C-nPr |
| 3211 | CCl | N | CH | CH | CF₃ | C≡C—Bu |
| 3212 | CCl | N | CH | CH | CF₃ | C≡C-iBu |
| 3213 | CCl | N | CH | CH | CF₃ | C≡C-tBu |
| 3214 | CCl | N | CH | CH | CF₃ | C≡C—Et |
| 3215 | CCl | N | CH | CH | CF₃ | C≡C—Me |
| 3216 | CCl | N | CH | CH | CF₃ | C≡C—Ph |
| 3217 | CCl | N | CH | CH | CF₃ | C≡C-2-Pyridyl |
| 3218 | CCl | N | CH | CH | CF₃ | C≡C-3-Pyridyl |
| 3219 | CCl | N | CH | CH | CF₃ | C≡C-4-Pyridyl |
| 3220 | CCl | N | CH | CH | CF₃ | C≡C-2-furanyl |
| 3221 | CCl | N | CH | CH | CF₃ | C≡C-3-furanyl |
| 3222 | CCl | N | CH | CH | CF₃ | C≡C-2-thienyl |
| 3223 | CCl | N | CH | CH | CF₃ | C≡C-3-thienyl |
| 3224 | CCl | N | CH | CH | CF₃ | CH=CH-cycPr |
| 3225 | CCl | N | CH | CH | CF₃ | CH=CH-iPr |
| 3226 | CCl | N | CH | CH | CF₃ | CH=CH-nPr |
| 3227 | CCl | N | CH | CH | CF₃ | CH=CH—Bu |
| 3228 | CCl | N | CH | CH | CF₃ | CH=CH-iBu |
| 3229 | CCl | N | CH | CH | CF₃ | CH=CH-tBu |
| 3230 | CCl | N | CH | CH | CF₃ | CH=CH—Et |
| 3231 | CCl | N | CH | CH | CF₃ | CH=CH—Me |
| 3232 | CCl | N | CH | CH | CF₃ | CH=CH—Ph |
| 3233 | CCl | N | CH | CH | CF₃ | CH=CH-2-Pyridyl |
| 3234 | CCl | N | CH | CH | CF₃ | CH=CH-3-Pyridyl |
| 3235 | CCl | N | CH | CH | CF₃ | CH=CH-4-Pyridyl |
| 3236 | CCl | N | CH | CH | CF₃ | CH=CH-2-furanyl |
| 3237 | CCl | N | CH | CH | CF₃ | CH=CH-3-furanyl |
| 3238 | CCl | N | CH | CH | CF₃ | CH=CH-2-thienyl |
| 3239 | CCl | N | CH | CH | CF₃ | CH=CH-3-thienyl |
| 3240 | CCl | N | CH | CH | CF₃ | CH₂CH₂CH₂CH₂CH₃ |
| 3241 | CCl | N | CH | CH | CF₃ | CH₂CH₂CH(CH₃)₂ |
| 3242 | CCl | N | CH | CH | CF₃ | CH₂CH₂CH₂CH₃ |
| 3243 | CCl | N | CH | CH | CF₃ | CH₂CH₂CH₃ |
| 3244 | CCl | N | CH | CH | CF₃ | CH₂CH₂-cycPr |
| 3245 | CCl | N | CH | CH | CF₃ | CH₂CH₂-tBu |
| 3246 | CCl | N | CH | CH | CF₃ | CH₂CH₂—Ph |
| 3247 | CCl | N | CH | CH | CF₃ | CH₂CH₂-2-Pyridyl |
| 3248 | CCl | N | CH | CH | CF₃ | CH₂CH₂-3-Pyridyl |
| 3249 | CCl | N | CH | CH | CF₃ | CH₂CH₂-4-Pyridyl |
| 3250 | CCl | N | CH | CH | CF₃ | CH₂CH₂-2-furanyl |
| 3251 | CCl | N | CH | CH | CF₃ | CH₂CH₂-3-furanyl |
| 3252 | CCl | N | CH | CH | CF₃ | CH₂CH₂-2-thienyl |
| 253 | CCl | N | CH | CH | CF₃ | CH₂CH₂-3-thienyl |
| 2254 | CH | N | CH | CH | CF₃ | C≡C-iPr |
| 2255 | CH | N | CH | CH | CF₃ | C≡C-nPr |
| 2256 | CH | N | CH | CH | CF₃ | C≡C—Et |
| 2257 | CH | N | CH | CH | CF₃ | C≡C-cycPr |
| 2258 | CH | N | CH | CH | CF₃ | C≡C-1-(Me)cycPr |
| 2259 | CH | N | CH | CH | CF₃ | C≡C-3-Pyridyl |
| 2260 | CH | N | CH | CH | CF₃ | C≡C-2-furanyl |
| 2261 | CH | N | CH | CH | CF₃ | C≡C-3-furanyl |
| 2262 | CH | N | CH | CH | CF₃ | C≡C-2-thienyl |
| 2263 | CH | N | CH | CH | CF₃ | C≡C-3-thienyl |
| 2264 | N | CCl | CH | CH | CF₃ | C≡C-cycPr |
| 2265 | N | CCl | CH | CH | CF₃ | C≡C-1-(Me)cycPr |
| 2266 | N | CCl | CH | CH | CF₃ | C≡C-iPr |
| 2267 | N | CCl | CH | CH | CF₃ | C≡C-nPr |
| 2268 | N | CCl | CH | CH | CF₃ | C≡C—Bu |
| 2269 | N | CCl | CH | CH | CF₃ | C≡C-iBu |
| 2270 | N | CCl | CH | CH | CF₃ | C≡C-tBu |
| 2271 | N | CCl | CH | CH | CF₃ | C≡C—Et |
| 2272 | N | CCl | CH | CH | CF₃ | C≡C—Me |
| 2273 | N | CCl | CH | CH | CF₃ | C≡C—Ph |
| 2274 | N | CCl | CH | CH | CF₃ | C≡C-2-Pyridyl |
| 2275 | N | CCl | CH | CH | CF₃ | C≡C-3-Pyridyl |
| 3276 | N | CCl | CH | CH | CF₃ | C≡C-4-Pyridyl |
| 3277 | N | CCl | CH | CH | CF₃ | C≡C-2-furanyl |
| 3278 | N | CCl | CH | CH | CF₃ | C≡C-3-furanyl |
| 3279 | N | CCl | CH | CH | CF₃ | C≡C-2-thienyl |
| 3280 | N | CCl | CH | CH | CF₃ | C≡C-3-thienyl |
| 3281 | N | CCl | CH | CH | CF₃ | CH=CH-cycPr |
| 3282 | N | CCl | CH | CH | CF₃ | CH=CH-iPr |
| 3283 | N | CCl | CH | CH | CF₃ | CH=CH-nPr |
| 3284 | N | CCl | CH | CH | CF₃ | CH=CH—Bu |
| 3285 | N | CCl | CH | CH | CF₃ | CH=CH-iBu |
| 3286 | N | CCl | CH | CH | CF₃ | CH=CH-tBu |
| 3287 | N | CCl | CH | CH | CF₃ | CH=CH—Et |
| 3288 | N | CCl | CH | CH | CF₃ | CH=CH—Me |
| 3289 | N | CCl | CH | CH | CF₃ | CH=CH—Ph |
| 3290 | N | CCl | CH | CH | CF₃ | CH=CH-2-Pyridyl |
| 3291 | N | CCl | CH | CH | CF₃ | CH=CH-3-Pyridyl |
| 3292 | N | CCl | CH | CH | CF₃ | CH=CH-4-Pyridyl |
| 3293 | N | CCl | CH | CH | CF₃ | CH=CH-2-furanyl |
| 3294 | N | CCl | CH | CH | CF₃ | CH=CH-3-furanyl |
| 3295 | N | CCl | CH | CH | CF₃ | CH=CH-2-thienyl |
| 3296 | N | CCl | CH | CH | CF₃ | CH=CH-3-thienyl |
| 3297 | N | CCl | CH | CH | CF₃ | CH₂CH₂CH₂CH₂CH₃ |
| 3298 | N | CCl | CH | CH | CF₃ | CH₂CH₂CH(CH₃)₂ |
| 3299 | N | CCl | CH | CH | CF₃ | CH₂CH₂CH₂CH₃ |
| 3300 | N | CCl | CH | CH | CF₃ | CH₂CH₂CH₃ |
| 3301 | N | CCl | CH | CH | CF₃ | CH₂CH₂-cycPr |
| 3302 | N | CCl | CH | CH | CF₃ | CH₂CH₂-tBu |
| 3303 | N | CCl | CH | CH | CF₃ | CH₂CH₂—Ph |
| 3304 | N | CCl | CH | CH | CF₃ | CH₂CH₂-2-Pyridyl |
| 3305 | N | CCl | CH | CH | CF₃ | CH₂CH₂-3-Pyridyl |
| 3306 | N | CCl | CH | CH | CF₃ | CH₂CH₂-4-Pyridyl |
| 3307 | N | CCl | CH | CH | CF₃ | CH₂CH₂-2-furanyl |
| 3308 | N | CCl | CH | CH | CF₃ | CH₂CH₂-3-furanyl |
| 3309 | N | CCl | CH | CH | CF₃ | CH₂CH₂-2-thienyl |
| 3310 | N | CCl | CH | CH | CF₃ | CH₂CH₂-3-thienyl |
| 3311 | N | C(OCH₃) | CH | CH | CF₃ | C≡C-cycPr |
| 3312 | N | C(OCH₃) | CH | CH | CF₃ | C≡C-1-(Me)cycPr |
| 3313 | N | C(OCH₃) | CH | CH | CF₃ | C≡C-iPr |
| 3314 | N | C(OCH₃) | CH | CH | CF₃ | C≡C-nPr |

TABLE 3-continued

| | | | | | |
|---|---|---|---|---|---|
| 3315 | N | C(OCH$_3$) | CH | CH | CF$_3$ C≡C—Bu |
| 3316 | N | C(OCH$_3$) | CH | CH | CF$_3$ C≡C-iBu |
| 3317 | N | C(OCH$_3$) | CH | CH | CF$_3$ C≡C-tBu |
| 3318 | N | C(OCH$_3$) | CH | CH | CF$_3$ C≡C—Et |
| 3319 | N | C(OCH$_3$) | CH | CH | CF$_3$ C≡C—Me |
| 3320 | N | C(OCH$_3$) | CH | CH | CF$_3$ C≡C—Ph |
| 3321 | N | C(OCH$_3$) | CH | CH | CF$_3$ C≡C-2-Pyridyl |
| 3322 | N | C(OCH$_3$) | CH | CH | CF$_3$ C≡C-3-Pyridyl |
| 3323 | N | C(OCH$_3$) | CH | CH | CF$_3$ C≡C-4-Pyridyl |
| 3324 | N | C(OCH$_3$) | CH | CH | CF$_3$ C≡C-2-furanyl |
| 3325 | N | C(OCH$_3$) | CH | CH | CF$_3$ C≡C-3-furanyl |
| 3326 | N | C(OCH$_3$) | CH | CH | CF$_3$ C≡C-2-thienyl |
| 3327 | N | C(OCH$_3$) | CH | CH | CF$_3$ C≡C-3-thienyl |
| 3328 | N | C(OCH$_3$) | CH | CH | CF$_3$ CH=CH-cycPr |
| 3329 | N | C(OCH$_3$) | CH | CH | CF$_3$ CH=CH-iPr |
| 3330 | N | C(OCH$_3$) | CH | CH | CF$_3$ CH=CH-nPr |
| 3331 | N | C(OCH$_3$) | CH | CH | CF$_3$ CH=CH—Bu |
| 3332 | N | C(OCH$_3$) | CH | CH | CF$_3$ CH=CH-iBu |
| 3333 | N | C(OCH$_3$) | CH | CH | CF$_3$ CH=CH-tBu |
| 3334 | N | C(OCH$_3$) | CH | CH | CF$_3$ CH=CH—Et |
| 3335 | N | C(OCH$_3$) | CH | CH | CF$_3$ CH=CH—Me |
| 3336 | N | C(OCH$_3$) | CH | CH | CF$_3$ CH=CH—Ph |
| 3337 | N | C(OCH$_3$) | CH | CH | CF$_3$ CH=CH-2-Pyridyl |
| 3338 | N | C(OCH$_3$) | CH | CH | CF$_3$ CH=CH-3-Pyridyl |
| 3339 | N | C(OCH$_3$) | CH | CH | CF$_3$ CH=CH-4-Pyridyl |
| 3340 | N | C(OCH$_3$) | CH | CH | CF$_3$ CH=CH-2-furanyl |
| 3341 | N | C(OCH$_3$) | CH | CH | CF$_3$ CH=CH-3-furanyl |
| 3342 | N | C(OCH$_3$) | CH | CH | CF$_3$ CH=CH-2-thienyl |
| 3343 | N | C(OCH$_3$) | CH | CH | CF$_3$ CH=CH-3-thienyl |
| 3344 | N | C(OCH$_3$) | CH | CH | CF$_3$ CH$_2$CH$_2$CH$_2$CH$_2$CH$_3$ |
| 3345 | N | C(OCH$_3$) | CH | CH | CF$_3$ CH$_2$CH$_2$CH(CH$_3$)$_2$ |
| 3346 | N | C(OCH$_3$) | CH | CH | CF$_3$ CH$_2$CH$_2$CH$_2$CH$_3$ |
| 3347 | N | C(OCH$_3$) | CH | CH | CF$_3$ CH$_2$CH$_2$CH$_3$ |
| 3348 | N | C(OCH$_3$) | CH | CH | CF$_3$ CH$_2$CH$_2$-cycPr |
| 3349 | N | C(OCH$_3$) | CH | CH | CF$_3$ CH$_2$CH$_2$-tBu |
| 3350 | N | C(OCH$_3$) | CH | CH | CF$_3$ CH$_2$CH$_2$—Ph |
| 3351 | N | C(OCH$_3$) | CH | CH | CF$_3$ CH$_2$CH$_2$-2-Pyridyl |
| 3352 | N | C(OCH$_3$) | CH | CH | CF$_3$ CH$_2$CH$_2$-3-Pyridyl |
| 3353 | N | C(OCH$_3$) | CH | CH | CF$_3$ CH$_2$CH$_2$-4-Pyridyl |
| 3354 | N | C(OCH$_3$) | CH | CH | CF$_3$ CH$_2$CH$_2$-2-furanyl |
| 3355 | N | C(OCH$_3$) | CH | CH | CF$_3$ CH$_2$CH$_2$-3-furanyl |
| 3356 | N | C(OCH$_3$) | CH | CH | CF$_3$ CH$_2$CH$_2$-2-thienyl |
| 3357 | N | C(OCH$_3$) | CH | CH | CF$_3$ CH$_2$CH$_2$-3-thienyl |
| 3358 | N | CH | CH | CH | CF$_3$ C≡C-cycPr |
| 3359 | N | CH | CH | CH | CF$_3$ C≡C-1-(Me)cycPr |
| 3360 | N | CH | CH | CH | CF$_3$ C≡C-iPr |
| 3361 | N | CH | CH | CH | CF$_3$ C≡C-nPr |
| 3362 | N | CH | CH | CH | CF$_3$ C≡C—Et |
| 3363 | N | CH | CH | CH | CF$_3$ C≡C-3-Pyridyl |
| 3364 | N | CH | CH | CH | CF$_3$ C≡C-2-furanyl |
| 3365 | N | CH | CH | CH | CF$_3$ C≡C-3-furanyl |
| 3366 | N | CH | CH | CH | CF$_3$ C≡C-2-thienyl |
| 3367 | N | CH | CH | CH | CF$_3$ C≡C-3-thienyl |

Utility

The compounds of this invention possess reverse transcriptase inhibitory activity, in particular, HIV inhibitory efficacy. The compounds of Formula (I) possess HIV reverse transcriptase inhibitory activity and are therefore useful as antiviral agents for the treatment of HIV infection and associated diseases. The compounds of Formula (I) possess HIV reverse transcriptase inhibitory activity and are effective as inhibitors of HIV growth. The ability of the compounds of the present invention to inhibit viral growth or infectivity is demonstrated in standard assay of viral growth or infectivity, for example, using the assay described below.

The compounds of Formula (I) of the present invention are also useful for the inhibition of HIV in an ex vivo sample containing HIV or expected to be exposed to HIV. Thus, the compounds of the present invention may be used to inhibit HIV present in a body fluid sample (for example, a serum or semen sample) which contains or is suspected to contain or be exposed to HIV.

The compounds provided by this invention are also useful as standard or reference compounds for use in tests or assays for determining the ability of an agent to inhibit viral clone replication and/or HIV reverse transcriptase, for example in a pharmaceutical research program. Thus, the compounds of the present invention may be used as a control or reference compound in such assays and as a quality control standard. The compounds of the present invention may be provided in a commercial kit or container for use as such standard or reference compound.

Since the compounds of the present invention exhibit specificity for HIV reverse transcriptase, the compounds of the present invention may also be useful as diagnostic reagents in diagnostic assays for the detection of HIV reverse transcriptase. Thus, inhibition of the reverse transcriptase activity in an assay (such as the assays described herein) by a compound of the present invention would be indicative of the presence of HIV reverse transcriptase and HIV virus.

As used herein "µg" denotes microgram, "mg" denotes milligram, "g" denotes gram, "µL" denotes microliter, "mL" denotes milliliter, "L" denotes liter, "nM" denotes nanomolar, "µM" denotes micromolar, "mM" denotes millimolar, "M" denotes molar and "nm" denotes nanometer. "Sigma" stands for the Sigma-Aldrich Corp. of St. Louis, Mo.

HIV RNA Assay

DNA Plasmids and In Vitro RNA Transcripts:

Plasmid pDAB 72 containing both gag and pol sequences of BH10 (bp 113–1816) cloned into PTZ 19R was prepared according to Erickson-Viitanen et al. *AIDS Research and Human Retroviruses* 1989, 5, 577. The plasmid was linearized with Bam HI prior to the generation of in vitro RNA transcripts using the Riboprobe Gemini system II kit (Promega) with T7 RNA polymerase. Synthesized RNA was purified by treatment with RNase free DNAse (Promega), phenol-chloroform extraction, and ethanol precipitation. RNA transcripts were dissolved in water, and stored at −70° C. The concentration of RNA was determined from the A$_{260}$.

Probes:

Biotinylated capture probes were purified by HPLC after synthesis on an Applied Biosystems (Foster City, Calif.) DNA synthesizer by addition of biotin to the 5' terminal end of the oligonucleotide, using the biotin-phosphoramidite reagent of Cocuzza, *Tet. Lett.* 1989, 30, 6287. The gag biotinylated capture probe (5-biotin-CTAGCTCCCTGCTTGCCCATACTA 3') was complementary to nucleotides 889–912 of HXB2 and the pol biotinylated capture probe (5'-biotin—CCCTATCATTTTTGGTTTCCAT 3') was complementary to nucleotides 2374–2395 of HXB2. Alkaline phosphatase conjugated oligonucleotides used as reporter probes were prepared by Syngene (San Diego, Calif.). The pol reporter probe (5' CTGTCTTACTTTGATAAAACCTC 3') was complementary to nucleotides 2403–2425 of HXB2. The gag reporter probe (5' CCCAGTATTTGTCTACAGC-CTTCT 3') was complementary to nucleotides 950–973 of HXB2. All nucleotide positions are those of the GenBank Genetic Sequence Data Bank as accessed through the Genetics Computer Group Sequence Analysis Software Package (Devereau *Nucleic Acids Research* 1984, 12, 387). The reporter probes were prepared as 0.5 µM stocks in 2×SSC (0.3 M NaCl, 0.03 M sodium citrate), 0.05 M Tris pH 8.8, 1 mg/mL BSA. The biotinylated capture probes were prepared as 100 µM stocks in water.

Streptavidin Coated Plates:

Streptavidin coated plates were obtained from Du Pont Biotechnology Systems (Boston, Mass.).

Cells and Virus Stocks:

MT-2 and MT-4 cells were maintained in RPMI 1640 supplemented with 5% fetal calf serum (FCS) for MT-2 cells or 10% FCS for MT-4 cells, 2 mM L-glutamine and 50 µg/mL gentamycin, all from Gibco. HIV-1 RF was propagated in MT-4 cells in the same medium. Virus stocks were prepared approximately 10 days after acute infection of MT-4 cells and stored as aliquots at −70° C. Infectious titers of HIV-1(RF) stocks were $1-3\times10^7$ PFU (plaque forming units)/mL as measured by plaque assay on MT-2 cells (see below). Each aliquot of virus stock used for infection was thawed only once.

For evaluation of antiviral efficacy, cells to be infected were subcultured one day prior to infection. On the day of infection, cells were resuspended at $5\times10^5$ cells/mL in RPMI 1640, 5% FCS for bulk infections or at $2\times10^6$/mL in Dulbecco's modified Eagles medium with 5% FCS for infection in microtiter plates. Virus was added and culture continued for 3 days at 37° C.

HIV RNA Assay:

Cell lysates or purified RNA in 3 M or 5 M GED were mixed with 5 M GED and capture probe to a final guanidinium isothiocyanate concentration of 3 M and a final biotin oligonucleotide concentration of 30 nM. Hybridization was carried out in sealed U bottom 96 well tissue culture plates (Nunc or Costar) for 16–20 hours at 37° C. RNA hybridization reactions were diluted three-fold with deionized water to a final guanidinium isothiocyanate concentration of 1 M and aliquots (150 µL) were transferred to streptavidin coated microtiter plates wells. Binding of capture probe and capture probe-RNA hybrid to the immobilized streptavidin was allowed to proceed for 2 hours at room temperature, after which the plates were washed 6 times with DuPont ELISA plate wash buffer (phosphate buffered saline(PBS), 0.05% Tween 20.) A second hybridization of reporter probe to the immobilized complex of capture probe and hybridized target RNA was carried out in the washed streptavidin coated well by addition of 120 µl of a hybridization cocktail containing 4×SSC, 0.66% Triton X 100, 6.66% deionized formamide, 1 mg/mL BSA and 5 nM reporter probe. After hybridization for one hour at 37° C., the plate was again washed 6 times. Immobilized alkaline phosphatase activity was detected by addition of 100 µL of 0.2 mM 4-methylumbelliferyl phosphate (MUBP, JBL Scientific) in bufferδ (2.5 M diethanolamine pH 8.9 (JBL Scientific), 10 mM $MgCl_2$, 5 mM zinc acetate dihydrate and 5 mM N-hydroxyethyl-ethylene-diamine-triacetic acid). The plates were incubated at 37° C. Fluorescence at 450 nM was measured using a microplate fluorometer (Dynateck) exciting at 365 nM.

Microplate Based Compound Evaluation in HIV-1 Infected MT-2 Cells:

Compounds to be evaluated were dissolved in DMSO and diluted in culture medium to twice the highest concentration to be tested and a maximum DMSO concentration of 2%. Further three-fold serial dilutions of the compound in culture medium were performed directly in U bottom microtiter plates (Nunc). After compound dilution, MT-2 cells (50 µL) were added to a final concentration of $5\times10^5$ per mL ($1\times10^5$ per well). Cells were incubated with compounds for 30 minutes at 37° C. in a $CO_2$ incubator. For evaluation of antiviral potency, an appropriate dilution of HIV-1 (RF) virus stock (50 µL) was added to culture wells containing cells and dilutions of the test compounds. The final volume in each well was 200 µL. Eight wells per plate were left uninfected with 50 µL of medium added in place of virus, while eight wells were infected in the absence of any antiviral compound. For evaluation of compound toxicity, parallel plates were cultured without virus infection.

After 3 days of culture at 37° C. in a humidified chamber inside a $CO_2$ incubator, all but 25 µL of medium/well was removed from the HIV infected plates. Thirty seven µL of 5 M GED containing biotinylated capture probe was added to the settled cells and remaining medium in each well to a final concentration of 3 M GED and 30 nM capture probe. Hybridization of the capture probe to HIV RNA in the cell lysate was carried out in the same microplate well used for virus culture by sealing the plate with a plate sealer (Costar), and incubating for 16–20 hrs in a 37° C. incubator. Distilled water was then added to each well to dilute the hybridization reaction three-fold and 150 µL of this diluted mixture was transferred to a streptavidin coated microtiter plate. HIV RNA was quantitated as described above. A standard curve, prepared by adding known amounts of pDAB 72 in vitro RNA transcript to wells containing lysed uninfected cells, was run on each microtiter plate in order to determine the amount of viral RNA made during the infection.

In order to standardize the virus inoculum used in the evaluation of compounds for antiviral activity, dilutions of virus were selected which resulted in an $IC_{90}$ value (concentration of compound required to reduce the HIV RNA level by 90%) for dideoxycytidine (ddC) of 0.2 µg/mL. $IC_{90}$ values of other antiviral compounds, both more and less potent than ddC, were reproducible using several stocks of HIV-1 (RF) when this procedure was followed. This concentration of virus corresponded to $\sim3\times10^5$ PFU (measured by plaque assay on MT-2 cells) per assay well and typically produced approximately 75% of the maximum viral RNA level achievable at any virus inoculum. For the HIV RNA assay, $IC_{90}$ values were determined from the percent reduction of net signal (signal from infected cell samples minus signal from uninfected cell samples) in the RNA assay relative to the net signal from infected, untreated cells on the same culture plate (average of eight wells). Valid performance of individual infection and RNA assay tests was judged according to three criteria. It was required that the virus infection should result in an RNA assay signal equal to or greater than the signal generated from 2 ng of pDAB 72 in vitro RNA transcript. The $IC_{90}$ for ddC, determined in each assay run, should be between 0.1 and 0.3 µg/mL. Finally, the plateau level of viral RNA produced by an effective reverse transcriptase inhibitor should be less than 10% of the level achieved in an uninhibited infection. A compound was considered active if its $IC_{90}$ was found to be less than 20 µM. Representative compounds of the present invention have been shown to exhibit $IC_{90}$ values less than 20 µM.

For antiviral potency tests, all manipulations in microtiter plates, following the initial addition of 2×concentrated compound solution to a single row of wells, were performed using a Perkin Elmer/Cetus ProPette.

Protein Binding and Mutant Resistance

In order to characterize NNRTI analogs for their clinical efficacy potential the effect of plasma proteins on antiviral potency and measurements of antiviral potency against wild type and mutant variants of HIV which carry amino acid changes in the known binding site for NNRTIs were examined. The rationale for this testing strategy is two fold:

1. Many drugs are extensively bound to plasma proteins. Although the binding affinity for most drugs for the major components of human plasma, namely, human serum albumin (HSA) or alpha-1-acid glycoprotein (AAG), is low, these major components are present in high concentration in the blood. Only free or unbound drug is available to cross the infected cell membrane for interaction with the target site (i.e., HIV-1 reverse transcriptase, HIV-1 RT). Therefore, the effect of added HSA+AAG on the antiviral potency in tissue culture more closely reflects the potency of a given compound in the clinical setting. The concentration of compound required for 90% inhibition of virus replication as measured in a sensitive viral RNA-based detection method is designated the IC90. The fold increase in apparent IC90 for test compounds in the presence or added levels of HSA and AAG that reflect in vivo concentrations (45 mg/ml HSA, 1 mg/ml AAG) was then calculated. The lower the fold increase, the more compound will be available to interact with the target site.

2. The combination of the high rate of virus replication in the infected individual and the poor fidelity of the viral RT results in the production of a quasi-species or mixtures of HIV species in the infected individual. These species will include a majority wild type species, but also mutant variants of HIV and the proportion of a given mutant will reflect its relative fitness and replication rate. Because mutant variants including mutants with changes in the amino acid sequence of the viral RT likely pre-exist in the infected individual's quasi-species, the overall potency observed in the clinical setting will reflect the ability of a drug to inhibit not only wild type HIV-1, but mutant variants as well. We thus have constructed, in a known genetic background, mutant variants of HIV-1 which carry amino acid substitutions at positions thought to be involved in NNRTI binding, and measured the ability of test compounds to inhibit replication of these mutant viruses. The concentration of compound required for 90% inhibition of virus replication as measured in a sensitive viral RNA-based detection method is designated the IC90. It is desirable to have a compound which has high activity against a variety of mutants.

Dosage and Formulation

The antiviral compounds of this invention can be administered as treatment for viral infections by any means that produces contact of the active agent with the agent's site of action, i.e., the viral reverse transcriptase, in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences*, supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

Combination of Components (a) and (b)

Each therapeutic agent component of this invention can independently be in any dosage form, such as those described above, and can also be administered in various ways, as described above. In the following description component (b) is to be understood to represent one or more agents as described previously. Thus, if components (a) and (b) are to be treated the same or independently, each agent of component (b) may also be treated the same or independently.

Components (a) and (b) of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the revserse order. If component (b) contains more that one agent, e.g., one RT inhibitor and one protease inhibitor, these agents may be administered together or in any order. When not administered at the same time, preferably the administration of component (a) and (b) occurs less than about one hour apart. Preferably, the route of administration of component (a) and (b) is oral. The terms oral agent, oral inhibitor, oral compound, or the like, as used herein, denote compounds which may be orally administered. Although it is preferable that component (a) and component (b) both be administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (a) and (b) of the present invention will be readily ascertainable by a medical practitioner skilled in the art, based upon the present disclosure. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 70–80% relative to the usual dosage of the component when it is administered alone as a single agent for the treatment of HIV infection, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose or other appropriate materials as known in the art, in order to further separate the active components. The polymer coating serves to form an additional barrier to interaction with the other component. In each formulation wherein contact is prevented between components (a) and (b) via a coating or some other material, contact may also be prevented between the individual agents of component (b).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of HIV infection, which comprise a therapeutically effective amount of a pharmaceutical composition comprising a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers of materials may comprise separate containers, or one or more multi-part containers, as desired. Component (a) and component (b), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Obviously, numerous modifications and variations of the present invention are possible in light of the above teachings. It is therefore to be understood that within the scope of the appended claims, the invention may be practiced otherwise than as specifically described herein.

What is claimed is:

1. A compound of Formula (II):

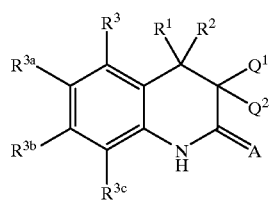

(II)

wherein:

A is O;

$R^1$ is —$CF_3$ or —$CF_2CF_3$;

$R^2$ is selected from
$C_{1-3}$ alkyl substituted with 0–1 $R^4$,
$C_{2-3}$ alkenyl substituted with 0–1 $R^4$, and
$C_{2-3}$ alkynyl substituted with 0–1 $R^4$, $R^3$ is selected from H, methyl, ethyl, —OH, methoxy, ethoxy, —$OCF_3$, F, Cl, Br, I, —$NR^{14}R^{15}$, —$NO_2$, —CN, —$C(O)R^{16}$, —$NHC(O)R^{17}$, and —$NHC(O)NR^{14}R^{15}$;

$R^{3a}$ is selected from H, methyl, ethyl, —OH, methoxy, ethoxy, —$OCF_3$, F, Cl, Br, I, —$NR^{14}R^{15}$, —$NO_2$, —CN, —$C(O)R^{16}$, —$NHC(O)R^{17}$, and —$NHC(O)NR^{14}R^{15}$;

$R^{3b}$ is H or F;

$R^{3c}$ is selected from H, methyl, —OH, methoxy, and —$OCF_3$;

$R^4$ is selected from
cyclopropyl substituted with 0–1 $R^5$,
phenyl substituted with 0–3 $R^5$, and a
5–6 membered heterocyclic system containing 1–3 heteroatoms selected from O, N, and S, substituted with 0–1 $R^5$, wherein the heterocyclic system is selected from 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, 1-pyrazolyl, 3-pyrazolyl, and 4-pyrazolyl;

$R^5$, at each occurrence, is independently selected from methyl, ethyl, propyl, —OH, methoxy, ethoxy, propoxy, —$OCF_3$, F, Cl, Br, I, —$NR^{14}R^{15}$, —$NO_2$, —CN, —$C(O)R^{16}$, —$NHC(O)R^{17}$, —$NHC(O)NR^{14}R^{15}$, —$NHSO_2R^{18}$, and —$SO_2NR^{14}R^{15}$;

$Q^1$ is selected from:
H, —CHO, —$CO_2R^7$, —$CH_2OR^7$, —$COR^7$, —$NO_2$, —$NH_2$, —$NHR^7$, —$N(R^7)_2$, —$NHCO_2R^7$, —$NHCOR^7$, —$OR^7$, —$OCOR^7$, —$CF_3$, —$CF_2CF_3$, —$CF_2CF_2CF_3$,
$C_{1-4}$ alkyl substituted with 0–1 $R^8$,
$C_{2-3}$ alkenyl substituted with 0–1 $R^8$, and
$C_{2-3}$ alkynyl substituted with 0–1 $R^8$;

$Q^2$ is H;

alternatively, $Q^1$ and $Q^2$ can be taken together to form =O;

$R^7$ is selected from
H, —$CF_3$, —$CF_2CF_3$, —$CF_2CF_2CF_3$,
$C_{1-3}$ alkyl substituted with 0–1 $R^8$,
$C_{2-3}$ alkenyl substituted with 0–1 $R^9$,
$C_{2-3}$ alkynyl substituted with 0–1 $R^9$,
$C_{3-6}$ cycloalkyl substituted with 0–2 $R^9$, and
phenyl substituted with 0–2 $R^9$;

$R^8$ is selected from
methyl, ethyl, propyl, butyl, —OH, methoxy, ethoxy, propoxy, butoxy, —$OCF_3$, F, Cl, Br, I, —$NR^{14}R^{15}$, —$NO_2$, —CN, —$C(O)R^{16}$, —$NHC(O)R^{17}$, —$NHC(O)NR^{14}R^{15}$,
$C_{3-6}$ cycloalkyl substituted with 0–2 $R^9$,
phenyl substituted with 0–5 $R^9$, and
5–6 membered heterocyclic system containing 1–3 heteroatoms selected from O, N, and S, substituted with 0–2 $R^9$; wherein the heterocyclic system is selected from 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, 1-pyrazolyl, 3-pyrazolyl, and 4-pyrazolyl;

$R^9$ is selected from methyl, ethyl, propyl, butyl, —$CF_3$, —$CF_2CF_3$, —$CF_2CF_2CF_3$, —OH, methoxy, ethoxy, propoxy, butoxy, —$OCF_3$, F, Cl, Br, I, —$NR^{14}R^{15}$, —$NO_2$, —CN, —$C(O)R^{16}$, —$NHC(O)R^{17}$, —$NHC(O)NR^{14}R^{15}$, —$NHSO_2R^{18}$, and —$SO_2NR^{14}R^{15}$;

$R^{14}$ and $R^{15}$ are independently selected from H, methyl, and ethyl;

$R^{16}$ is selected from H, OH, methyl, ethyl, methoxy, ethoxy, and $NR^{14}R^{15}$;

$R^{17}$ is selected from methyl, ethyl, methoxy, and ethoxy; and $R^{18}$ is selected from methyl, ethyl, and phenyl.

2. A compound according to claim 1 which is:

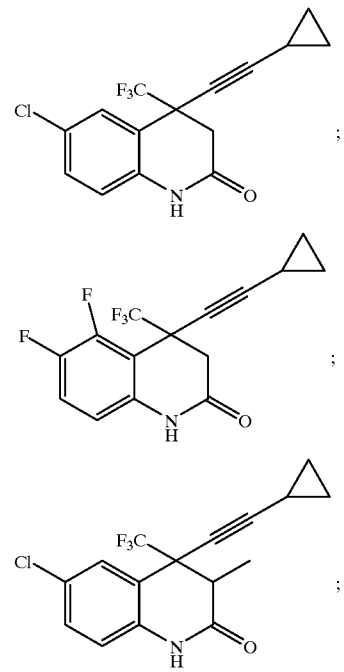

-continued

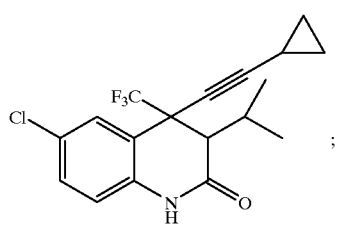

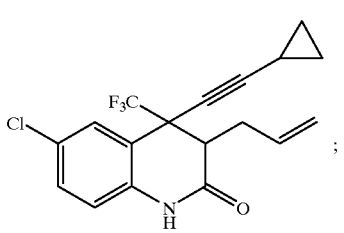

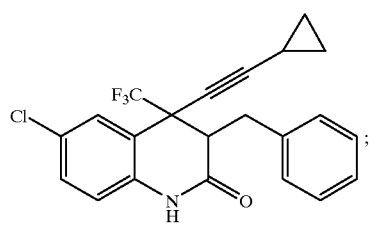

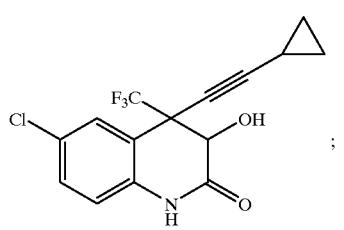

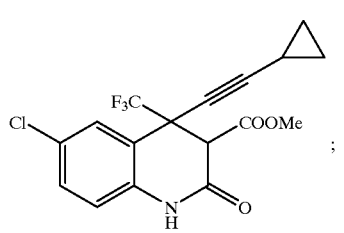

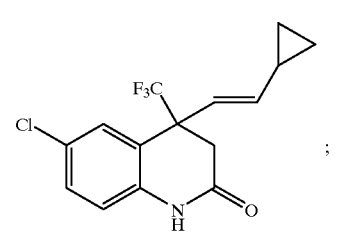

-continued

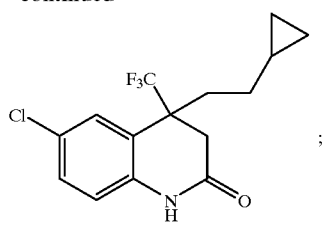

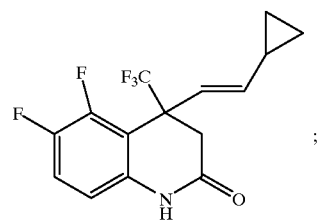

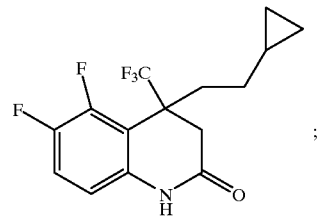

or a pharmaceutically acceptable salt thereof.

3. A compound according to claim 1, wherein the compound is of Formula (II a):

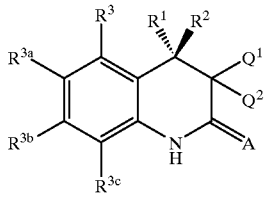

(IIa)

or pharmaceutically acceptable salt thereof.

4. A compound according to claim 1, wherein the compound is of Formula (IIb):

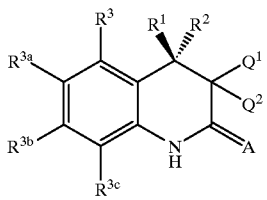

(IIb)

or pharmaceutically acceptable salt thereof.

5. A pharmaceutical composition, comprising: a pharmaceutically acceptable carrier and a therapeutically effective amount of a compound of claim 1.

6. A method for treating HIV infection, comprising: administering to a host in need of such treatment a therapeutically effective amount of a compound of claim 1, or a pharmaceutically acceptable salt form thereof.

7. A compound according to claim 1 of Formula (II):

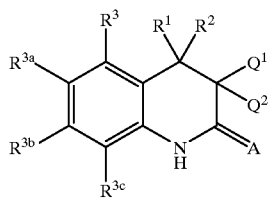

(II)

wherein:
A is O;
R$^1$ is —CF$_3$;
R$^2$ is selected from
  C$_{1-3}$ alkyl substituted with 0–1 R$^4$,
  C$_{2-3}$ alkenyl substituted with 0–1 R$^4$, and
  C$_{2-3}$ alkynyl substituted with 0–1 R$^4$,
R$^3$ is selected from H, methyl, —OH, methoxy, —OCF$_3$, F, Cl, and —CN;
R$^{3a}$ is selected from H, methyl, —OH, methoxy, —OCF$_3$, F, Cl, and —CN;
R$^{3b}$ is H;
R$^{3c}$ is selected from H, methyl, —OH, and methoxy;
R$^4$ is selected from
  cyclopropyl substituted with 0–1 R$^5$,
  phenyl substituted with 0–3 R$^5$, and a
  5–6 membered heterocyclic system containing 1–3 heteroatoms selected from O, N, and S, substituted with 0–1 R$^5$, wherein the heterocyclic system is selected from 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, 1-pyrazolyl, 3-pyrazolyl, and 4-pyrazolyl;
R$^5$, at each occurrence, is independently selected from methyl, ethyl, propyl, —OH, methoxy, ethoxy, propoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;
Q$^1$ is selected from:
  H, —CHO, —CO$_2$R$^7$, —CH$_2$OR$^7$, —COR$^7$, —NO$_2$, —NH$_2$, NHR$^7$, —N(R$^7$)$_2$, —NHCO$_2$R$^7$, —NHCOR$^7$, —OR$^7$, —OCOR$^7$, —CF$_3$, —CF$_2$CF$_3$, —CF$_2$CF$_2$CF$_3$,
  C$_{1-4}$ alkyl substituted with 0–1 R$^8$,
  C$_{2-3}$ alkenyl substituted with 0–1 R$^8$, and
  C$_{2-3}$ alkynyl substituted with 0–1 R$^8$;
Q$^2$ is H;
alternatively, Q$^1$ and Q$^2$ can be taken together to form =O;
R$^7$ is selected from
  H, —CF$_3$, —CF$_2$CF$_3$, —CF$_2$CF$_2$CF$_3$,
  C$_{1-3}$ alkyl substituted with 0–1 R$^8$,
  C$_{2-3}$ alkenyl substituted with 0–1 R$^9$,
  C$_{2-3}$ alkynyl substituted with 0–1 R$^9$,
  C$_{3-6}$ cycloalkyl substituted with 0–2 R$^9$, and
  phenyl substituted with 0–2 R$^9$;
R$^8$ is selected from
  methyl, ethyl, propyl, butyl, —OH, methoxy, ethoxy, propoxy, butoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$,
  C$_{3-6}$ cycloalkyl substituted with 0–2 R$^9$,
  phenyl substituted with 0–5 R$^9$, and
  5-6 membered heterocyclic system containing 1–3 heteroatoms selected from O, N, and S, substituted with 0–2 R$^9$; wherein the heterocyclic system is selected from 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, 1-pyrazolyl, 3-pyrazolyl, and 4-pyrazolyl;
R$^9$ is selected from methyl, ethyl, propyl, butyl, —CF$_3$, —CF$_2$CF$_3$, —CF$_2$CF$_2$CF$_3$, —OH, methoxy, ethoxy, propoxy, butoxy, —OCF$_3$, F, Cl, Br, I, —NR$^{14}$R$^{15}$, —NO$_2$, —CN, —C(O)R$^{16}$, —NHC(O)R$^{17}$, —NHC(O)NR$^{14}$R$^{15}$, —NHSO$_2$R$^{18}$, and —SO$_2$NR$^{14}$R$^{15}$;
R$^{14}$ and R$^{15}$ are independently selected from H, methyl, and ethyl;
R$^{16}$ is selected from H, OH, methyl, ethyl, methoxy, ethoxy, and NR$^{14}$R$^{15}$;
R$^{17}$ is selected from methyl, ethyl, methoxy, and ethoxy; and
R$^{18}$ is selected from methyl, ethyl, and phenyl.

8. A pharmaceutical composition, comprising: a pharmaceutically acceptable carrier and a therapeutically effective amount of a compound of claim 7.

9. A pharmaceutical composition, comprising: a pharmaceutically acceptable carrier and a therapeutically effective amount of a compound of claim 2.

10. A pharmaceutical composition, comprising: a pharmaceutically acceptable carrier and a therapeutically effective amount of a compound of claim 3.

11. A pharmaceutical composition, comprising: a pharmaceutically acceptable carrier and a therapeutically effective amount of a compound of claim 4.

12. A method for treating HIV infection, comprising: administering to a host in need of such treatment a therapeutically effective amount of a compound of claim 7, or a pharmaceutically acceptable salt form thereof.

13. A method for treating HIV infection, comprising: administering to a host in need of such treatment a therapeutically effective amount of a compound of claim 2, or a pharmaceutically acceptable salt form thereof.

14. A method for treating HIV infection, comprising: administering to a host in need of such treatment a therapeutically effective amount of a compound of claim 3, or a pharmaceutically acceptable salt form thereof.

15. A method for treating HIV infection, comprising: administering to a host in need of such treatment a therapeutically effective amount of a compound of claim 4, or a pharmaceutically acceptable salt form thereof.

* * * * *